(12) United States Patent
Graham et al.

(10) Patent No.: US 9,671,048 B2
(45) Date of Patent: Jun. 6, 2017

(54) MANIFOLD CONNECTION ASSEMBLY

(71) Applicant: IDEX Health & Science LLC, Oak Harbor, WA (US)

(72) Inventors: Craig Graham, Anacortes, WA (US); Eric Beemer, Anacortes, WA (US); Scott Ellis, Anacortes, WA (US); Troy Sanders, Oak Harbor, WA (US); Carl Sims, Rohnert Park, CA (US); Quan Liu, Rohnert Park, CA (US); Nathaniel Nienhuis, Coupeville, WA (US)

(73) Assignee: IDEX Health & Science LLC, Oak Harbor, WA (US)

(*) Notice: Subject to any disclaimer, the term of this patent is extended or adjusted under 35 U.S.C. 154(b) by 0 days.

(21) Appl. No.: 15/194,289

(22) Filed: Jun. 27, 2016

(65) Prior Publication Data

US 2016/0305586 A1    Oct. 20, 2016

Related U.S. Application Data

(63) Continuation-in-part of application No. 14/922,041, filed on Oct. 23, 2015.
(Continued)

(51) Int. Cl.
*A61B 10/00* (2006.01)
*F16L 15/08* (2006.01)
(Continued)

(52) U.S. Cl.
CPC .............. *F16L 15/08* (2013.01); *B01D 15/14* (2013.01); *B01D 15/163* (2013.01); *B01L 3/563* (2013.01);
(Continued)

(58) Field of Classification Search
CPC .................... B01L 2300/0838; G01N 30/6026
See application file for complete search history.

(56) References Cited

U.S. PATENT DOCUMENTS 3,880,452 A    4/1975  Fields
4,076,286 A    2/1978  Spontelli
(Continued)

FOREIGN PATENT DOCUMENTS

CN    2087340 U    10/1991
DE    4114765 A1   11/1992
(Continued)

OTHER PUBLICATIONS

Notice of Opposition dated Jan. 22, 2015.
(Continued)

*Primary Examiner* — Jyoti Nagpaul
(74) *Attorney, Agent, or Firm* — Vinson & Elkins LLP

(57) ABSTRACT

A manifold assembly has a manifold and can be located between a block and a plate, and serve as a stator for a valve or other component. The manifold, block or plate can have a plurality of ports either integral thereto or removably connected thereto, with the ports adapted to receive and sealingly engage with a tube having an inner tube layer, an outer tube layer, a sleeve, a tip portion, and a nut. Each of the nut, sleeve, inner and outer tubing layers, and tip portion have a passageway therethrough, with at least the passageways in the sleeve, tip portion, outer tube layer, and nut adapted to allow the inner tube layer to pass therethrough or extend over the inner layer. The ends of the tip portion and inner layer together can define a substantially flat surface which can form a seal in a flat-bottomed port of the manifold, block, or plate, which can be used in a component in an analytical instrument system, including for example a liquid chromatography system. The nut, tube, ferrule, and transfer tube or liner tube may comprise biocompatible
(Continued)

materials. In addition, the nut may have a slot, such as a slot adapted to allow the tube and the nut to be easily and quickly separated or to allow a portion of the tube to be easily and quickly inserted in the nut.

23 Claims, 42 Drawing Sheets

Related U.S. Application Data

(60) Provisional application No. 62/067,739, filed on Oct. 23, 2014, provisional application No. 62/127,276, filed on Mar. 2, 2015, provisional application No. 62/168,491, filed on May 29, 2015.

(51) Int. Cl.
  *F16L 19/02*   (2006.01)
  *B01L 3/00*    (2006.01)
  *B01D 15/14*   (2006.01)
  *B01D 15/16*   (2006.01)
  *G01N 30/60*   (2006.01)

(52) U.S. Cl.
  CPC ....... *F16L 19/0206* (2013.01); *F16L 19/0212* (2013.01); *B01L 2300/0838* (2013.01); *G01N 30/6026* (2013.01)

(56) References Cited

U.S. PATENT DOCUMENTS

| | | | |
|---|---|---|---|
| 4,083,702 A | 4/1978 | Hartigan et al. |
| 4,619,473 A | 10/1986 | Someya |
| 4,915,427 A | 4/1990 | Zahuranec |
| 5,169,120 A | 12/1992 | Guthrie, Jr. et al. |
| 5,306,052 A | 4/1994 | Megushion |
| 5,595,406 A | 1/1997 | Warchol |
| 5,601,785 A | 2/1997 | Higdon |
| 5,651,885 A | 7/1997 | Schick |
| 5,709,413 A | 1/1998 | Salyers |
| 6,056,331 A | 5/2000 | Benett et al. |
| 6,273,478 B1 | 8/2001 | Benett et al. |
| 6,494,500 B1 | 12/2002 | Todosiev et al. |
| 6,926,313 B1 | 8/2005 | Renzi |
| 7,014,222 B1 | 3/2006 | Poppe |
| 7,513,535 B2 | 4/2009 | Charles et al. |
| 8,006,367 B1 | 8/2011 | Best |
| 9,091,693 B2 | 7/2015 | Hochgraeber et al. |
| 9,334,989 B2 | 5/2016 | Jencks et al. |
| 2002/0101079 A1 | 8/2002 | Ehrke |
| 2007/0052237 A1 | 3/2007 | Udhofer et al. |
| 2009/0160133 A1 | 6/2009 | Williams et al. |
| 2009/0295156 A1 | 12/2009 | Ford et al. |
| 2011/0006519 A1 | 1/2011 | Weh |
| 2011/0298210 A1 | 12/2011 | Hochgraeber et al. |
| 2012/0024411 A1 | 2/2012 | Hahn et al. |
| 2012/0061955 A1 | 3/2012 | Hochgraeber et al. |
| 2013/0298647 A1 | 11/2013 | Falk-Jordan |
| 2013/0341260 A1 | 12/2013 | Dehmer |
| 2014/0145437 A1 | 5/2014 | Burger et al. |

FOREIGN PATENT DOCUMENTS

| | | |
|---|---|---|
| DE | 102008059897 A1 | 6/2010 |
| DE | 102009022368 B3 | 11/2010 |
| EP | 0087598 A2 | 9/1983 |
| EP | 2564104 A2 | 3/2013 |
| WO | 91/00470 A1 | 1/1991 |
| WO | 01/73338 A1 | 10/2001 |
| WO | 2006083597 A2 | 8/2006 |
| WO | 2006091952 A1 | 8/2006 |
| WO | 2010000324 A1 | 1/2010 |
| WO | 2010010884 A1 | 1/2010 |
| WO | 2011137452 A2 | 11/2011 |
| WO | 2012177403 A1 | 12/2012 |

OTHER PUBLICATIONS

A. Sonnenschein, H. Knauer, "Dynaseal-Connection System for HPLC", Chromatographia vol. 22, No. 7-12, Dec. 1986.
Dr. Herbert Knauer Wissenschaftliche Gerate KG, "Dynaseal-Verbindungssystem für die HPLC," 1986.
Excerpt from catalog "Scivex 2003, Upchurch Scientific Division: Catalog of Chromatography & Fluid Transfer Components," 2003.
International Search Report issued Mar. 3, 2016.

MANIFOLD CONNECTION ASSEMBLY

CROSS-REFERENCE TO RELATED APPLICATIONS

This application is a continuation-in-part and claims benefit of priority from U.S. Non-provisional patent application Ser. No. 14/922,041, filed Oct. 23, 2015, and from U.S. Provisional Patent Application No. 62/067,739, filed Oct. 23, 2014, U.S. Provisional Patent Application No. 62/127,276, filed Mar. 2, 2015, and U.S. Provisional Patent Application No. 62/168,491, filed May 29, 2015, each of which is hereby incorporated by reference herein.

FIELD OF THE INVENTION

The present disclosure relates generally to fitting assemblies and fluidic connection systems, such as those used in connecting components of liquid chromatography systems and other analytical instrument systems, and, more specifically, to manifold connection assemblies, valves, and fluidic connection systems for connecting tubing to manifolds.

BACKGROUND OF THE INVENTION

Liquid chromatography (LC) is a well-known technique for separating the constituent elements in a given sample. In a conventional LC system, a liquid solvent (referred to as the "mobile phase") is introduced from a reservoir and is pumped through the LC system. The mobile phase exits the pump under pressure. The mobile phase then travels via tubing to a sample injection valve. As the name suggests, the sample injection valve allows an operator to inject a sample into the LC system, where the sample will be carried along with the mobile phase.

In a conventional LC system, the sample and mobile phase pass through one or more filters and often a guard column before coming to the column. A typical column usually consists of a piece of steel tubing which has been packed with a "packing" material. The "packing" consists of the particulate material "packed" inside the column. It usually consists of silica- or polymer-based particles, which are often chemically bonded with a chemical functionality. The packing material is also known as the stationary phase. One of the fundamental principles of separation is the mobile phase continuously passing through the stationary phase. When the sample is carried through the column (along with the mobile phase), the various components (solutes) in the sample migrate through the packing within the column at different rates (i.e., there is differential migration of the solutes). In other words, the various components in a sample will move through the column at different rates. Because of the different rates of movement, the components gradually separate as they move through the column. Differential migration is affected by factors such as the composition of the mobile phase, the composition of the stationary phase (i.e., the material with which the column is "packed"), and the temperature at which the separation takes place. Thus, such factors will influence the separation of the sample's various components.

Once the sample (with its components now separated) leaves the column, it flows with the mobile phase past a detector. The detector detects the presence of specific molecules or compounds. Two general types of detectors are used in LC applications. One type measures a change in some overall physical property of the mobile phase and the sample (such as their refractive index). The other type measures only some property of the sample (such as the absorption of ultraviolet radiation). In essence, a typical detector in a LC system can measure and provide an output in terms of mass per unit of volume (such as grams per milliliter) or mass per unit of time (such as grams per second) of the sample's components. From such an output signal, a "chromatogram" can be provided; the chromatogram can then be used by an operator to determine the chemical components present in the sample.

In addition to the above components, a LC system will often include filters, check valves, a guard column, or the like in order to prevent contamination of the sample or damage to the LC system. For example, an inlet solvent filter may be used to filter out particles from the solvent (or mobile phase) before it reaches the pump. A guard column is often placed before the analytical or preparative column; i.e., the primary column. The purpose of such a guard column is to "guard" the primary column by absorbing unwanted sample components that might otherwise bind irreversibly to the analytical or preparative column.

In practice, various components in an LC system may be connected by an operator to perform a given task. For example, an operator will select an appropriate mobile phase and column, then connect a supply of the selected mobile phase and a selected column to the LC system before operation. In order to be suitable for high performance liquid chromatography (HPLC) applications, each connection must be able to withstand the typical operating pressures of the HPLC system. If the connection is too weak, it may leak. Because the types of solvents that are sometimes used as the mobile phase are often toxic and because it is often expensive to obtain and/or prepare many samples for use, any such connection failure is a serious concern.

It is fairly common for an operator to disconnect a column (or other component) from a LC system and then connect a different column (or other component) in its place after one test has finished and before the next begins. Given the importance of leak-proof connections, especially in HPLC applications, the operator must take time to be sure the connection is sufficient. Replacing a column (or other component) may occur several times in a day. Moreover, the time involved in disconnecting and then connecting a column (or other component) is unproductive because the LC system is not in use and the operator is engaged in plumbing the system instead of preparing samples or other more productive activities. Hence, the replacement of a column in a conventional LC system involves a great deal of wasted time and inefficiencies.

Given concerns about the need for leak-free connections, conventional connections have been made with stainless steel tubing and stainless steel end fittings. More recently, however, it has been realized that the use of stainless steel components in a LC system have potential drawbacks in situations involving biological samples. For example, the components in a sample may attach themselves to the wall of stainless steel tubing. This presents problems because the detector's measurements (and thus the chromatogram) of a given sample may not accurately reflect the sample if some of the sample's components or ions remain in the tubing, and do not pass the detector. Perhaps of even greater concern, however, is the fact that ions from the stainless steel tubing may detach from the tubing and flow past the detector, thus leading to potentially erroneous results. Additionally, ions can easily bind to biological compounds of interest, resulting in changes to the molecules that affect their retention time in the column. Hence, there is a need for "biocompatible" connections through the use of a material that is chemically inert with respect to such "biological" samples and the mobile phase used with such samples so that ions will not be released by the tubing and thus contaminate the sample.

In many applications using selector/injector valves to direct fluid flows, and in particular in liquid and gas chromatography, the volume of fluids is small. This is particularly true when liquid or gas chromatography is being used as an analytical method as opposed to a preparative method. Such methods often use capillary columns and are generally referred to as capillary chromatography. In capillary chromatography, both gas phase and liquid phase, it is often desired to minimize the internal volume of the selector or injector valve. One reason for this is that a valve having a large volume will contain a relatively large volume of liquid, and when a sample is injected into the valve the sample will be diluted, decreasing the resolution and sensitivity of the analytical method.

Micro-fluidic analytical processes also involve small sample sizes. As used herein, sample volumes considered to involve micro-fluidic techniques can range from as low as volumes of only several picoliters or so, up to volumes of several milliliters or so, whereas more traditional LC techniques, for example, historically often involved samples of about one microliter to about 100 milliliters in volume. Thus, the micro-fluidic techniques described herein involve volumes one or more orders of magnitude smaller in size than traditional LC techniques. Micro-fluidic techniques can also be expressed as those involving fluid flow rates of about 0.5 ml/minute or less.

Most conventional HPLC systems include pumps which can generate pressures of up to around 5,000 psi to 8,000 psi or so. In many situations, an operator can obtain successful results by operating a LC system at "low" pressures of anywhere from just a few psi or so up to 8,000 psi or so.

Another, relatively newer liquid chromatography form is Ultra High Performance Liquid Chromatography (UHPLC) in which system pressure extends upward to about 1400 bar or 20,000 psi or so, or even more. In order to achieve greater chromatographic resolution and higher sample throughput, the particle size of the stationary phase has become extremely small. A stationary phase particle as small as 1 micron is common; the resulting high column packing density leads to substantially increased system pressure at the head of the column. Both HPLC and UHPLC are examples of analytical instrumentation that utilize fluid transfer at elevated pressures. For example, in U.S. Patent Publication No. 2007/0283746 A1, published on Dec. 13, 2007 and titled "Sample Injector System for Liquid Chromatography," an injection system is described for use with UHPLC applications, which are said to involve pressures in the range from 20,000 psi to 120,000 psi. In U.S. Pat. No. 7,311,502, issued on Dec. 25, 2007 to Gerhardt, et aL, and titled "Method for Using a Hydraulic Amplifier Pump in Ultrahigh Pressure Liquid Chromatography," the use of a hydraulic amplifier is described for use in UHPLC systems involving pressures in excess of 25,000 psi. In U.S. Patent Publication No. 2005/0269264 A1, published on Dec. 8, 2005 and titled "Chromatography System with Gradient Storage and Method for Operating the Same," a system for performing UHPLC is disclosed, with UHPLC described as involving pressures above 5,000 psi (and up to 60,000 psi). Applicants hereby incorporate by reference as if fully set forth herein U.S. Pat. No. 7,311,502 and US Patent Publications Nos. 2007/0283746 A1 and 2005/0269264 A1.

As noted, liquid chromatography (as well as other analytical) systems, including HPLC or UHPLC systems, typically include several components. For example, such a system may include a pump; an injection valve or autosampler for injecting the analyte; a precolumn filter to remove particulate matter in the analyte solution that might clog the column; a packed bed to retain irreversibly adsorbed chemical material; the HPLC column itself; and a detector that analyzes the carrier fluid as it leaves the column. These various components may typically be connected by a miniature fluid conduit, or tubing, such as metallic or polymeric tubing, usually having an internal diameter of 0.001 to 0.040 inch.

All of these various components and lengths of tubing are typically interconnected by threaded fittings. Fittings for connecting various LC system components and lengths of tubing are disclosed in prior patents, for example, U.S. Pat. Nos. 5,525,303; 5,730,943; and 6,095,572, the disclosures of which are herein all incorporated by reference as if fully set forth herein. Often, a first internally threaded fitting seals to a first component with a ferrule or similar sealing device. The first fitting is threadedly connected through multiple turns by hand or by use of a wrench or wrenches to a second fitting having a corresponding external fitting, which is in turn sealed to a second component by a ferrule or other seal. Disconnecting these fittings for component replacement, maintenance, or reconfiguration often requires the use of a wrench or wrenches to unthread the fittings. Although a wrench or wrenches may be used, other tools such as pliers or other gripping and holding tools are sometimes used. It will be understood by those skilled in the art that, as used herein, the term "LC system" is intended in its broad sense to include all apparatus and components in a system used in connection with liquid chromatography, whether made of only a few simple components or made of numerous, sophisticated components which are computer controlled or the like. Those skilled in the art will also appreciate that an LC system is one type of an analytical instrument (AI) system. For example, gas chromatography is similar in many respects to liquid chromatography, but obviously involves a gas sample to be analyzed. Such analytical instrument systems include high performance or high pressure liquid chromatography systems, an ultra high performance or ultra high pressure liquid chromatography system, a mass spectrometry system, a microflow chromatography system, a nanoflow chromatography system, a nano-scale chromatography system, a capillary electrophoresis system, a reverse-phase gradient chromatography system, or a combination thereof. Although the following discussion focuses on liquid chromatography, those skilled in the art will appreciate that much of what is said also has application to other types of AI systems and methods.

Increasing pressure requirements in liquid chromatography have necessitated the use of high pressure fluidic components. For many applications regular stainless steel tubing can be used to withstand the high pressure. However, for some types of analyses (e.g., biological testing and metal/ion analysis), stainless steel or other metals are not desired in the fluid path as the metal could interfere with the testing. Additionally, there are some fields of use (e.g., nano-scale or nano-volume analysis), that require very small inside diameters to accommodate the extremely low volumes required by these applications. Such small inside diameters are typically not available in stainless steel or other high pressure tubing.

In high-performance liquid chromatography (HPLC), ultra high-performance liquid chromatography (UHPLC), and other high-pressure analytic chemistry applications, various system components and their fluidic connections must be able to withstand pressures of 15,000 to 20,000 psi or so. The types of fluidic connection systems between the tubes that carry fluids and the ports that receive fluids in these high-pressure applications are limited. Many fluidic connection systems rely on cone-shaped, threaded, or welded fittings to attach a tube to a receiving port. These types of connections sometimes may have drawbacks, however. For example, the size of cone-shaped fittings and threaded fittings are dependent on the type and size of any given port, which makes quickly interchanging a tube fitted with a particular cone or threaded fitting between various ports difficult. Other compression-based fittings have been employed to address this problem. Such fittings often employ a ferrule or a lock ring to help secure one end of a tube to a receiving port. However, ferrules and lock rings can become deformed after multiple uses (e.g., by connecting, disconnecting, and reconnecting to various ports). This is especially true in high-pressure applications, where a fluid-tight seal is essential, and where a ferrule or lock ring may be more likely to become deformed in creating such a seal.

For example, published U.S. Patent Application No. 2013/0043677, titled "Tube and Pipe End Cartridge Seal," published on Feb. 21, 2013, describes a tube and pipe end cartridge seal for use at high pressures, which relies on a fitting body (including ferrule fittings) to effectuate a seal with the axial end of a tube. Moreover, a dimple is forged on the annular end of the tube face to further effectuate the seal. Likewise, U.S. Pat. No. 6,056,331, titled "Zero Dead Volume Tube to Surface Seal," issued to Bennett et al. on May 2, 2000, describes an apparatus for connecting a tube to a surface using a body, a ferrule, and a threaded fitting. Although Bennett et al. discloses a type of tube face-sealing apparatus, the apparatus of Bennet et al. relies on a threaded fitting and a ferrule. Similarly, published U.S. Patent Application No. 2012/0061955, titled "Plug Unite and Connection System for Connecting Capillary Tubes, Especially for High-Performance Liquid Chromatography," published on Mar. 15, 2012, discloses a plug unit connection system for capillary tubes, wherein a seal is provided at the interface between a capillary tube and a bushing unit, instead of at the location of a ferrule or conical fitting. However, U.S. Patent Application No. 2012/0061955 relies on the use of a pressure piece similar to a ferrule to ensure that enough axial force can be generated to obtain a seal at the tube face.

Connection assemblies which attempt to effectuate a seal for high-pressure applications can require a significant amount of torque to effectuate a fluid-tight seal, making the creation of such seals difficult without the use of additional tools and increasing the risk of damage to the fitting assembly or its components due to overtightening. Moreover, experience suggests that many users do not like to use various tools to connect or disconnect tubing from components such as those in various AI systems. It is believed that users often apply different amounts of torque to connect or disconnect tubing and the components in such systems, thus resulting in potential problems caused by over-tightening or under-tightening (e.g., leakage or loss of sealing when the fluid is under pressure).

One example of a flat-bottomed or face-sealing connection assembly is provided by U.S. Pat. No. 8,696,038, titled "Flat Bottom Fitting Assembly" and issued on Apr. 15, 2014 to Nienhuis. Nienhuis teaches a type of flat bottom assembly which includes a flat-sided ferrule, and wherein the assembly including the ferrule and the tube can be pressed against a flat bottom port. Another example of a flat-bottomed or face-sealing connection assembly is provided by published U.S. Patent Application No. 2012/0024411, titled "Biocompatible Tubing for Liquid Chromatography Systems," which was published on Feb. 2, 2012 and was filed on behalf of Hahn et al. The Hahn et al. published patent application describes tubing having an inner layer and an outer layer, and in which the inner layer can be biocompatible material such as polyetheretherketone (PEEK) and the outer layer may be a different material, and in which an end of the tubing may be flared or otherwise adapted to have a larger outer diameter than other portions of the tubing. The current state of the art for high pressure connections in both HPLC and UHPLC is to utilize coned ports along with some form of ferrule and nut combination with tubing. The nut translates rotational torque into axial load that is translated to the ferrule. The load causes the ferrule to deform/deflect and grip the tubing, creating a seal. The tube is typically forced into the bottom of the coned port, but there is not currently a mechanism to ensure there is not a gap or space at the port bottom.

The space at the bottom of the port is a concern for those performing liquid chromatography experiments due to the potential to negatively influence the results with carry over and band broadening. Carry over is just as it sounds, analyte from one test is carried over to the next. Carry over can produce very unstable results for obvious reasons. Band broadening is when the peaks identifying a substance become less symmetric and make identification more difficult when peaks of different molecules have similar retention times.

One issue with conventional ferrules used with coned ports is that the torque required to deform/deflect is typically above finger tight levels in order to achieve UHPLC pressures (e.g., above 12,000 psi or so). It is desirable to remove tools from the lab by making them unnecessary for making and breaking fluidic connections and it is advantageous to have fittings that can be connected simply with the fingers rather than tools.

European Patent No. EP 2564104 describes a sealing system for use at high pressure. End-face seals minimize the sealing radius and therefore allow various fittings—including known ferrule fittings—to be used in high-pressure systems. End-face seals at such high pressure may require smooth surfaces, however. In order to reduce cost, an end-face preparation tool may be required to forge a dimple into the end face to mechanically deform and smooth the surface.

U.S. Pat. No. 6,056,331 describes an apparatus that is composed of three components, a body, a ferrule, and a threaded fitting. The ferrule is compressed onto a tube and a seal is formed between the tube and a device retained in the body by threading the fitting into the body which provides pressure that seals the face of the ferrule to a mating surface on the device. This seal may be used at elevated temperatures, depending on the materials used. This fitting was developed for use with micro-machined silicon wafers used in capillary gas chromatography.

Valves and methods of using valves in LC and AI systems have been known. For example, U.S. Pat. No. 6,910,503, titled "Methods and Apparatus for Micro-Fluidic Analytical Chemistry" and issued on Jun. 28, 2005 to Schick et al., describes a valve for use in an LC system. The Schick et al. patent also describes a valve having various elements included in one or more stators or components of the valve, such as one or more of a sample loop, column, detector, mixer, heating element, electro-osmotic pump, and the like, such as may be provided by micro electro-mechanical systems incorporated into the valve.

Manifolds also have been provided in the past for use with LC systems. For example, US Published Patent Application No. 2016/0003383, published on Jan. 7, 2016, and titled "Integrated Fluidic Connection of Planar Structures for Sample Separation Devices," describes a manifold having a multi-layer planar structure with multiple laminated layers, with each layer potentially patterned by etching or lithography to provide fluidic pathways or channels. Such a manifold also has a female adapter piece attached thereto that is adapted to align with a fluid conduit in a male adapter piece connected thereto to allow fluid to flow in or out of the fluidic pathways of the manifold. Further, the manifold may include one or more elements therein, such as a column, a heat exchanger, a valve, a mixer, a splitter, a polymerase chain reaction unit, a detector, a switch, or the like.

In U.S. Pat. No. 9,188,571, issued to Michienzi on Nov. 17, 2015, and titled "Chromatography Apparatus Having Diffusion Bonded Coupler," a manifold assembly is described that includes a metal coupler which is diffusion bonded to the surface of a manifold layer which is a ceramic material, with an opening in the coupler aligned with an inlet in the manifold layer. The manifold may include one or more columns, such as analytical columns or trap columns.

U.S. Pat. Nos. 5,525,303, 5,730,943, 6,056,331, 6,095,572, 6,056,331, 7,311,502, 6,910,503, 8,696,038, 9,188,571, European Patent No. EP2564104, and published U.S. Patent Application Nos. 2005/0269264, 2007/0283746, 2012/0024411, 2012/0061955, 2013/0043677, and 2016/0003383 are hereby incorporated by reference as if fully set forth herein.

SUMMARY OF THE INVENTION

It is therefore an object of the present disclosure to provide a fluidic connection system useful for high-pressure applications. The system can provide a sealing connection without the use of additional parts such as ferrules, locking rings, or other fittings. It is a further object of the present disclosure to provide a fluidic connection system, wherein the axial force necessary to create an effective seal for high-pressure applications can be generated manually, with minimal torque and without the use of tools. It is a further object of the present disclosure to provide a fluidic connection system which is flexible and can be quickly and easily connected and disconnected with various tubes and ports without damaging the connection system.

In one embodiment of the present disclosure, a fitting assembly comprises a nut having a passageway extending therethrough and having a first end and a second end, wherein said nut has an externally threaded portion near the second end of said nut, a tube having a portion extending through the passageway in said nut, wherein said tube comprises an inner layer and an outer layer, each having a first end and a second end and each layer having an inside diameter and an outside diameter, wherein the outer layer of said tube has an inside diameter greater than the outside diameter of the inner layer, and wherein the first end of said tube comprises a tip portion, wherein the tip portion has an inner diameter and an outer diameter and a portion of the inner layer of said tube is located within the inner diameter of the tip portion, and wherein at least one of a first end of the tip portion and the first end of the inner layer define a surface adapted to form a seal with a port, and a sleeve having a passageway therethrough and having a first end and a second end, with at least a portion of the first end of said sleeve adapted to fit against a surface of said nut and at least a portion of the second end of said sleeve located between the outside diameter of a portion of the inner layer of said tube and the inner diameter of the tip portion of said tube, wherein the tip portion of said tube extends over at least a portion of the inner layer of said tube, at least a portion of the outer layer of said tube, and over at least a portion of the sleeve. The outer layer of said tube may comprise a first material and the inner layer of said tube may comprise a second material, and the two materials may be different. The fitting assembly according to claim 2 wherein the first material comprises a material different than the second material. The sleeve and the outer tube layer may each comprise a metal material, and the inner layer of said tube and the tip of said tube may comprise a biocompatible material, such as polyetheretherketone (PEEK). In addition, the sleeve may further comprise a retention feature, such as a lip. The tip of the tube may be overmolded over and onto a portion of the inner tube layer.

In another embodiment of the present disclosure, a tubing assembly is provided, which comprises a tube having an inner layer and an outer layer, each having a first end and a second end and each having an inside diameter and an outside diameter, wherein said tube further comprises a tip portion having a first end, and wherein at least one of a first end of the inner layer of said tube and the first end of the tip portion of said tube defines a substantially flat surface adapted to contact and form a seal against a flat-bottomed port, and a sleeve having a passageway therethrough and having a first end and a second end, with at least a first portion of said sleeve located between the outside diameter of a portion of the outer layer of said tube and a second portion of said sleeve located between the inner diameter of a portion of the tip portion of said tube and the outside diameter of the inner layer of said tube. In such a tubing assembly, the sleeve may comprise a metal such as stainless steel, the inner layer of said tube may comprise a biocompatible material such as PEEK, the outer layer of said tube may comprise a material such as stainless steel, and the tip portion of said tube may comprises a biocompatible material, such as PEEK.

In another embodiment, an analytical instrument system is provided which comprises at least two components having fluid communication therebetween, wherein at least one of said components has a flat-bottomed port having a face, a tube comprising an inner layer and an outer layer, each having a first end and a second end and each having an inside diameter and an outside diameter, said tube further comprising a tip portion, wherein a first end of the tip portion of said tube defines a substantially flat surface, and wherein the tip portion of said tube has a greater outside diameter than the outside diameter of the inner layer, a sleeve having a passageway therethrough and having a first end and a second end, with at least a portion of the first end of said sleeve located between the outside diameter of a portion of the inner layer of said tube and the inner diameter of a portion of the tip portion of said tube, wherein the tip portion of said tube extends over at least a portion of the inner layer and over at least a portion of the sleeve, wherein the first end of the tip portion and the face of the flat-bottomed port are in a sealing engagement, and wherein either or both of said components comprise any one of the following: pumps, columns, filters, guard columns, injection valves, and other valves, detectors, pressure regulators, reservoirs, degassers, unions, tees, crosses, adapters, splitters, sample loops, and/or connectors. Both the inner layer and the tip portion of said tube may comprise a biocompatible material, such as PEEK.

In another embodiment, a fitting assembly is provided in which a nut has one or more slots, which can extend the longitudinal length of the nut and which can extend radially from the passageway through the nut to the exterior of the nut. The nut can have one or more such slots, and the slots can extend along only a portion of the longitudinal length of the nut if desired. In addition, the slot can be adapted so that tubing can be easily inserted into the interior passageway of the nut by an operator, or can be easily removed from the nut by an operator. The slot is adapted so that a tube or a portion of a tube can be easily inserted into or removed from the nut through the slot.

In another embodiment in accordance with the present disclosure, a manifold assembly is provided which includes at least one nut having a passageway therethrough and having a first end and a second end, a block adapted to removably hold a manifold and having a plurality of ports therein, wherein each of the ports are adapted to removably and sealingly engage with said nut and an end of a tube, a manifold having a plurality of inlet ports therein, wherein at least a portion of said manifold is attached to said block, and wherein each of the ports of said block is in fluid communication with one of the inlet ports of said manifold, a tube having a passageway therethrough and adapted to fit in a passageway extending through said nut, wherein said tube has a first end and a second end, a transfer tube having a passageway therethrough, wherein at least a portion of said tube is located within the passageway of said transfer tube and is secured relative to said transfer tube, a tube tip having a passageway therethrough and providing an interior portion, wherein said tip is adjacent to and in contact with one of the first end and the second end of said tube, wherein said tip is adapted to receive and hold a portion of one of the first end and the second end of said tube in the interior portion, wherein at least a portion of one end of the tip is adapted to form a seal in a port in fluid communication with said manifold, and wherein a portion of the tip is located between a portion of said tube and a portion of said transfer tube. In this particular embodiment, the manifold may also comprise a stator for a valve, which may be a part of a liquid chromatography system, and may also comprise two or more stators for multiple valve application in a liquid chromatography system.

The tube in this particular embodiment may comprise an inner tube and an outer tube, and the tip may comprise a compressible material, and at least one of said transfer tube and an inside surface of said tip may be adapted to provide an interference fit with said tube. In addition, the transfer tube may have a shorter length than the tube and one end of said transfer tube may be adapted to impinge on a portion of one end of said tip, thereby forcing said tip against a port bottom when an axial load is applied. The tube may comprise a single metal, the transfer tube may comprise a metal, and the transfer tube may comprise a pocket portion at a terminal end thereof. The tip may be adapted to be held in the pocket portion, thereby providing an interference seal with a portion of said tube. The tube and the tube tip may each comprise a biocompatible material, such as one or more of the following: polyetheretherketone (PEEK), polyaryletherketone (PAEK), polyetherketone (PEK), polyetherketone etherketone ketone (PEKEKK), polyetherketoneketone (PEKK), fluorinated ethylene propylene (FEP), ethylene tetrafluoroethylene (ETFE), polytetrafluoroethylene (PTFE), perfluoroalkoxy (PFA, also called perfluoroalkoxyethylene), polychlorotrifluoroethylene (PCTFE), polymer-sheathed fused silica (such as PEEKSil), fused silica, or silica borite.

The manifold may be located between a block and a plate, and the tip of the tubing may form a seal with a bottom end of a port in the block, with such seal sufficient to withstand fluidic pressures of at least 5,000 psi, at least 10,000 psi, at least 15,000 psi, or at least 20,000 psi. The block may have at least four ports on a first face thereof, or the block may have a first face and a second face, and at least three edges, and may further have at least two ports located on at least two of its edges. In addition, the manifold may have at least one fluid pathway therein comprising a flow sensor, a temperature sensor, a pressure sensor, a sample loop, a mixer, a splitter, a heater, a pump, or a micro-electromechanical system.

In yet another embodiment in accordance with the present disclosure, a manifold assembly is provided, with the manifold assembly comprising a manifold having a first face with plurality of inlet ports therein and having a plurality of openings in the face corresponding to each of the inlet ports, wherein each of the plurality of openings is adapted to receive and securely hold at least one projection, at least one flat-bottomed port having a first end and a second end, wherein the second end of said port has a plurality of projections each adapted to removably fit into one of the openings in the face of said manifold, and wherein said port is adapted to receive and securely and removably hold therein a nut and an end of a tube, a nut having a passageway therethrough and having one end adapted to fit into and securely and removably engage with said port, a tube having a passageway therethrough and adapted to fit in the passageway of said nut, wherein said tube has a first end and a second end, a transfer tube having a passageway therethrough, wherein at least a portion of said tube is located within the passageway of said transfer tube and is secured relative to said transfer tube, a tip having a passageway therethrough and providing an interior portion, wherein said tip is adjacent to and in contact with one of the first end and the second end of said tube, wherein said tip is adapted to receive and hold a portion of one of the first end and the second end of said tube in the interior portion, wherein at least a portion of one end of the tip is adapted to form a seal in a port in fluid communication with said manifold, and wherein a portion of the tip is located between a portion of said tube and a portion of said transfer tube. The manifold may be adapted to provide a stator for a valve in an analytical instrument system. The manifold may further comprise a plurality of inlet or outlet ports on the first face of said manifold and a plurality of fluid pathways between each of the inlet ports and each of the inlet or outlet ports of said manifold. The tip may comprise a compressible material and wherein at least one of said transfer tube and an inside surface of said tip may be adapted to provide an interference fit with said tube. The port may be flat-bottomed and may comprise an alignment mask to help an operator to align one or more tips of the projection with one or more inlet or outlet ports of the manifold.

In other embodiments of the present disclosure, a manifold connection assembly is provided in which the connection assembly comprises a manifold and one or more connections which each comprise a capillary tube, a portion of which extends through a passageway in a nut, with a sleeve or sealing element surrounding a portion of the tube. In one embodiment, the sleeve may have an attachment which crimps or pushes against a portion of the sleeve and crimps or pushes the sleeve against a sealing element, which in turn crimps or pushes against a portion of the capillary tube, such that the tube, sleeve, and sealing element do not rotate independently of each other, but instead rotate together, and are pushed downward together when the nut is threadably engaged with a port during the connection or assembly process. In addition, in some embodiments the sealing element has a portion at one end with an outer diameter which is close to or the same as the inner diameter of the port, and provides a radial seal between the sealing element and the port wall in addition to a seal between the bottom face of the sealing element and the surface of the manifold at the bottom of the port. The sleeve and/or sealing element may have various configurations as disclosed herein for various embodiments. In some embodiments, a collet is attached to a portion of the capillary tube, with one end of the collet adapted to abut a bottom end of the nut when the assembly is being connected. The collet in such an embodiment is urged downward during the connection process when the nut is turned to threadably engage with the port, thereby pushing the end of the capillary tube against the manifold surface. The collet may also have various configurations, such as those illustrated and described in the present disclosure.

Each of the fitting assembly, tubing assembly, and analytical instrument system of the present disclosure are adapted to provide at least one sealing connection for a fluid connection in which the fluid has a pressure of between 0 psi and 25,000 psi, between 1,000 psi and 20,000 psi, and/or between 2,500 psi and 10,000 psi. Such a sealing connection can be made by a user without the use of tools or ferrules, and is adapted so that it can be made with a flat-bottomed port.

These and numerous other features, objects and advantages of the present disclosure will become readily apparent to those skilled in the art upon a reading of the detailed description, claims and the drawings.

DETAILED DESCRIPTION

Figure 1:
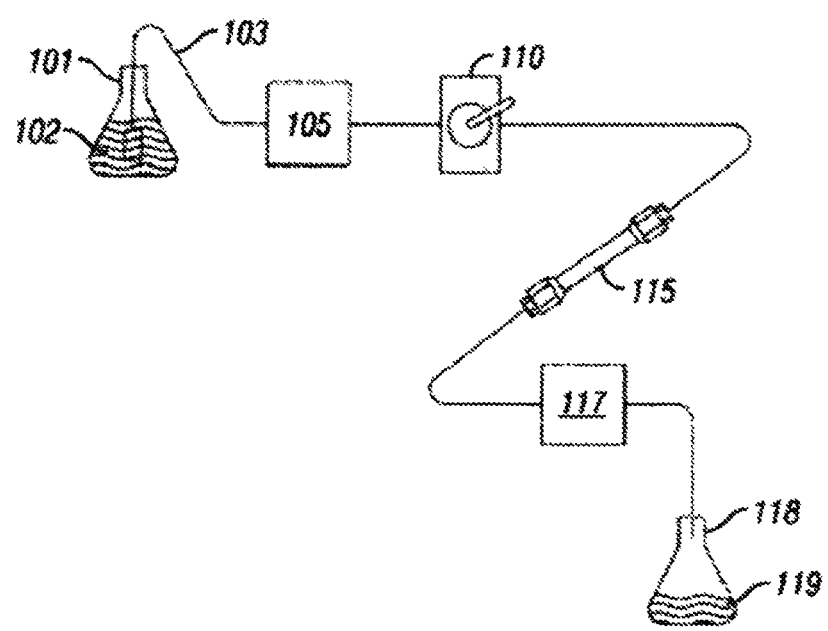
FIG. 1 is a block diagram of a conventional liquid chromatography system.

In FIG. 1, a block diagram of the essential elements of a conventional liquid chromatography (LC) system is provided. A reservoir 101 contains a solvent or mobile phase 102. Tubing 103 connects the mobile phase 102 in the reservoir 101 to a pump 105. The pump 105 is connected to a sample injection valve 110 which, in turn, is connected via tubing to a first end of a guard column (not shown). The second end of the guard column (not shown) is in turn connected to the first end of a primary column 115. The second end of the primary column 115 is then connected via tubing to a detector 117. After passing through the detector 117, the mobile phase 102 and the sample injected via injection valve 110 are expended into a second reservoir 118, which contains the chemical waste 119. As noted above, the sample injection valve 110 is used to inject a sample of a material to be studied into the LC system. The mobile phase 102 flows through the tubing 103 which is used to connect the various elements of the LC system together.

When the sample is injected via sample injection valve 110 in the LC system, the sample is carried by the mobile phase through the tubing into the column 115. As is well known in the art, the column 115 contains a packing material which acts to separate the constituent elements of the sample. After exiting the column 115, the sample (as separated via the column 115) then is carried to and enters a detector 117, which detects the presence or absence of various chemicals. The information obtained by the detector 117 can then be stored and used by an operator of the LC system to determine the constituent elements of the sample injected into the LC system. Those skilled in the art will appreciate that FIG. 1 and the foregoing discussion provide only a brief overview of a simplistic LC system that is conventional and well known in the art, as is shown and described in U.S. Pat. No. 5,472,598, issued Dec. 5, 1995 to Schick, which is hereby incorporated by reference as if fully set forth herein. Those skilled in the art will also appreciate that while the discussion herein focuses on a LC system, other analytical systems can be used in connection with various embodiments of the invention, such as a mass spectrometry, microflow chromatography, nanoflow chromatography, nano-scale liquid chromatography, capillary electrophoresis, or reverse-phase gradient chromatography system.

Preferably, for an LC system to be biocompatible, the various components (except where otherwise noted) that may come into contact with the effluent or sample to be analyzed are made of the synthetic polymer polyetheretherketone, which is commercially available under the trademark "PEEK" from Victrex. The polymer PEEK has the advantage of providing a high degree of chemical inertness and therefore biocompatibility; it is chemically inert to most of the common solvents used in LC applications, such as acetone, acetonitrile, and methanol (to name a few). PEEK also can be machined by standard machining techniques to provide smooth surfaces. Those skilled in the art will appreciate that other polymers may be desirable in certain applications.

Figure 2:
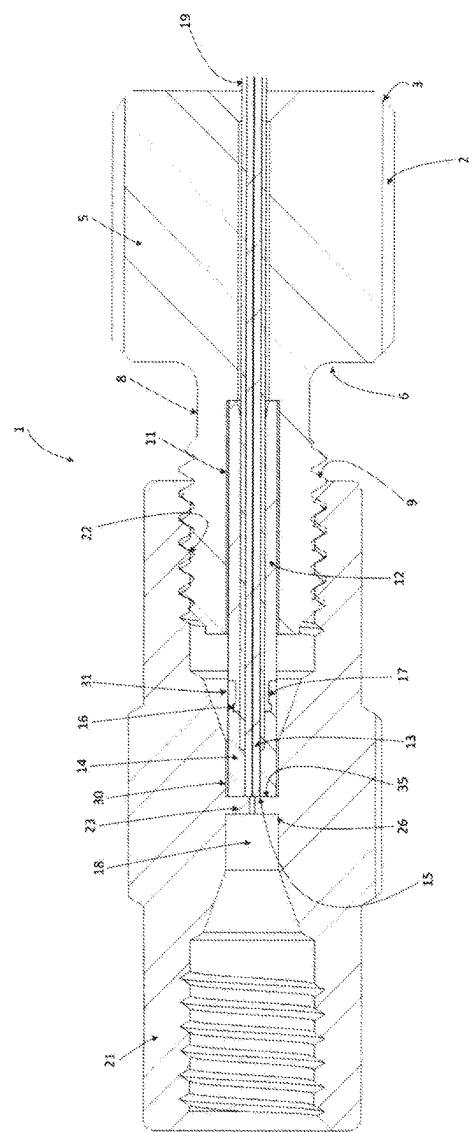
FIG. 2 is a detailed cross-sectional view of one embodiment of the fluidic connection system.

Referring now to FIG. 2, a detailed cross-sectional view of one embodiment of a fitting assembly for a fluidic connection system 1 is shown. Fluidic connection system 1 includes an actuator nut 2. Actuator nut 2 includes a first portion 6 proximate to the end 5 of the head of nut 2, and a non-tapered portion 8 proximate to the first portion 6. The actuator nut 2 also includes an externally threaded portion 9 having threads in a shape which corresponds to the shape of a first internally threaded portion 22 of a housing body 21. As shown in FIG. 2, housing body 21 comprises a union, but those skilled in the art will appreciate that instead of a union, the housing body 21 could be any one of a wide variety of components in an LC, HPLC, UHPLC, or other AI system, including for example, any of the following: pumps, columns, filters, guard columns, injection valves and other valves, detectors, pressure regulators, reservoirs, and other fittings, such as unions, tees, crosses, adapters, splitters, sample loops, connectors, and the like.

As shown in FIG. 2, said externally threaded portion 9 of said actuator nut 2 is rotatably engaged with the internally threaded portion 22 of said housing body 21, thereby removably connecting said nut 2 to the housing body 21. The rotatable engagement of said externally threaded portion 9 of said nut 2 with the internally threaded portion 22 of said housing body 21 removably secures said actuator nut 2 to said housing body 21. (By turning the head portion of nut 2 in the opposite direction, a user can also disconnect the nut 2 from the housing body 21.) When connected (as shown in FIG. 2), axial force on the tube end face 15 is provided when the actuator nut 2 is rotated. As shown in FIG. 2, the rotation of nut 2 relative to body 21 results in the externally threaded portion of nut 2 extending further into the port of body 21, until the port end face 35 and tube end face 15 touch. The force exerted on the tube end face 15 by rotating said actuator nut 2 forms a seal at the interface of the tube end face 15 and the port end face 35.

Tube end face 15 is defined by an end face of an inner tube layer 13 and an end face of an outer tube tip 14. The outer tip 14, sometimes referred to herein as the tube tip 14 or as tip 14, has a first end 30 and a second end 31, with said tube end face 15 being proximate to the first end 30. Between said first end 30 and said second end 31, tube tip 14 surrounds an inner layer 13 of the tube. In one embodiment, tube tip 14 is secured to a sleeve 12 of the tubing assembly by a retainer feature 16, which can be a feature or combination of features of a sleeve 12. Proximate to the second end 31 of said overmolded tube tip 14, a sleeve 12 surrounds the inner tubing layer 13. In one embodiment, sleeve 12 surrounds said inner tubing layer 13 between the second end 31 of said tube tip 14 and the first end 3 of said actuator nut 2. As shown in FIG. 2, sleeve 12 and inner tubing layer 13 extend and pass through a passageway through the axial length of the actuator nut 2, between the externally threaded portion 9 by means of a passageway 11.

The use of an internally threaded portion 22 on said housing body 21 is a matter of choice. Those skilled in the art will therefore appreciate that, in an alternative embodiment, the nut 2 could have an internally threaded portion (not shown) and the housing body 21 could have an externally threaded portion (not shown).

Figure 3:
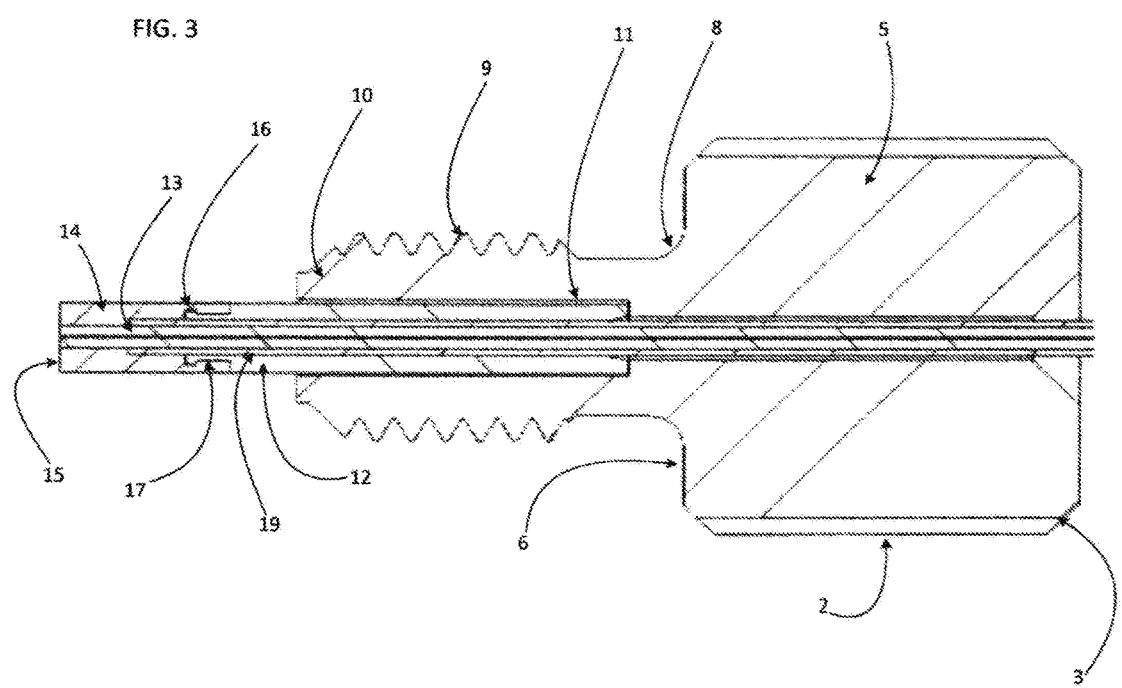
FIG. 3 is an cross-sectional view of one embodiment of a fitting assembly of the fluidic connection system.

Although not shown in FIG. 2, the tubing inner layer 13 preferably has an outer layer surrounding at least a portion thereof. Referring now to FIG. 3, a tubing outer layer 19 can be seen. As shown in FIG. 3, the outer layer 19 is located outside and around the inner tubing layer 13. In addition, a portion of the outer tubing layer 19 is located inside the sleeve 12, and an end portion of the outer tubing layer 19 extends beyond an end of the sleeve 12 and is located inside the overmolded tube tip 14. As also shown in FIG. 3, a portion of the inner layer 13 extends beyond the end of the outer layer 19 in this embodiment. In one particular embodiment, the sleeve 12 and outer tubing layer 19 can be secured to each other, such as by welding, adhesives, or by resin epoxies or other plastics, which can be located between the outside diameter of the outer layer 13 and the inner diameter of the sleeve 12. Securing the outer tubing layer 19 and the sleeve 12 helps prevent rotation of either independent of the other.

It will be appreciated that the tubing layer 13 can comprise a number of different materials depending on the particular application, as that may involve a particular type of sample, a particular type of solvent, and/or a particular pressure range. For example, the outer layer 19 of tube can comprise a metal, such as stainless steel (such as 316 stainless steel) or titanium, or a reinforced polymeric material, including composite or braided materials, such as polymeric materials that are reinforced or braided with carbon, carbon fibers, steel fibers, or the like. In embodiments comprising a metallic outer layer 19, the metal temper can be varied to provide a balance between high pressure capability and tubing flexibility. The inner layer 13 can comprise a biocompatible polymer, such as polyetheretherketone (PEEK). Other polymer materials which may be used for the inner layer 13 include, but are not limited to, TEFLON®, TEFZEL®, DELRIN®, perfluoroalkoxy (PFA, also called perfluoroalkoxyethylene), fluorinated ethylene propylene (PEP), polytetrafluoroethylene (PETE), ETFE (a polymer of tetrafluoroethylene and ethylene), polyetherimide (PEI), polyphenylene sulfide (PPS), polypropylene, sulfone polymers, polyolefins, polyimides, other polyaryletherketones, other fluoropolymers, polyoxymethylene (POM), and others, depending on the foregoing factors or perhaps others. In addition, PEEK (or other polymers) may be used that is reinforced or braided with carbon, carbon fibers, steel fibers, or the like. Furthermore, in certain embodiments the inner layer 13 may be coated with a material to increase strength, improve chemical resistance, improve temperature stability, or reduce permeability. Such coatings include, but are not limited to, metallization, polymeric coating, silicon-based coatings, and carbon-based coatings. Additionally, in certain embodiments the inner layer may be heat treated to improve properties such as crystallinity, chemical resistance, or permeability. Those skilled in the art will appreciate that, although shown and described herein as a single layer, the inner layer 13 of the tube may actually comprise two or more layers if desired. The final tube may be treated to further improve the performance, including heat treatment or annealing to strengthen the polymer components, or pressurizing, with or without added heat, to allow the inner layer to conform to the outer layer. A mandrel can be used in the inner diameter of the inner layer to preserve the passageway.

Actuator nut 2, inner tubing layer 13, sleeve 12, and retainer feature 16 may be embodied in a variety of configurations. Turning now to FIG. 3, overmolded tube tip 14 is secured to the sleeve 12 by retainer feature 16. The same numerals are used throughout the Figures as appropriate to identify the same features for convenient reference. As shown in FIG. 3, the retainer feature 16 has a protrusion which extends away from the inner layer 13 of the tube and towards the outer diameter of outer layer 14. The retainer feature 16 extends into a portion of the overmolded tube tip 14. Retainer feature 16 prevents the overmolded tube tip 14 from disengaging from the sleeve 12 and inner tubing layer 13. Retainer feature 16 also helps prevent the overmolded tube tip 14 from slipping while radial torque is being applied to the actuator nut 2 and axial force is being applied to the tube end face 15. Those skilled in the art will also appreciate that the retainer feature 16 may be of different configurations. For example, more than one retainer feature 16 may be used (not shown). Alternatively, the retainer feature 16 may be of a different shape or size than suggested by FIG. 3. Alternatively, the retainer feature 16 may be substituted by alternate means of securing the overmolded tube tip 14 to the sleeve 12, such as by means of an adhesive or by means of welding the overmolded tube tip 14 to the sleeve 12.

Figure 4:
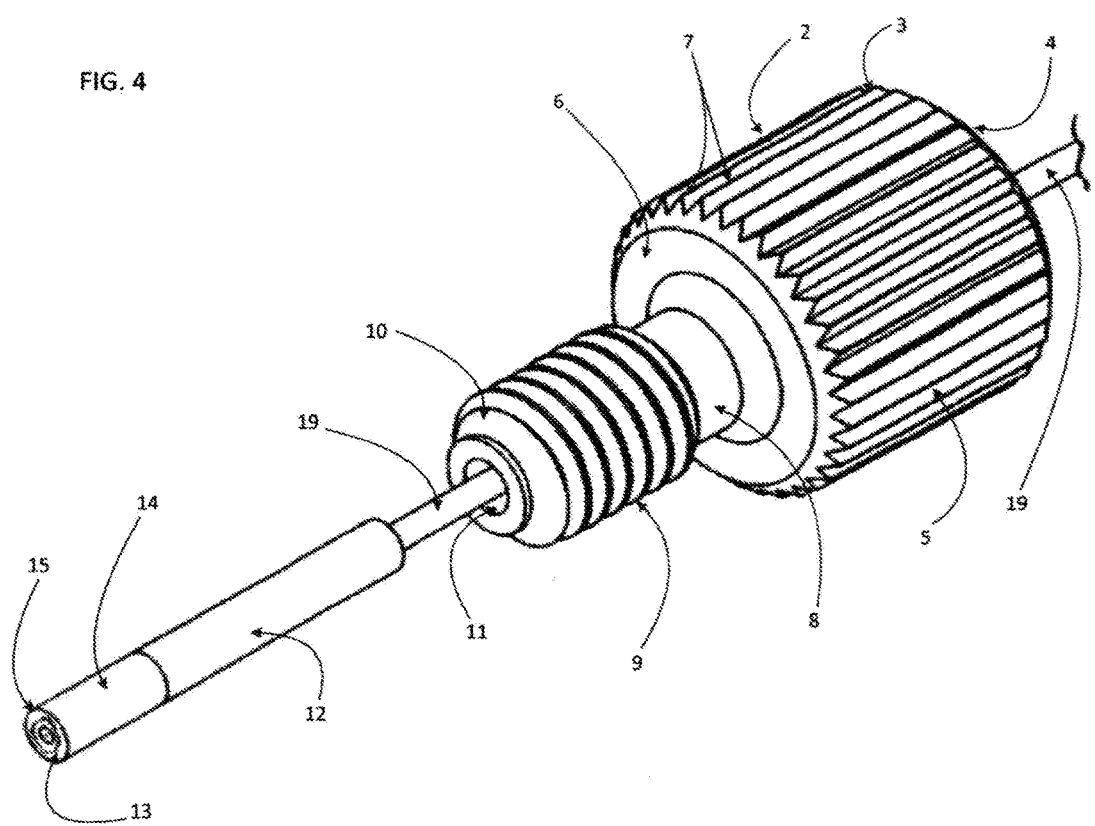
FIG. 4 is an isometric exterior view of the fitting assembly shown in FIG. 2.

Referring now to FIG. 4, another view of the fitting assembly is shown. As shown in FIG. 4, actuator nut 2 preferably has a circular shape, and the exterior surface of the head portion of said actuator nut 2 has a plurality of splines 7 spaced around the head of the nut 2. While those skilled in the art will appreciate the advantages of a circular-shaped actuator nut 2, those skilled in the art will also appreciate that the actuator nut 2, and/or the head of the nut 2, may have a non-circular shape, such as a box shape (not shown), a hexagonal shape (not shown), or other shapes. In addition, those skilled in the art will appreciate that the exterior surface of the actuator nut 2 may be flat (not shown) or cross-hatched (not shown), instead of characterized by splines 7. A variety of actuator nut 2 shapes and exterior surfaces may be used such that said actuator nut 2 may be easily gripped and manually rotated by an operator.

As shown in FIG. 4, the sleeve 12, inner tubing layer 13, and outer tubing layer 19 can be adapted to fit at least partially into a passageway 11. Inner and outer tubing 13 and 19, respectively, exit the actuator nut 2 through a hole (not shown) in the head 5 of the nut 2 proximate to the first end 3 of the actuator nut 2. Inner tubing layer 13 is preferably comprised of a biocompatible material such as synthetic polymer polyetheretherketone, which is commercially available under the trademark PEEK™ from VICTREX®. The outer layer 19 is preferably metal, such as stainless steel. Overmolded tube tip 14 can also comprise PEEK™ in this particular embodiment. Those skilled in the art will appreciate that inner tubing layer 13 and said overmolded tube tip 14 may be comprised of other polymer materials, including for example TEFLON®, TEFZEL®, DELRIN®, perfluoroalkoxyethylene (PFA), polytetrafluoroethylene (PETE), polyetherimide (PEI), polyphenylene sulfide (PPS), polypropylene, polyolefins, polyimides, or polyoxymethylene (POM). Either or both Inner tubing layer 13 and overmolded tube tip 14 may alternatively be comprised of carbon-fiber or steel-fiber materials that are interwoven with polymer materials, such as carbon-fiber PEEK™. Either or both inner tubing layer 13 and overmolded tube tip layer 14 may alternatively be comprised of a nano-composite material.

In one embodiment, actuator nut 2 is comprised of a metal, such as, for example, stainless steel. Those skilled in the art will appreciate that the actuator nut 2 may be comprised of other materials such as titanium, fused silica, or a reinforced rigid polymer material (e.g., a carbon-fiber PEEK™ or other metal-braided polymer material). More rigid polymer materials may be more desirable in some applications, since stainless steel has some drawbacks in biological environments. For example, components in a biological fluid can attach to stainless steel, and stainless steel ions may leak into said fluid—both events having the potential to obscure measurements in liquid chromatography and other analytic chemistry applications.

Figure 5:
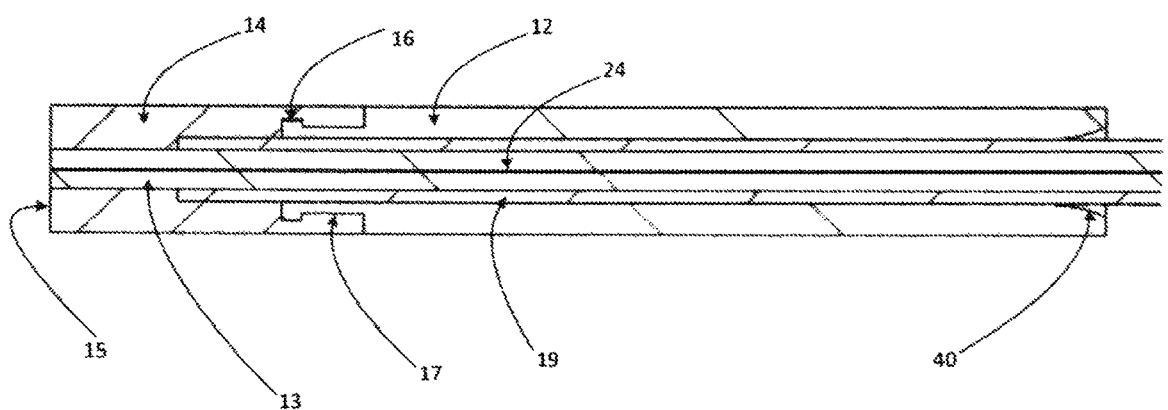
FIG. 5 is a detailed cross-sectional view a portion of the tubing of the fitting assembly in one embodiment.

FIG. 5 provides an enlarged view of the cross-section of the combination of the inner layer 13 of the tube, the outer layer 19 of the tubing, and the sleeve 12. In this embodiment, a passageway 24 extends along the longitudinal axis of the inner tubing layer 13 (and also outer tubing layer 19). A fluid or gas may be run through said passageway 24. In this embodiment, the tube has an end face or surface 15 which is substantially flat. However, those skilled in the art will appreciate the tube end face 15 may have other shapes, such as a rounded or dimpled surface (not shown). A flat or substantially flat surface 15 is believed to be sufficient for purposes of creating an effective seal with the port end face 26, but other shapes or configurations of end face 15 may be used so long as the surfaces of the tube end face 15 and the port end face 35 are adapted to form a seal when engaged with one another. Other such embodiments are discussed below in connection with FIGS. 6A, 6B, and 6C. In one embodiment, sleeve 12 is comprised of a metal, such as, for example, stainless steel. Those skilled in the art will appreciate that the sleeve 12 and/or outer tubing layer 19 may be comprised of steel or other materials such as titanium, fused silica, or a reinforced, rigid polymer material (e.g., carbon-fiber PEEK™, steel-braided TEFLON®). Particularly, rigid polymer materials may be more desirable in some applications, since stainless steel has some drawbacks in biological environments, as is described above.

Still referring to FIG. 5, additional features of the tubing assembly are shown in an enlarged cross-section view. Retention features 16 and 17, for example, are shown in more detail. As shown in FIG. 5, the retention feature 16 is a portion of sleeve 12 and is located at the end of the sleeve 12 which is closest to the face 15 defined by the end of the inner tube layer 13 and outer tube layer 14. Retention feature 16 is a protrusion or extension of sleeve 12 that provides a lip at the end of sleeve 12. As shown in FIG. 5, the outward edge of the lip 16 is located further from the longitudinal axis of the inner layer 13 than an adjacent portion 17 of the sleeve 12. The combination of features 16 and 17 help hold the outer layer 14 once attached to sleeve 12 and thus keep the combination of inner layer 13, outer layer 14, and sleeve 12 from being detached from one another.

Also shown in FIG. 5 is a recessed portion 40 of the sleeve 12 at the end opposite the location of the retention features 16 and 17. The recessed portion 40 can be a conically-shaped or parabollicaly shaped recess, such that the end of sleeve 12 with the recessed portion provides an opening with a diameter greater than that of the passageway through the sleeve 12. The recessed portion 40 thus makes it easier to insert an end of the combined inner layer 13 and outer layer 19 into the passageway through the sleeve 12 for easier and faster manufacturing of the tubing assembly comprising inner layer 13, outer layer 19, and the sleeve 12. In addition, the recessed portion 40 provides more flexibility to the tubing assembly once manufactured, because a user can more easily bend the portion of the inner layer 13 that extends out of the passageway of the sleeve 12 at the end opposite the end of the assembly at which surface 15 is located. As noted above, sleeve 12 and outer layer 19 can be secured together. In one embodiment, sleeve 12 comprises a metal (such as stainless steel), outer tubing layer 19 comprises a metal (such as stainless steel), and sleeve 12 and outer layer 19 are secured together by welding (or by crimping or swaging) at or near portion 40 of sleeve 12.

The tube tip 14 can be overmolded onto an end portion of the inner tubing layer 13, the outer tubing layer 19, and sleeve 12. For example, and as shown in FIG. 5, the inner tube 13 and outer tube 19 may be inserted through the passageway extending through the sleeve 12 so that the first ends of both the inner tube layer 13 and outer tube layer 19 extend a predetermined distance from the first end of the sleeve 12. The combination of the inner tube 13, outer tubing 19, and the sleeve 12 in this configuration can then have the outer tip 14 overmolded onto the combination, thereby forming the portion of the tubing assembly which comprises the inner layer 13 of the tube, the outer layer 19 of the tube, the sleeve 12, and overmolded tube tip 14. In one process for making this combination, the tube tip 14 is molded onto and over the inner layer 13, the outer layer 19, and the sleeve 12 by the process of injection molding. Those skilled in the art will appreciate that other processes may be used, such as casting and welding, and may be selected depending on the materials selected for the inner layer 13, the outer layer 19, and the tube tip 14. If desired, the surface 15 of the first end of the tubing as defined by the combination of the end of the inner layer 13 and the end of the tube tip 14 may be further finished, such as by cutting the first end of the tubing, polishing the first end of the tubing, or machining, with such processes performed to obtain a substantially flat surface 15 defined by the first ends of the inner layer 13 and the tube tip 14.

Figure 6A:
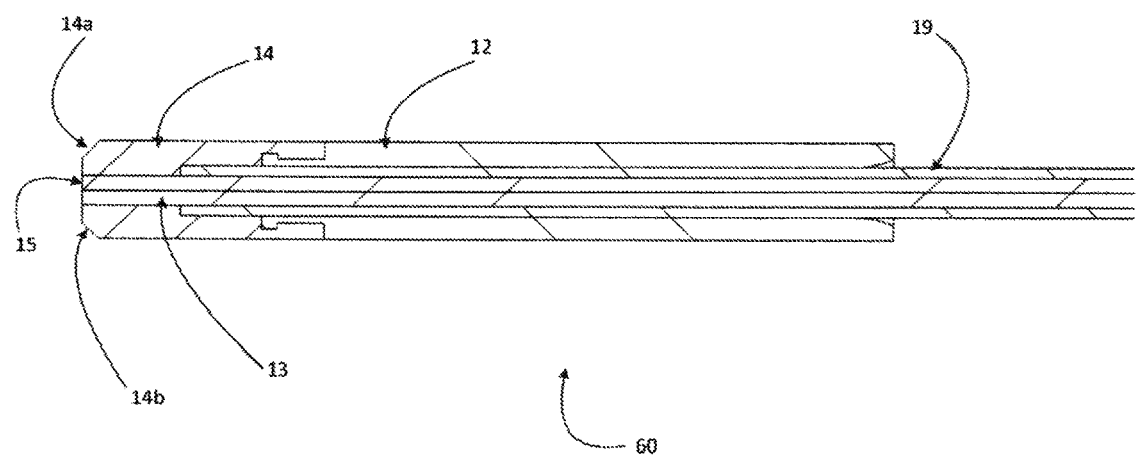
FIGS. 6A, 6B, and 6C are cross-sectional views of alternative embodiments of a tubing assembly in accordance with the present disclosure.
Figure 6B:
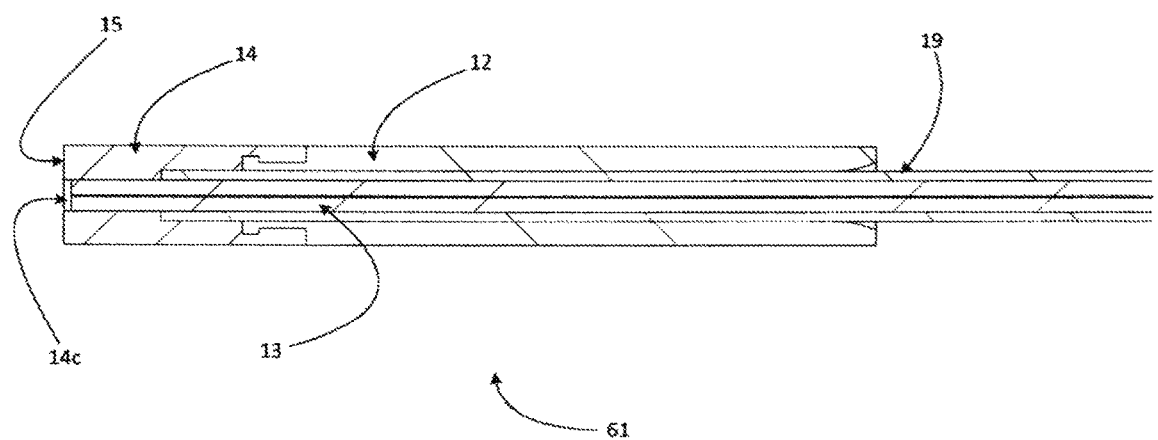
Figure 6C:
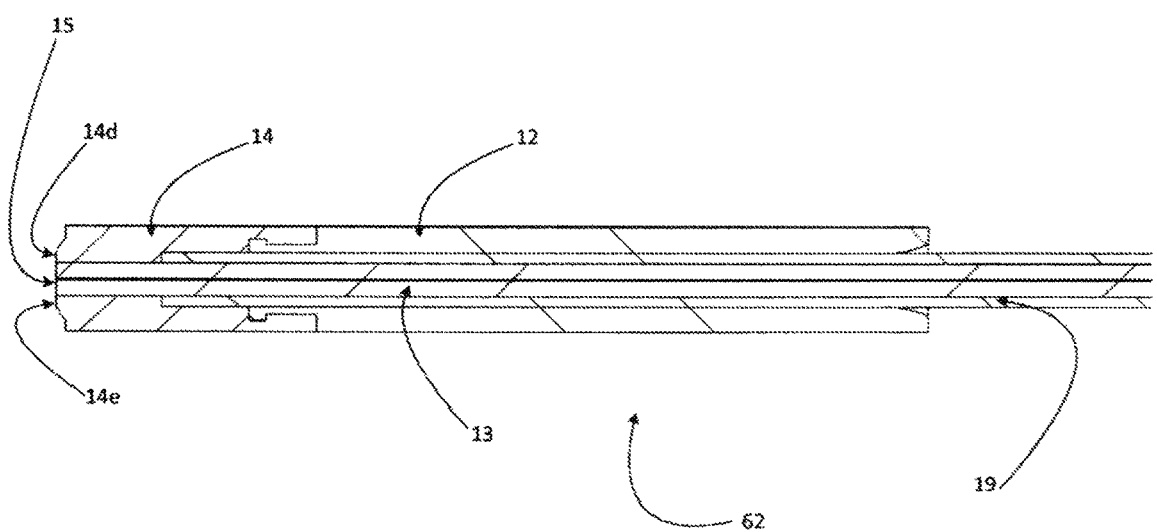

Referring now to FIGS. 6A, 6B, and 6C, alternative embodiments of a tubing assembly in accordance with the present disclosure are shown. Like numerals are used for the tip 14, inner tubing layer 13, sleeve 12, and outer tubing layer 19 in FIGS. 6A, 6B, and 6C for ease of reference. In FIG. 6A, a tubing assembly 60 is shown. The tubing assembly 60 includes an inner tubing layer 13, and outer tubing layer 19, a sleeve 12, and also a tubing tip 14. However, the tubing tip 14 in FIG. 6A has portions 14a and 14b which are angled from the outer diameter of the tip 14 towards the longitudinal axis of the tubing assembly 60. This configuration reduces the surface area of the surface 15 defined by the ends of the inner layer 13 and the tip 14 which is adapted to contact a face in a flat-bottomed port. It is believed that by reducing the surface area of the seal, we also are able to reduce the force required to obtain a seal.

Referring to FIG. 6B, a tubing assembly 61 includes an inner tubing layer 13, a sleeve 12, an outer tubing layer 19, and also a tip 14. As shown in FIG. 6B, the end of the inner tubing layer 13 is not flush with the end of the tip 14, thus leaving a gap 14c defined by the inner diameter of the tip 14. In the tubing assembly 61 of FIG. 6B, the surface 15 at one end of the tubing assembly 61 that is adapted to contact a surface in a flat-bottomed port is defined by the surface at the end of the tip 14 and not the end of the inner tubing layer 13. This configuration also reduces the surface area of the tubing assembly which is adapted to contact and seal with a flat-bottomed port.

Referring now to FIG. 6C, another embodiment is shown. In FIG. 6C, the tubing assembly 62 includes an inner tubing layer 13, a sleeve 12, an outer tubing layer 19, and a tip portion 14. The end of the tip portion 14 has portions 14d and 14e which include a "stepped" shape in which an outer portion extends towards the longitudinal axis of the tubing assembly 62 and then an angled portion extends from the step portion towards the end of the tip 14 and towards the longitudinal axis of the tubing assembly 62. This embodiment also helps reduce the surface area of the surface 15 defined by the combination of the end of the inner tubing layer 13 and the inner portion of the end of the tip 14 defined by the stepped end portions 14d and 14e.

Those skilled in the art will appreciate that other configurations besides those illustrated and described in this disclosure can be used in various applications of the tubing and fitting assemblies in accordance with the present disclosure. It will also be appreciated that the materials described above which can be used for the various features and components of the fitting and tubing assemblies of the present disclosure can likewise be used for the same or similar features and components of the tubing assemblies illustrated in FIGS. 6A, 6B, and 6C.

Figure 7A:
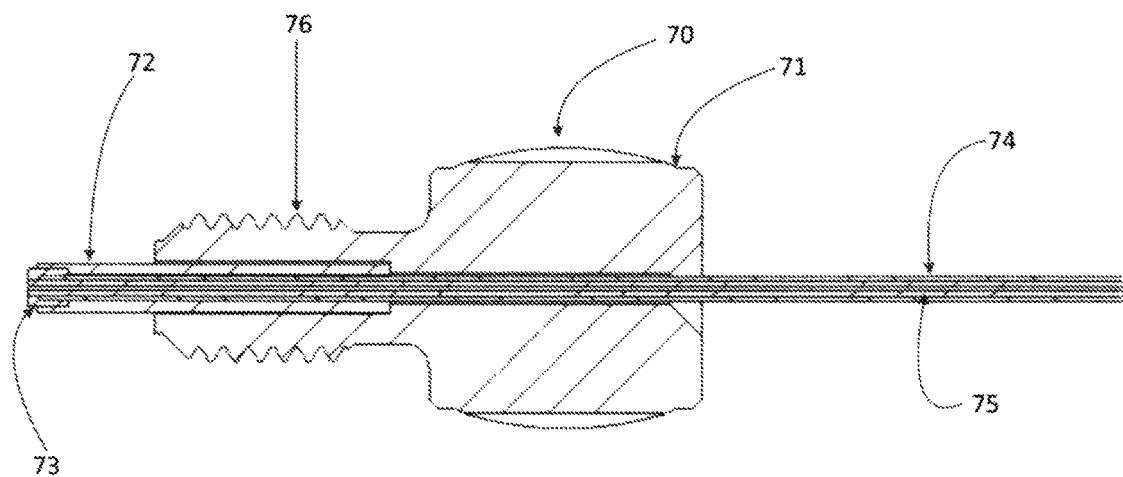
FIG. 7A is a cross-sectional view of a polymer-lined face sealing connection with an internal tip.
Figure 7B:
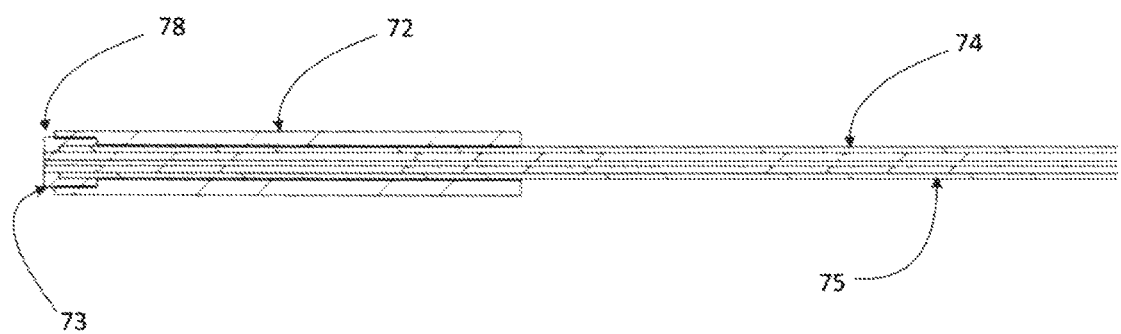
FIG. 7B is a detailed view of the embodiment of FIG. 7A.
Figure 7C:
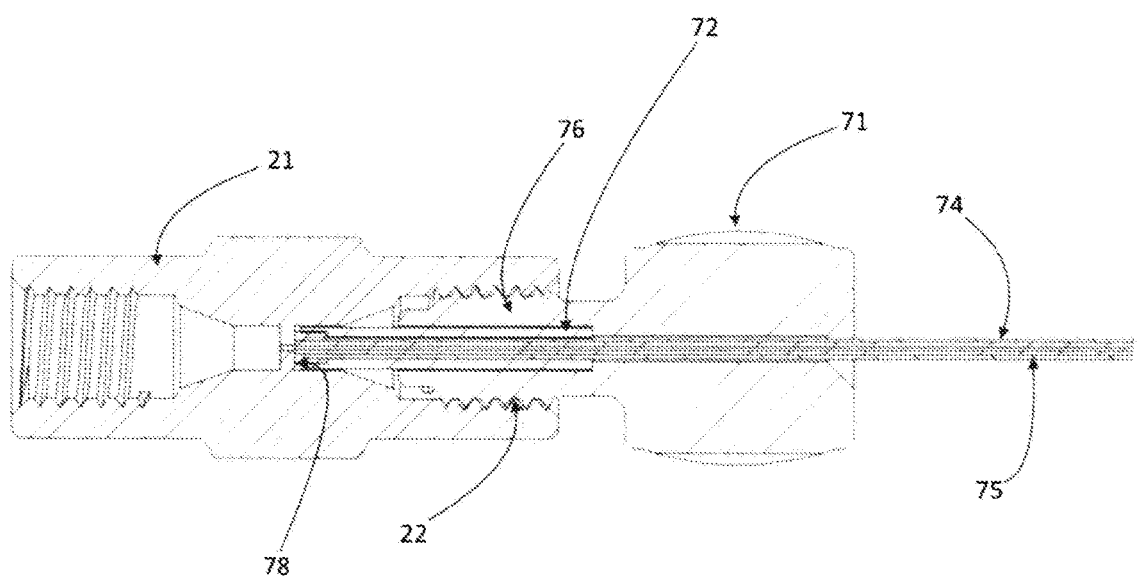
FIG. 7C is a view of a face sealing connection connected with a housing body.

A further embodiment is shown in FIGS. 7A-C. The embodiment 70 of FIG. 7A also includes an actuator nut 70, comprising a head portion 71 at a first end thereof and a threaded portion 76 near a second end thereof, wherein the an external threaded portion 76 is configured to interact with an internally threaded connection 22, in a housing 21, best shown in FIG. 7C. The nut defines a passageway therethrough sized and shaped to contain a liner tubing 75 and a reinforcement tubing 74, wherein the liner tubing 75 can be concentrically contained with the reinforcement tubing 74. A portion of the passageway proximate and at least partially contained with the externally threaded portion 76 is also sized to contain a transfer tubing 72. In the embodiment shown in FIG. 7C, the reinforcement tubing 74, the liner tubing 75 and the transfer tubing 72 extend out of the passageway through the second end of the nut 71 and terminate at tube end face 78. The transfer tubing 72 can be secured to the reinforcement tubing 74 by swaging or crimping onto the tubing with mechanical force radially or by any appropriate means known to those skilled in the art that allows for axial forces resulting from the fluid pressure reacted through the transfer tubing 72 and reinforcement tubing 74, such as welding, for example. This configuration (shown in FIG. 7D) allows the tip 73 to be compressed between the reinforcement tubing 74 and a port bottom, which aids in creating a fluidic seal and prevents dead volume. The liner tubing 75 can be secured in the reinforcement tubing by an interference fit formed by feeding liner tubing 75 with an outer diameter greater than the internal diameter of reinforcement tubing 72 through the reinforcement tubing 72, thereby providing a tight interference fit, or such as by feeding liner tubing 75 through reinforcement tubing 75 and then either increasing the outer diameter of the liner tubing 75 or decreasing the inner diameter of the reinforcement tubing 72, or by other means known to those skilled in the art.

As further shown in FIG. 7A, the device further comprises a tip 73. As shown, the reinforcement tubing 74, the liner tubing 75 and the transfer tubing 72 extend out the second end of the nut 71 and terminate in a tube end face 78, in proximity to each other at a distance from the second end of the nut, configured to extend into a housing 21 through and past an internally threaded portion as described above. The tip 73 is disposed at the terminal end and is positioned to contact a face of a port extended into the housing 21 as shown in FIG. 7C.

During use, the nut 71 is reversibly connected to the housing by threading the external threads into a housing and reversibly connecting a port to the opposite end of the housing, a face seal is established between the tip and the bottom of the port without the use of ferrules to grip the tubing. The fitting assembly nut 71 drives against the bearing surface of the transfer tubing 72 to push the sealing surface of the tip 73 into and against the port bottom. The tip seal to the liner tubing 75 is created by an interference fit created by the internal diameter of the tip being smaller than the outside diameter of the tubing that requires the liner tubing 75 to be drawn into the tip 73. The tip 73 can be slid into position against the reinforcement tubing 74. The transfer tubing 72 is slid over the outside of the tip 73 and crimped into place by means known to those skilled in the art including, for example, the presence of angled surfaces that interact to create a taper lock interference fit. In the embodiment described and shown in FIGS. 7A-C, there are not any angles on the tip 73, transfer tubing 72, reinforcement tubing 74, or liner tubing 75. The assembly instead uses the interference between the components to retain the integrity of the seal and connection system. The reinforcement tubing 74 and transfer tubing 72 can be metal, selected from but not limited to stainless steel, steel, or titanium. The tip 73 and liner tubing 75 can be made of softer materials, including polymers such as PEEK, carbon filled PAEK, PEEK, PEKK, FEP, PFA, ETFE, or PTFE, for example. The nut 71 can comprise either one or more metals such as stainless steel, aluminum, titanium, or nickel, for example, or one or more polymers as appropriate for the intended use in particular systems, and with particular fluids.

A closer view of the fitting including the tubing and passageway is shown in FIG. 7B. As can be seen in the figure, the liner tubing and reinforcement tubing are drawn into the interior diameter of the tip to provide an interference fit. The transfer tubing can then be slid over the outside of the tip and in place, or held in place by other appropriate methods known in the art. The fitting is shown as it interacts with a housing body 21 for connection to a port. As shown in the figure, the tubing end face 78 extends through the threaded portion 76 and into the housing body past the mated threaded portions 76 and 22. The terminal end face can thus be pressed against a port end face to create a seal.

Figure 7D:
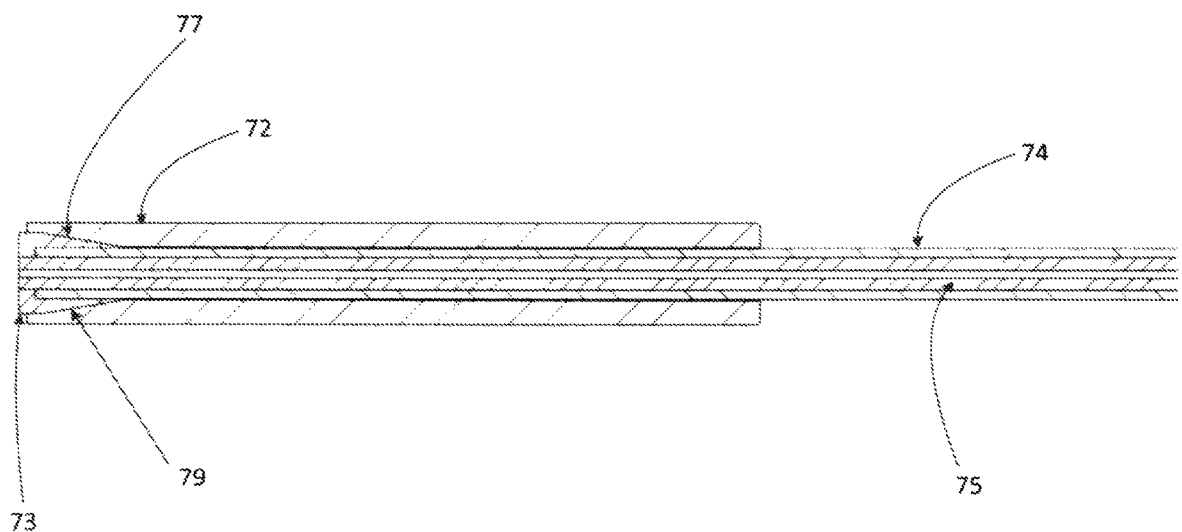
FIG. 7D is a detailed cross-sectional view of an embodiment of a fitting assembly with an internal tip.

An alternate embodiment of the fitting of FIG. 7A-C is shown in FIG. 7D. As shown in the figures, the second end of the transfer tubing 72 includes an angled internal face portion 77 and the tip 73 includes an oppositely angled outer face portion 79 to facilitate easier insertion of the tip 73 into the transfer tubing 72 by a user.

Figure 8A:
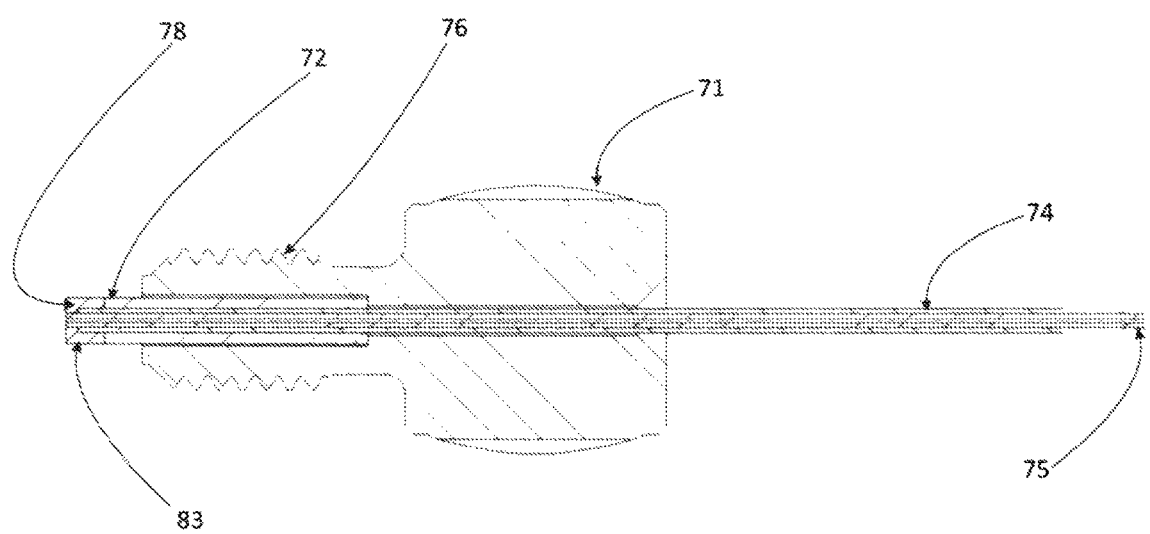
FIG. 8A is a cross-sectional view of a polymer-lined face sealing connection with an external tip.
Figure 8B:
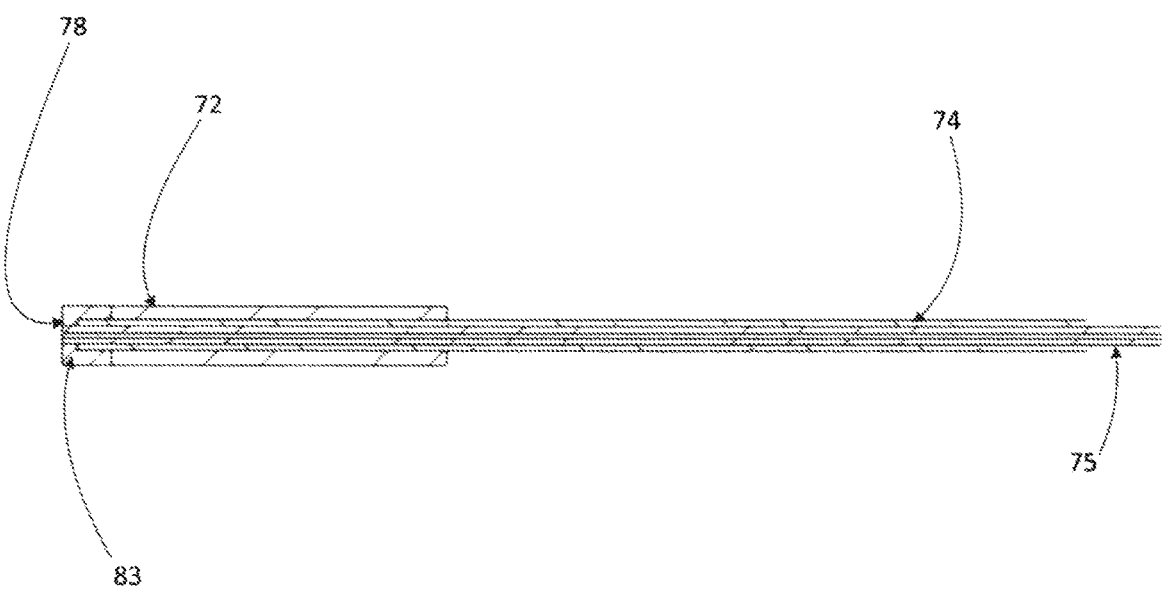
FIG. 8B is a detailed view of the embodiment of FIG. 8A.
Figure 8C:
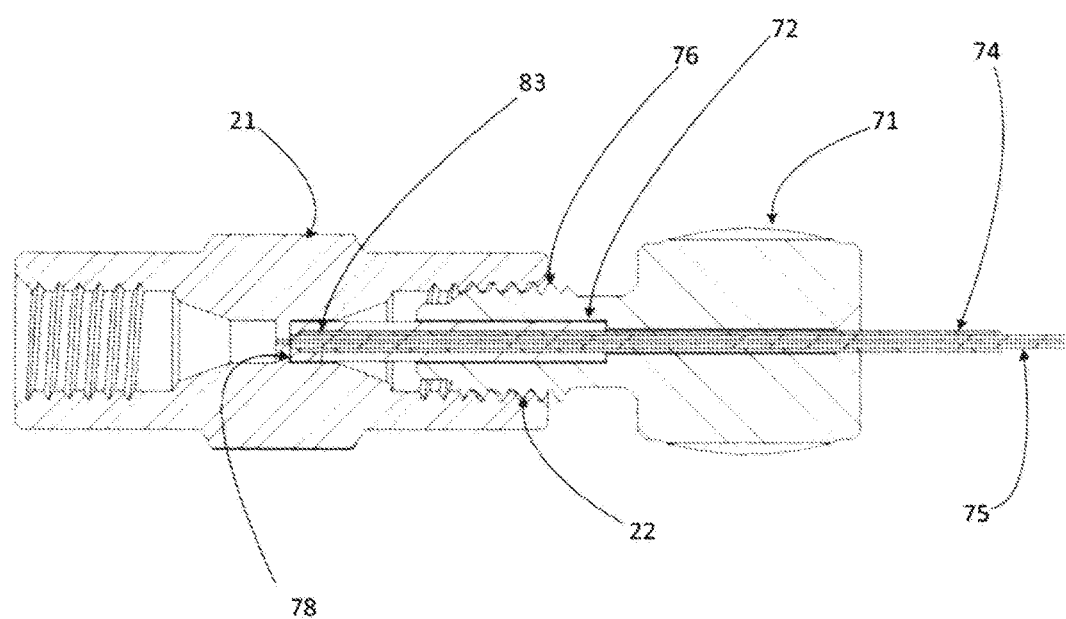
FIG. 8C is a view of a face sealing connection connected with a housing body.

An embodiment including an alternate tip 83 is shown in FIGS. 8A-C. In this embodiment, all common items are numbered the same as in the embodiment shown in FIGS. 7A-C. The tip 83 shown in FIGS. 8A-C, however, is no longer captured by the transfer tubing 72 with an interference fit. This embodiment instead uses the transfer tubing 72 to drive against the tip 83 during assembly to create a face seal on a sealing surface in a port and the surfaces contacting the transfer tubing 72. The tip 83 is drawn onto the tubing and utilizes an interference fit to create a seal between the liner tubing 75 and tip 83. All of the components of the embodiment of FIGS. 8A-C can be manufactured from the same materials as the embodiment shown in FIGS. 7A-C.

An enlarged view of the embodiment of FIG. 8A is shown in FIG. 8B. In this view it is shown that the transfer tubing 72 is shortened from the tube face end 78 such that the tip abuts the terminal end of the transfer tube 72, while the liner tube 74 and reinforcement tube 75 are contained in the inner diameter of the tip 83. A view of a fitting as described in FIG. 8A connected to a housing body 21 is shown in FIG. 8C. As describe above, when the nut is driven into the housing, the tip 83 at the tube face 78 is forced against a port face by the transfer tubing 72 to create a face seal.

Figure 9A:
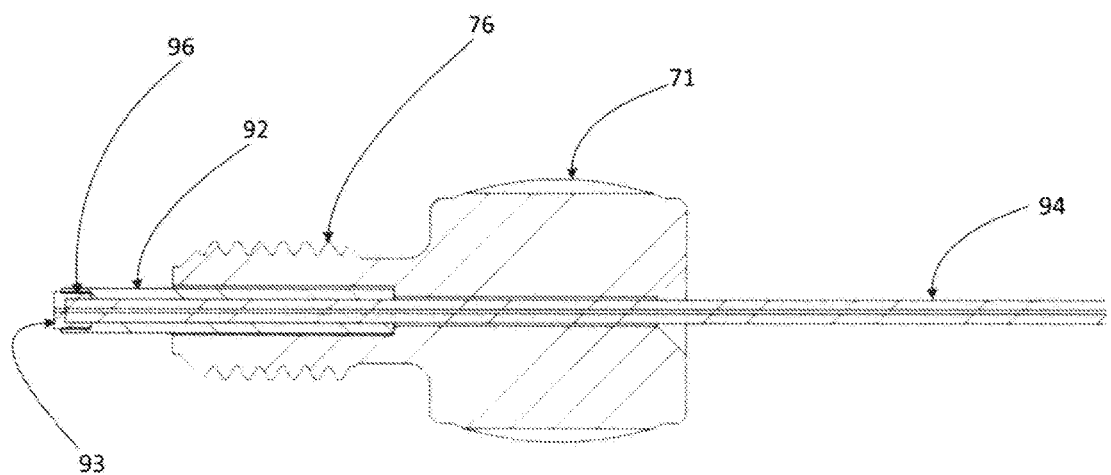
FIG. 9A is a cross-sectional view of another embodiment of a polymer lined face sealing connection.
Figure 9B:
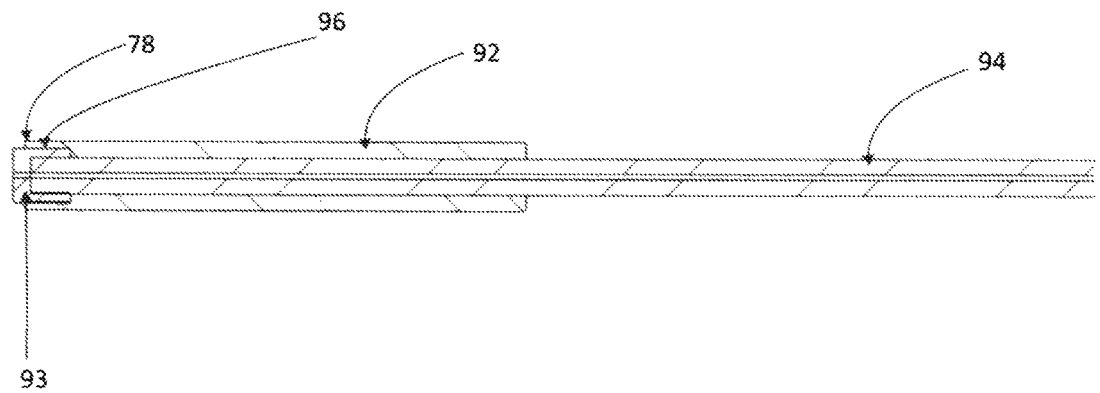
FIG. 9B is a detailed view of the embodiment of FIG. 9B.
Figure 9C:
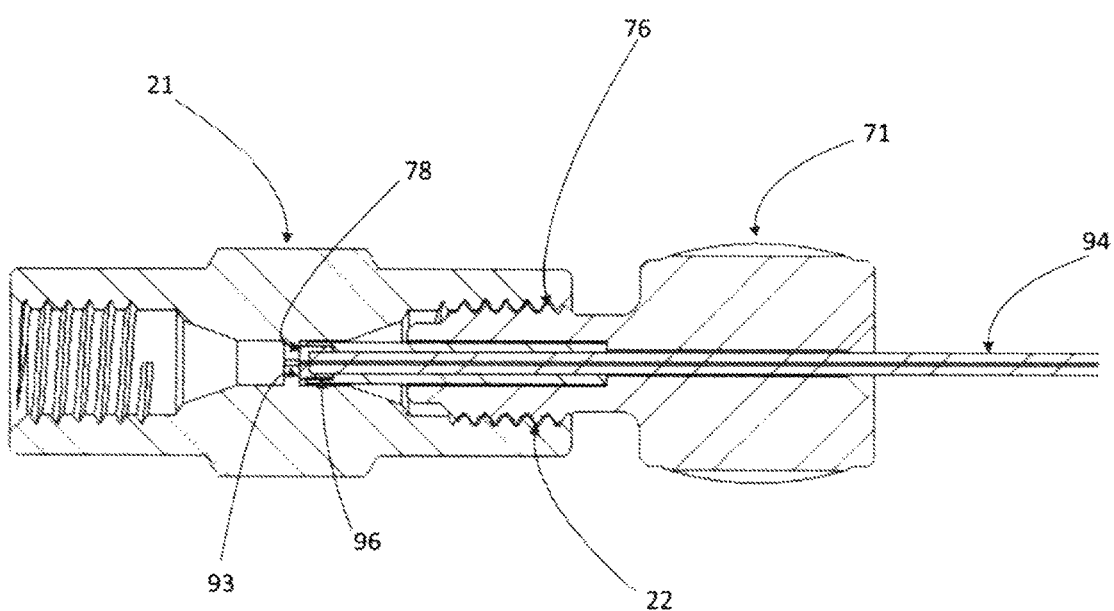
FIG. 9C is a view of a face sealing connection connected with a housing body.

Another embodiment of a connection assembly is shown in FIGS. 9A-C. This embodiment does not include a liner tubing. The embodiment uses the sealing of the tip 93 in a port bottom along with sealing of the tip 93 to a conduit tubing 94. The transfer tubing 92 translates the load from the rotational torque of the nut when applied by an operator to both sealing areas of the tip 93. The transfer tubing 92 in this embodiment can be made of a more durable or less resilient material such as a metal material, with stainless steel being an exemplary material, and the transfer tubing includes a pocket portion 96. There is interference between the outside diameter of the tip 93 and the pocket portion 96 in the transfer tubing 92. The interference is effective to retain the tip 93 on the conduit tubing 94 during assembly and disassembly. In addition, the face of the tip is effective to form a seal with a port sealing face as shown in FIG. 9C. The use of a stainless steel transfer tubing 92 allows for the use of higher pressures. Pressures in excess of 15,000, 20,000, and 25,000 psi have been achieved in test samples of this embodiment without leaking. The conduit tubing 94 and transfer tubing 92 can be manufactured from and comprise stainless steel tubing, for example, or can be made from other metals as known to those skilled in the art. The tip 93 can include one or more polymers such as PEEK, carbon fiber reinforced PEEK, PEKK, FEP, PFA, ETFE, or PTFE, for example. The fitting can be either a metal such as stainless steel, aluminum, or titanium, for example, or one or more polymers depending on system requirements. An enlarged view of the tubing as shown in FIG. 9A is shown in FIG. 9B, in which the tip 93 can be seen extending into the pocket portion 96 effective to be held against the conduit tubing 94 and forming a tube face end effective to form a face seal with a port seal face as shown in FIG. 9C.

Additional embodiments of the disclosed connection assemblies that can be used to form a face seal with various flat bottomed ports or fixtures as required and that do not include a liner tubing are shown in FIGS. 10-13. The connector assembly shown in FIG. 10 includes a transfer tubing 92 surrounding the conduit tubing 94 as in the embodiment shown in FIG. 9A. There is again interference in this embodiment between the outside diameter of the tip 93 and the pocket portion 96 and the transfer tubing 92. It can be seen in this embodiment that the end face 98 of the transfer tube is flush with the end face 99 of the conduit tubing 94.

Figure 11:
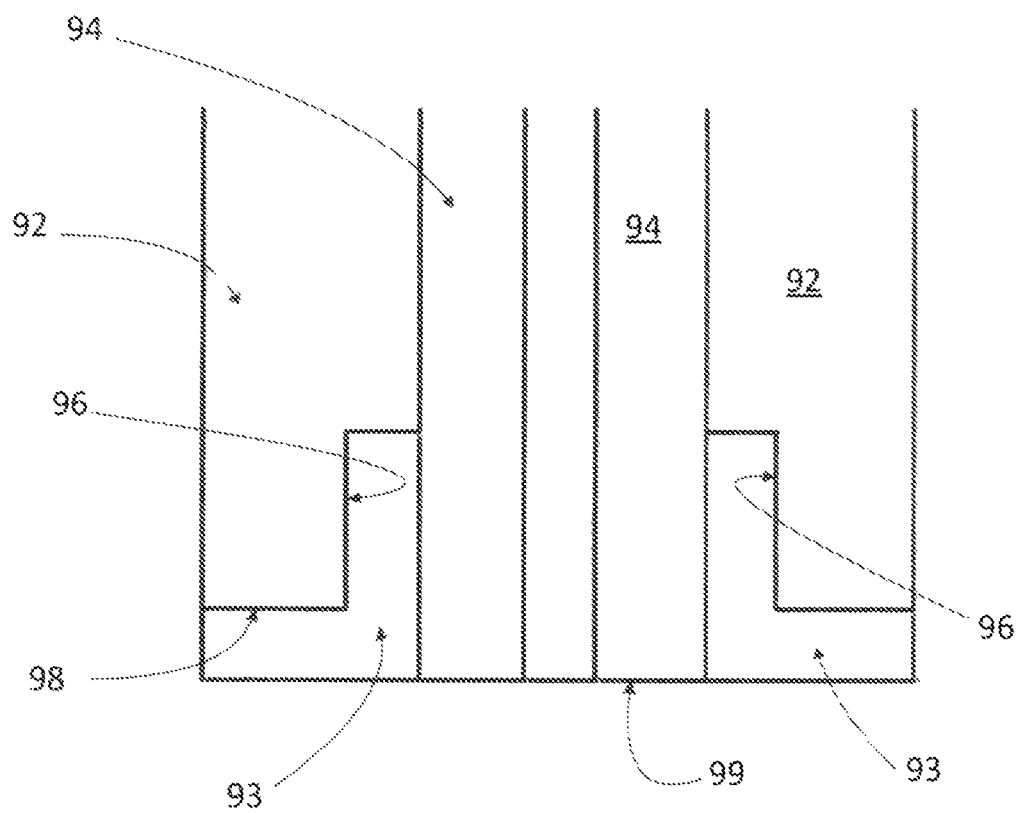
FIG. 11 is an enlarged cross-sectional view of an end of one particular embodiment of an assembly according to the present disclosure.
Figure 12:
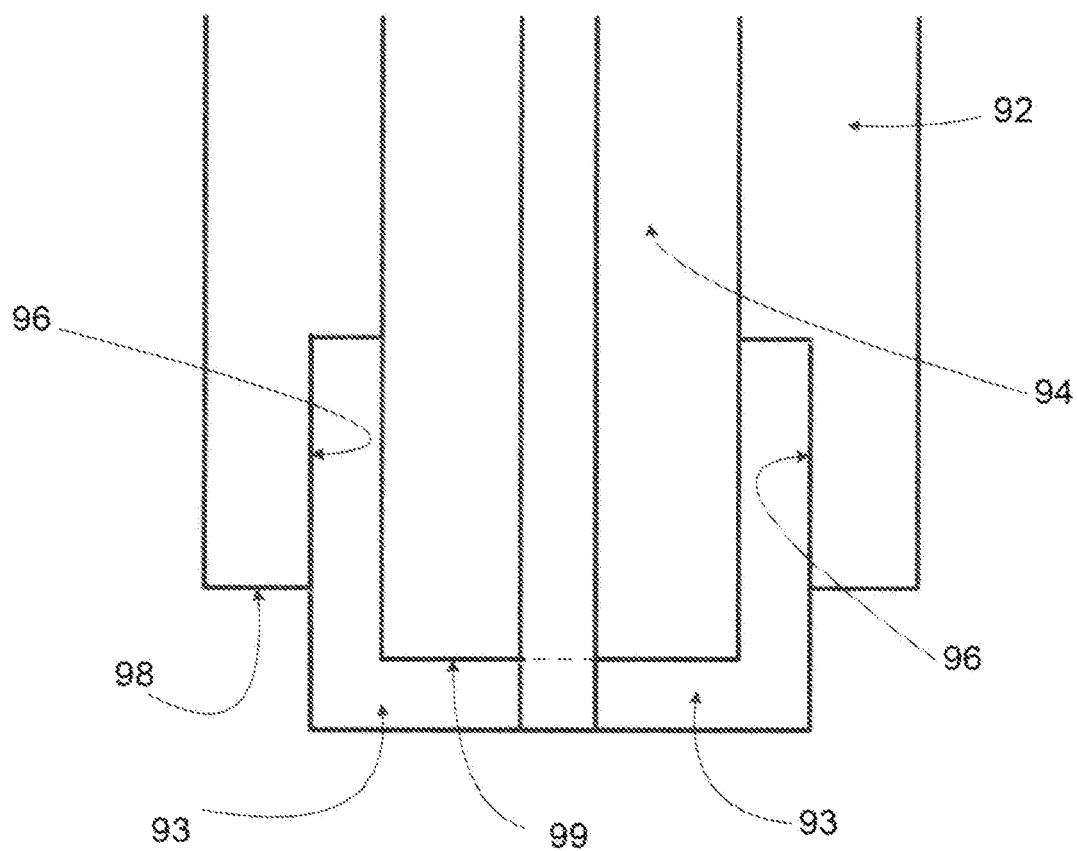
FIG. 12 is an enlarged cross-sectional view of an end of one particular embodiment of an assembly according to the present disclosure.

An additional embodiment is shown in FIG. 11 in which the end face 99 of the conduit tubing 94 extends beyond the end face 98 of the transfer tubing 92. The pocket portion 96 and the tip in this embodiment extend from the inner diameter to the outer diameter of the conduit tubing 94 and is not disposed between the end of the conduit tubing and the port (not shown). A further embodiment is shown in FIG. 12 in which the end face 99 of the conduit tubing 94 extends even further out of the transfer tubing 92. Such connection assemblies are shown to indicate that the disclosed embodiments can be altered or configured to effectively seal with a variety of connectors or ports as needed, or to provide an effective seal at various pressures and volumes.

Figure 10:
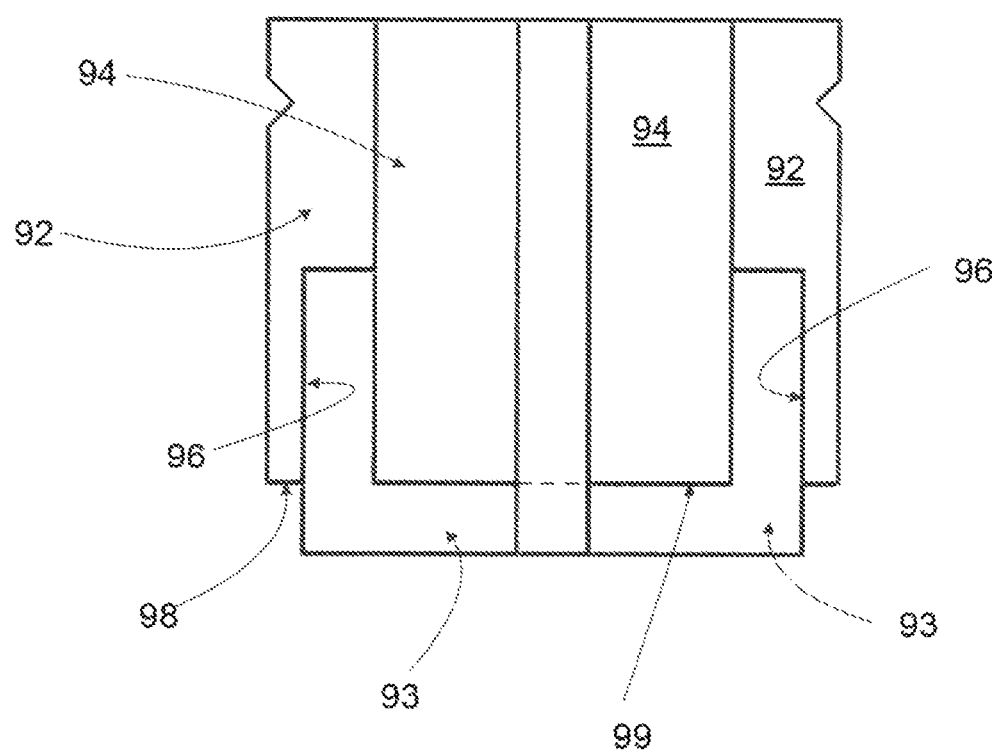
FIG. 10 is an enlarged cross-sectional view of an end of one particular embodiment of an assembly according to the present disclosure.

As described for FIG. 9, the embodiments shown in FIGS. 10-12 do not include a liner tubing. The embodiments use the sealing of the tip 93 in a port bottom along with sealing of the tip 93 to a conduit tubing 94. The transfer tubing 92 translates the load from the rotational torque of the nut when applied by an operator to both sealing areas of the tip 93. The transfer tubing 92 in these embodiments can be made of a more durable or less resilient material such as a metal material, with stainless steel being an exemplary material, and the transfer tubing includes a pocket portion 96. There is interference between the outside diameter of the tip 93 and the pocket portion 96 in the transfer tubing 92. The interference is effective to retain the tip 93 on the conduit tubing 94 during assembly and disassembly. In addition, the face of the tip is effective to form a seal with a port sealing face. The use of a stainless steel transfer tubing 92 allows for the use of higher pressures. The conduit tubing 94 and transfer tubing 92 can be manufactured from and comprise stainless steel tubing, for example, or can be made from other metals as known to those skilled in the art. The tip 93 can include one or more polymers such as PEEK, carbon fiber reinforced PEEK, PEKK, FEP, PFA, ETFE, PEEKsil, or PTFE, for example. Alternatively, the conduit tubing 94 can be a capillary tube, such as a capillary made of silica, fused glass, PEEKsil (fused silica with a sheath of polyetheretherketone), the transfer tubing 94 can be made of a polymer such as one or more of those noted above, and/or the tip 93 can be made of metal, such as stainless steel. The fitting can be either a metal such as stainless steel, aluminum, or titanium, for example, or one or more polymers depending on system requirements.

Figure 13:
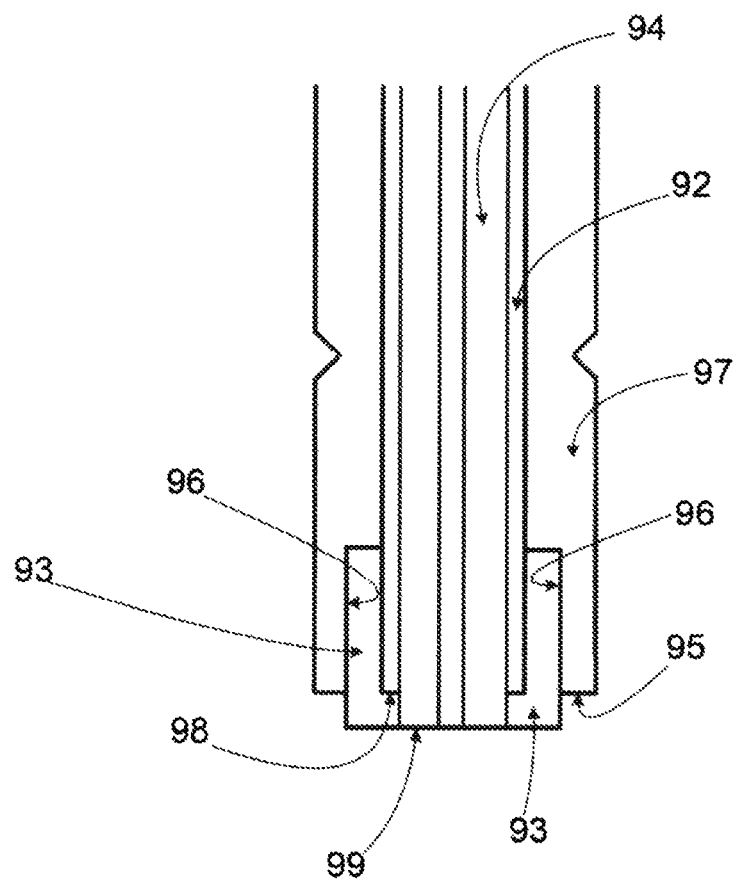
FIG. 13 is an enlarged cross-sectional view of an end of one particular embodiment of an assembly according to the present disclosure.

Referring now to FIG. 13, yet another alternative embodiment of the present disclosure is provided. FIG. 13 is an enlarged cross-sectional view of an end of the assembly. In FIG. 13, an assembly is shown which includes conduit tubing 94, transfer tubing 92, and a tip 93. In addition, the assembly includes a sleeve 97. As shown in FIG. 13, the sleeve 97 includes pockets 96 in which a portion of the tip 93 is located. In this particular embodiment, the end face 99 of conduit tubing 94 is flush with an end face of the tip 93, and the end faces of tip 93 and conduit tubing 94 are adapted to abut a port (not shown in FIG. 13). As also shown in FIG. 13, in this particular embodiment, an end face 95 of the sleeve 97 is flush with the end face 98 of the transfer tubing 92. Those skilled in the art will appreciate that the transfer tubing 92, conduit tubing 94, sleeve 97, and tip 93 can each be made of various materials, including those noted above for the embodiments shown in FIGS. 10-12, including polymeric, metal, and ceramic materials, and may be varied depending on the intended application of the assembly, such as the pressures involved, the solvents and fluids involved, and the like.

Figure 14:
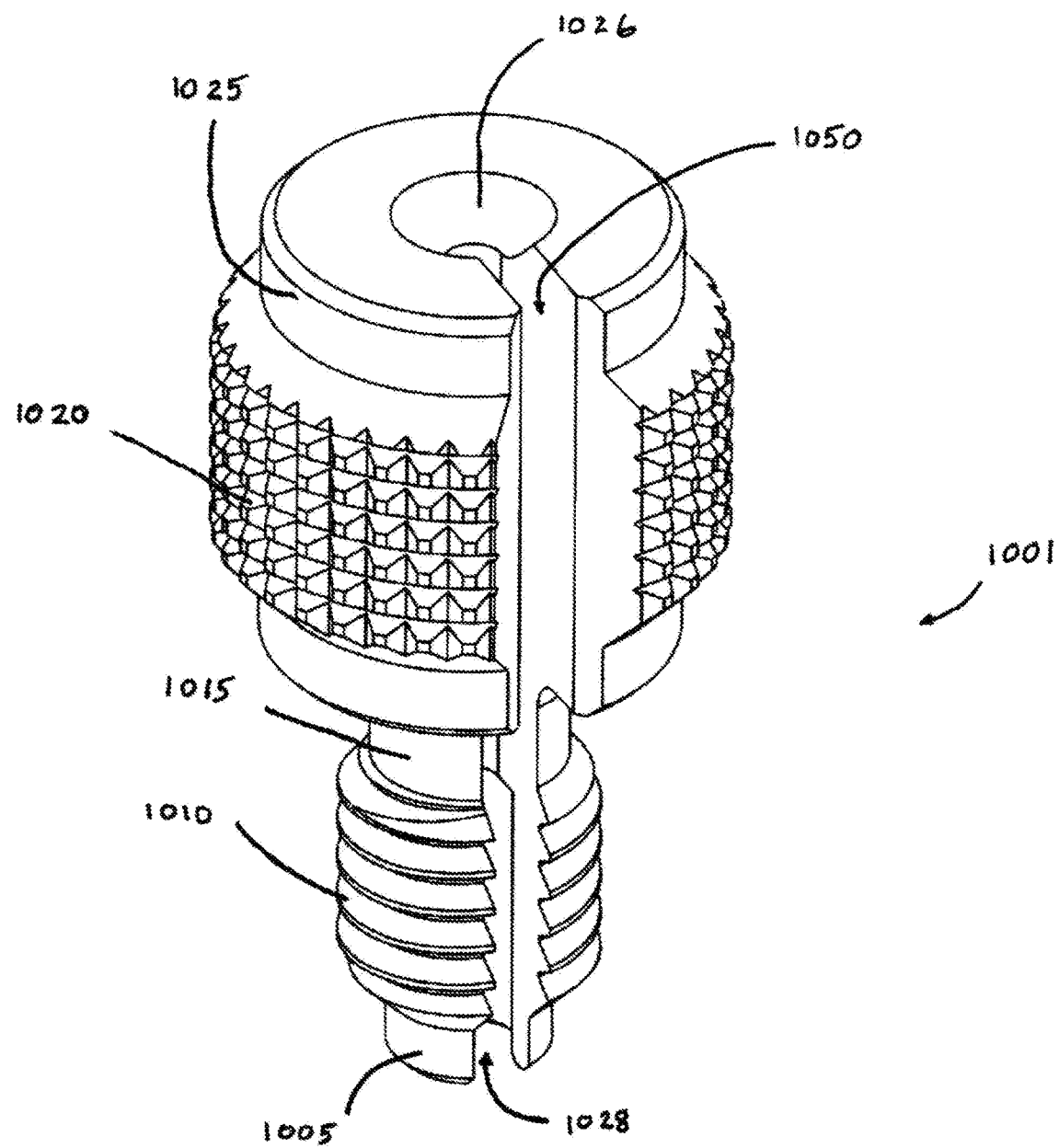
FIG. 14 is an isometric view of an alternative nut which can be used in embodiments of the present disclosure.

In FIG. 14, an alternative nut 1001 is shown. The nut 1001 can be used in any of the foregoing embodiments. As shown in FIG. 10, the nut 1001 has a first end portion 1005, as well as an externally threaded portion 1010, a lower portion 1015, a knurled portion 1020, and a top portion 1025 at the second end of the nut 1001. The nut 1001 has openings 1026 and 1028 at its top and bottom (or second and first) ends, respectively. The openings 1026 and 1028 are open to a passageway 1030 (shown in FIGS. 15 and 16) extending longitudinally through the nut 1001. The nut 1001 also has a slotted, grooved or split portion 1050. As shown in FIG. 10, the slot or groove 1050 extends the longitudinal length of the nut 1001. Radially, the groove 1050 also extends from the outer surface of the nut 1001 to the passageway 1030 (not shown in FIG. 14) extending along the longitudinal axis of the nut 1001.

The groove or slot 1050 of the nut 1001 provides an advantage because it allows an operator to route a tube (such as described above in various embodiments) through an analytical instrument system and/or its various components, then add the nut 1001 to make up a connection with the fitting assembly after the tube is roughly in place. In a number of applications, the space for the various components can be limited and fairly tight, and in such situations having the nut captivated on the tube assembly can make it difficult to route the assembly to the proper location to make up a connection. Because tubes periodically need to be replaced in AI systems, having the slot 1050 on the nut 1001 allows for easier location and for easier and faster replacement of tubing in many situations. This approach also makes it easier and more common for reuse of the nut 1001, since the nut 1001 need not be attached to the tubing. The groove 1050 also may allow for easier use of the nut 1001 when the nut 1001 is rotated in engagement with a port, such as a port in an LC, HPLC, UHPLC, or other AI system, or other component, such as in such a system (which could be a union, pump, column, filter, guard column, injection valve or other valve, detector, pressure regulator, reservoir, or another fitting, such as a tee, cross, adapter, splitter, sample loop, connector, or the like) to make a fluidic connection, such as when used in connection with the embodiments of this disclosure described above. Those skilled in the art will appreciate that, in an alternative embodiment, the nut 1001 could have an internally threaded portion (not shown) adapted to engage with an externally threaded portion of a port or other component such as those listed, or could be otherwise configured to provide axial loading. For example, axial loading could be provided by hydraulic actuators, spring-loaded connections, by hand by an operator or user, a solenoid, and so forth.

The nut 1001 can be made of a metal, such as, for example, stainless steel. Those skilled in the art will appreciate that the nut 1001 may be comprised of other materials such as titanium, fused silica, or a reinforced rigid polymer material (e.g., a carbon-fiber PEEK™ or other metal-braided polymer material). More rigid polymer materials may be more desirable in some applications, since stainless steel has some drawbacks in biological environments. For example, components in a biological fluid can attach to stainless steel, and stainless steel ions may leak into said fluid—both events having the potential to obscure measurements in liquid chromatography and other analytic chemistry applications. The nut 1001 thus can comprise biocompatible materials, such as polyetheretherketone (PEEK), which are generally inert with respect to biological materials. Those skilled in the art will appreciate that the slot 1050 of the nut 1001 need not run the entire longitudinal length of the nut 1001. In addition, a plurality of slots can be provided instead of a single slot 1050. For example, the nut 1001 could have a top slot at the top end 1025 of the nut 1001 and also a bottom slot at the bottom end 1005 of the nut 1001.

Figure 15:
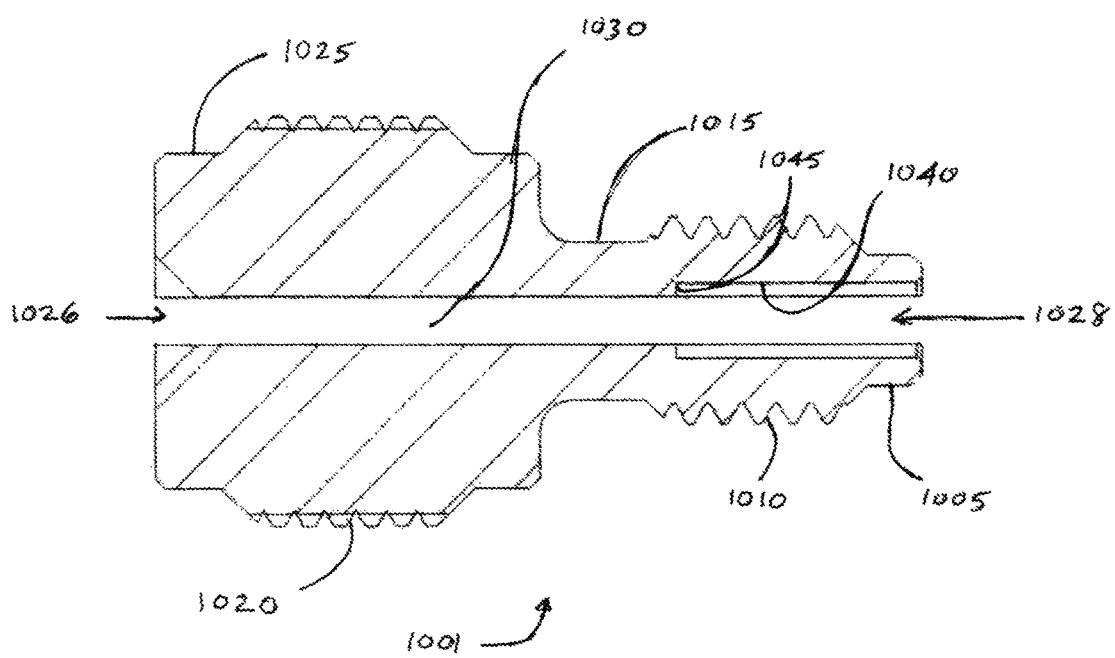
FIG. 15 is a cross-sectional view of the alternative nut of FIG. 10 and can be used in embodiments of the present disclosure.

Referring now to FIG. 15, a cross-sectional view of the nut 1001 is shown. Like features in FIGS. 14-16 have the same numerals for ease of reference. As shown in FIG. 15, the nut 1001 has a passageway 1030 extending through the nut 1001 generally along the longitudinal axis of the nut 1001. The first end portion 1005, externally threaded portion 1010, lower portion 105, knurled portion 1020, and second end 1025 correspond to those portions as shown in FIG. 14. As also shown in FIG. 15, the nut 1001 has an interior seating portion 1040 proximate towards the first end 1005 of the nut 1001, with the interior seating portion 1040 open to opening 1028. The interior seating portion 1040 is adapted to receive and removably hold a tube assembly comprising a tube and a liner sleeve, transfer tube, or other sleeve (not shown in FIG. 15) in place. For example, any of the sleeves described above, including without limitation the sleeve 12 or sleeve 92, can be adapted to fit within the interior seating portion 1040 of the nut 1001. Moreover, the interior seating portion 1040 at one end has an end portion 1045. As shown in FIG. 15, the interior seating portion 1040 has a wider diameter than that of other portions of the passageway 1030 in the nut 1001. The end portion 1045 provides a seat at one end of the interior seating portion 1040. When assembled, the seat at the end portion 1045 of nut 1001 allows a compressive force to be applied by the end portion 1045 against a sleeve held within the interior seating portion 1040 of the nut 1001, such as when the nut 1001 is rotated relative to a port or other component to make up a fluidic connection or fitting assembly, such as described above with respect to other embodiments, thereby transferring the compressive force to the end of the tube assembly as it abuts a face in a port or other component.

Figure 16:
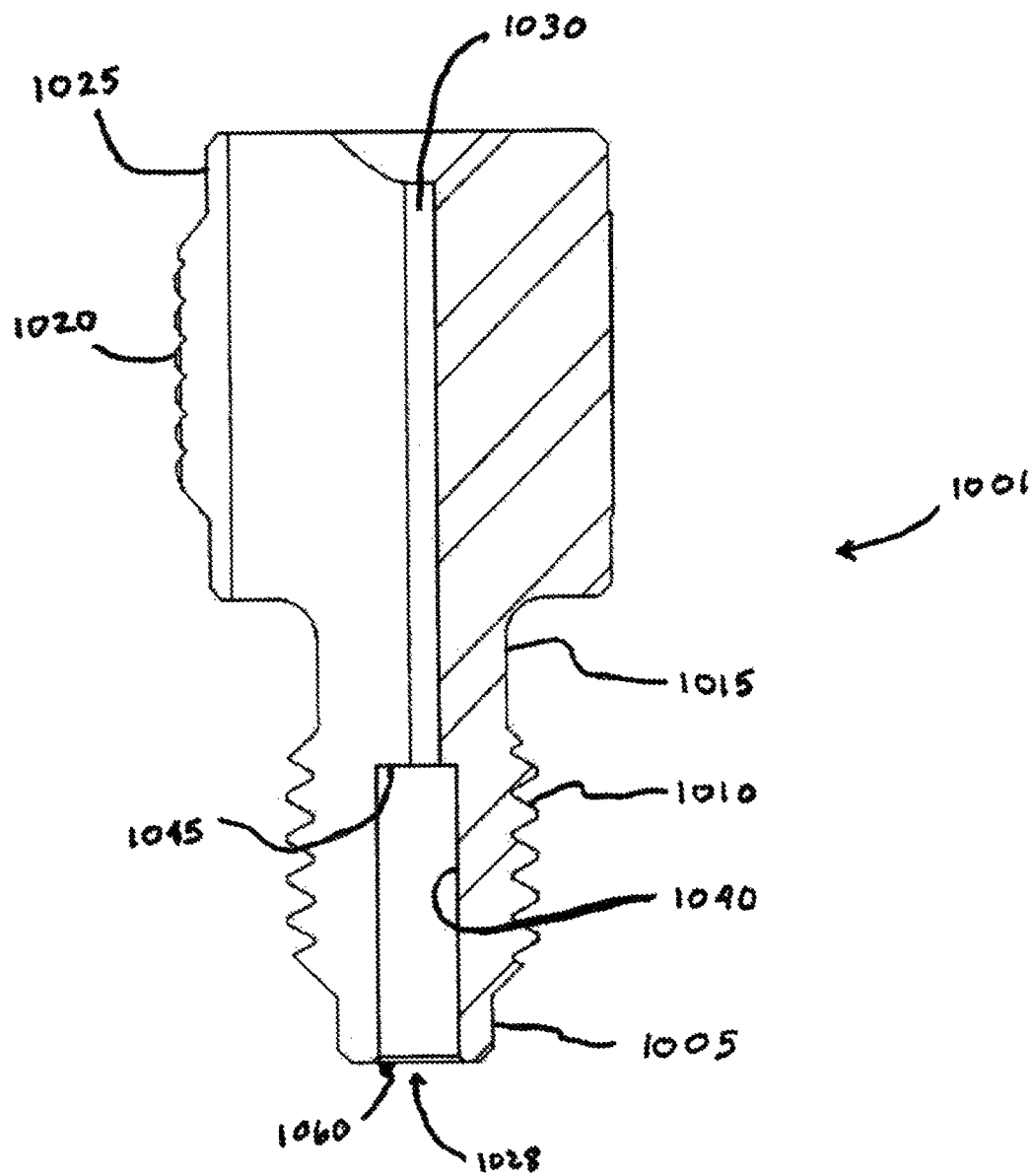
FIG. 16 is a second cross-sectional view of the alternative nut of FIGS. 10 and 11 and can be used in embodiments of the present disclosure.

Now referring to FIG. 16, a different cross-sectional view of the nut 1001 is provided. As with FIG. 15, the numbering in FIG. 16 uses like numerals to refer to the same features as shown in FIGS. 14 and 15 for convenience. The longitudinal extension along the length of the nut 1001 of the slot 1050 (not labelled in FIG. 16), as well as its radial extension from the passageway 1030 to the exterior surface of the nut 1001, becomes apparent with a comparison of FIGS. 15 and 16. Also shown in FIG. 16 is a flared portion 1060 located at the first end of the nut 1001. The portion 1060 provides an opening 1028 with a wider diameter than the interior seating portion 1040, thus allowing a user to more easily and quickly insert a tubing assembly (such as a combination comprising a tube and a sleeve as described above) into the nut 1001.

It will be appreciated that, as noted below, the tubing, and also the components of a fitting assembly or connection system, used in many analytical instrument systems for fluidic connections can be very small. Moreover, the components used in many analytical instrument systems can vary, and often need to be changed or replaced, such as replacing columns, pumps, injection valves, and so forth, whether when switching from one particular application of the system for one type of analysis to another or substantially re-organizing the system and its components. Given the small size of the tubing and fitting assembly or fluidic connection components, such as nuts, ferrules, sleeves, transfer tubing, tips, and so forth, especially together with the complexity of many analytical instrument systems, many operators often spend additional time and effort locating the tubing for a connection or locating an fitting assembly, sometimes in very awkward or difficult to reach locations. By providing a slot 1050 in the nut 1001, an operator can more easily install or disconnect a fluidic connection in an AI system. For example, to make a connection, an operator can first locate or insert the nut 1001 in a port, and then easily insert a portion of the tubing or tube assembly through the slot 1050 of the nut 1001, and then tighten the nut 1001 in the port to form a sealed connection. Similarly, an operator, when disconnecting a fluidic connection, can simply rotate the nut 1001 relative to the port to loosen the fitting assembly and, without removing the nut 1001 from the port, remove the tubing by pulling the tubing through the slot 1050.

Those skilled in the art will appreciate that the current disclosure provides a tubing assembly and a fitting assembly which can be used for making one or more connections in any system that utilizes a face seal (such as a flat-bottomed port), and can withstand the fluid pressures required for ultra-high pressure liquid chromatography (UHPLC) and other analytical instrument applications. While PEEK lined steel (PLS) tubing has been used in other applications, those skilled in the art will appreciate that the tubing and fitting assembly of the present disclosure overcomes issues with the use of PLS, such as, for example, difficulties encountered by users because of the inability of PLS to bend. Those skilled in the art will appreciate that the fitting and tubing assembly configurations described and shown in this disclosure focus on only one end of the tubing and fitting assembly, but the present disclosure may be used in embodiments as a complete fluidic connection between two components, for example, such as a connection including two nuts and tubing with two ends such as described and shown in this disclosure for providing a fluid connection between any two points in an analytical instrument system or other system.

Those skilled in the art will further appreciate that the tubing and fitting assemblies shown and disclosed herein will successfully handle fluid connections in systems in which small volumes of a fluid at high pressures are needed. For example, the tubing in accordance with the present disclosure may have an outside diameter (OD) in the range of from about 1/64 inches to about 1/4 inch, or about 1/64, 1/32, 1/16, 1/8 or 1/4 of an inch in diameter inclusive, and may have an inner diameter (ID) of from about 0.001 to about 0.085 inches, or about 0.001, 0.002, 0.006, 0.010, 0.015, 0.020, 0.025, 0.030, 0.060, or 0.085 inches, inclusive. Moreover, the assembly described and shown in this disclosure is capable of UHPLC pressures (>18,000 psi) at finger-tight torque values of 2-3 in*lbs, for example. The assemblies are also flexible and capable of multiple connection uses prior to failure. It is believed that the fitting assembly of the present disclosure is able to translate rotational torque directly to axial force to generate the seal with a flat-bottom port which will hold at very high pressures like those noted. Those skilled in the art will also appreciate that the fitting assembly of the present disclosure does not require any ferrules or other similar sealing mechanisms, is easy to use by an operator, and can generate a seal at high pressures with torque levels that do not require any tools and are easily obtained by most users. Using such a torque load to make a test connection with a fitting assembly in accordance with the present disclosure, we were able to obtain a sealed fluid connection that maintained a seal at fluid pressures higher than 25,000 psi before a burst or a leak.

Figure 17:
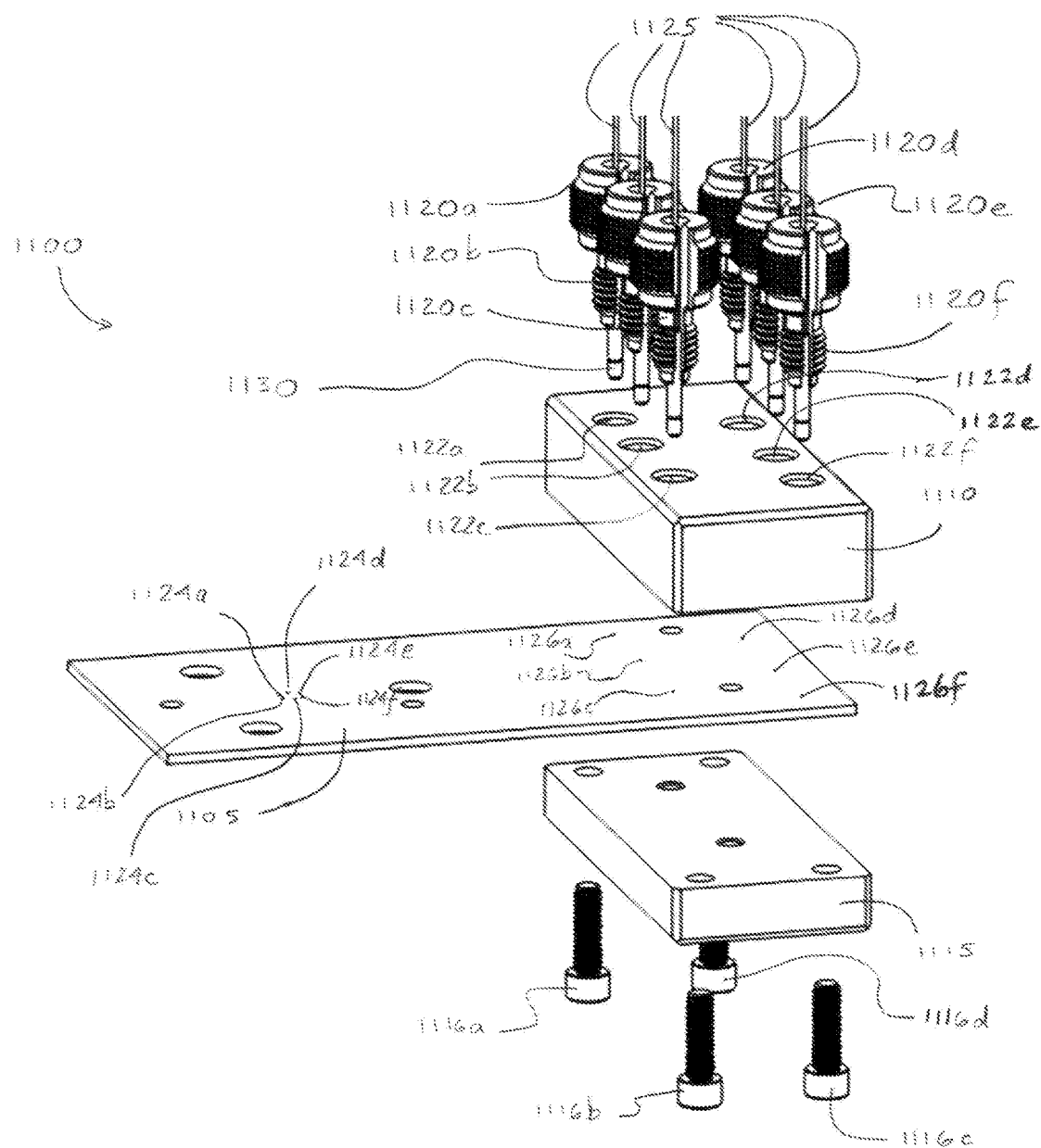
FIG. 17 is an exploded view of a manifold connection assembly in accordance with an embodiment of the present disclosure.
Figure 18:
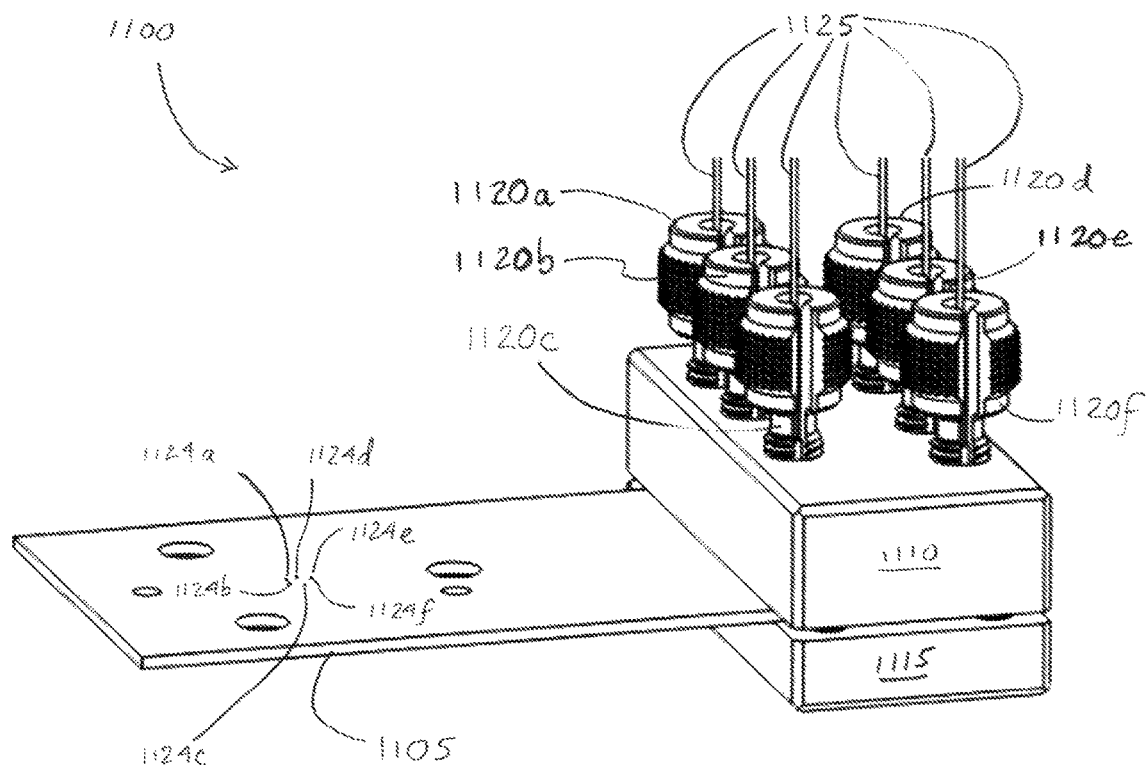
FIG. 18 is a perspective view of the manifold assembly of FIG. 17 shown as assembled.
Figure 19:
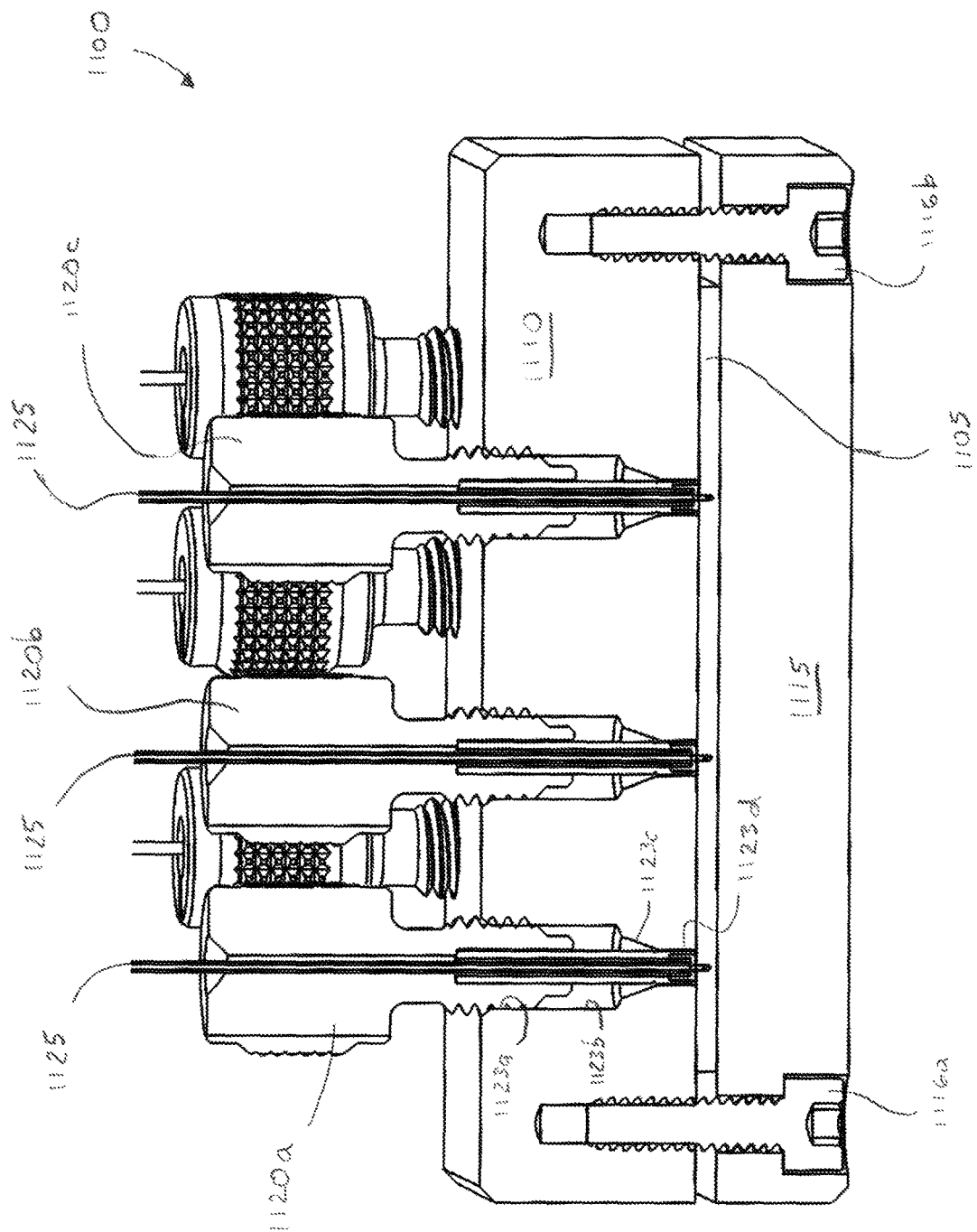
FIG. 19 is a cross-sectional view of the manifold assembly shown in FIG. 18.

Referring now to FIGS. 17-19, an embodiment of a manifold connection assembly is provided. Those skilled in the art will appreciate that in the following embodiments, any one or more of the previous fluidic connection systems and configurations may be used, although only a few are discussed below for purposes of brevity. In FIG. 17, an exploded view of a manifold connection assembly 1100 is shown, which includes a manifold 1105, a backup or backing plate 1115, and a threaded plate or block 1110. Screws 1116a, 1116b, 1116c, and 1116d are provided and, as indicated in FIG. 17, can be aligned with openings in the plate 1115 and are adapted to removably and securely attach the plate 1115 to the manifold 1105. Also shown in FIG. 17 are six tubes 1125. As illustrated in FIG. 17, each of the tubes 1125 extends through a corresponding one of nuts 1120a, 1120b, 1120c, 1120d, 1120e, and 1120f. Each of the nuts 1120a-1120f are adapted to removably and sealingly engage with ports 1122a, 1122b, 1122c, 1122d, 1122e, and 1122f, respectively, which are located in the block 1110. As indicated in FIG. 17, at least one of the tubes 1125 has a tip 1130 such as described in at least one of the embodiments disclosed and described above. It will be appreciated that each of the nuts 1120a-1120f and the tubing 1125 may be any one of a number of different types of nuts and tubing, respectively, with a variety of conventional configurations, but it is preferred that the nuts 1120a-1120f and the tubing 1125 comprise nuts and tubing of one of the embodiments thereof as described above and shown in FIGS. 1-16 of this disclosure.

The manifold 1105 of FIG. 17 further includes openings which serve as fluid outlets or inlets 1126a, 1126b, 1126c, 1126d, 1126e, and 1126f, which are located on the manifold 1105 in locations corresponding to the locations where the ends of the six tubes 1125 will be when the manifold assembly 1100 is assembled and the tubes 1125 are secured to the manifold 1105. Each of the inlets 1126a-1126f correspond to a location where one end of the tubing 1125 can be secured to the manifold 1105. As shown in FIG. 17, the manifold 1105 in this embodiment also has openings, which can serve as fluid inlets or outlets, 1124a, 1124b, 1124c, 1124d, 1124e, and 1124f. In this particular embodiment, the manifold 1105 has fluid pathways or passageways (not shown in FIG. 17) so that each of the openings 1126a-1126f is in fluid communication with one of the corresponding openings 1124a-1124f.

In FIG. 18, the manifold assembly 1100 is shown in a perspective view as assembled. The block 1110 and the plate 1115 are securely attached and, located between the block 1110 and the plate 1115 is the manifold 1105. As shown in FIG. 18, each of the nuts 1120a-1120f are partially secured within the ports 1122a-1122f, respectively, (ports 1122a-1122f are not labeled in FIG. 18), and each of the nuts 1120a-1120f has tubing 1125 extending through a passageway therethrough and extending from one end of the nut.

Referring now to FIG. 19, a cross-sectional view of the manifold assembly 1100 is provided. In FIG. 19, the cross-section is taken through nuts 1120a-1120c, and through the tubing 1125 located within the nuts 1120a-1120c, as well as the block 1110, the plate 1115, and the manifold 1105. Screws 1116a and 1116b are shown are securing the plate 1115 and block 1110 together, with the manifold 1105 located therebetween. As can be seen in FIG. 19, each of the ports 1122a-1122b (not labeled in FIG. 19) has one of the corresponding nuts 1120a-1120c located at least partially therein. Each of the nuts 1120a-1120f are adapted to removably and sealingly engage with a corresponding one of the ports 1122a-1122f of the block 1110. With respect to port 1122a (not labeled in FIG. 19 but in which nut 1120a is partially located), the port 1122a includes a first portion 1123a, a second portion 1123b, a third portion 1123c, and a base portion 1123d. As can be seen in FIG. 19, the port is flat-bottomed, and is adapted to removably receive an end of the tubing 1125 for sealing engagement. The first portion 1123a of the port in this particular embodiment includes internal threads which are adapted to mate and engage with the external threads of the nut 1120a. The second portion 1123b of the port is generally cylindrical and is located between the first threaded portion 1123a of the port and a tapered third portion 1123c of the port, which may be generally conical or frusto-conical in shape. The base portion 1123d of the port in this particular embodiment is cylindrical, with a smaller internal diameter than the internal diameter of the first and second portions 1123a and 1123b of the port, respectively. As shown in FIG. 19, the base portion 1123d may be adapted to snugly receive and hold the end of the tubing 1125.

In the embodiment shown in FIGS. 17-19, the manifold 1105 is adapted to provide a stator for a valve, which may be used in an LC system or other analytical instrument system, for example. The valve (not shown) may be an injection valve, a selection valve, or another valve. Those skilled in the art will also appreciate that the manifold 1105 need not be adapted as a stator for a valve, but may be used independently or may be used in an LC or AI system as a port of another component of such a system.

The manifold 1105 may be made of a relatively hard material, such as a borosilicate or sapphire, stainless steel, titanium, MP35N (a trademark of SPS Technologies, Inc.) and similar alloys, and glass, or other ceramic or metal materials, including alumina, and zirconia. In this particular embodiment, the block 1110 may be made of aluminum, steel, PEEK, or any other material with sufficient strength to support threads and engagement of same, and with sufficient chemical inertness to potential exposure to mobile phases commonly used in HPLC applications. The plate 1115 may be made of any one or more of the same materials as may be used for the block 1110. It will also be appreciated that block 1110 and/or plate 1115 may be incorporated into the frame of an AI instrument of which the manifold is an integral part. Those skilled in the art will appreciate that a variety of other materials may be used for each of block 1110, manifold 1105, and plate 1115, and may be selected depending on the intended uses for which the manifold assembly 1100 may be adapted. It will also be appreciated that, although shown with six tubes 1125, six openings 1122a-1122f, six ports 1126a-1126f, and six ports 1124a-1124f, the manifold assembly 1100 may have fewer or more such fluidic inlets/outlets and/or connections as may be desired. In addition, it will be appreciated that, although the manifold 1105 as shown in FIGS. 17-19 is of a single layer, the manifold 1105 may have multiple layers, which may comprise the same or different materials.

Those skilled in the art will appreciate that the manifold 1105 may comprise multiple layers, each of which may be made of the same or a different material, and may be laminated by diffusion bonding. It will also be appreciated that the inlets/outlets, and fluid pathways or passageways provided in the manifold 1105 typically are of precisely controlled dimensions, and so may be made using chemical etching, photolithography, and similar techniques, although in some instances these features may be made via machining techniques. The pathways in the manifold 1105 may be typically of a hemispherical, circular, half-circle, "D", or rectangular cross-sectional shape, and tend to be about 0.001 inches to about 0.020 inches in diameter, although those skilled in the art will appreciate that for certain applications, larger openings may be desirable. In addition, it will be appreciated that in general the fluid pathways within manifold 1105 and the inlets and/or outlets are desirably of matching diameters. The inlet/outlets openings in the manifold 1105 typically have a matching circular or other cross-sectional shape and are usually about 0.001 inches to about 0.085 inches in diameter, and preferably from about 0.001 to 0.006, 0.001 to 0.010, 0.001 to 0.20, 0.001 to 0.025, 0.001 to 0.030, 0.001 to 0.060, and/or 0.001 to 0.085 inches in diameter. The tubing may be any one of a number of conventional tubing, or may preferably be one of the tubing assemblies described above in this disclosure. Although not shown in FIGS. 17-19, the manifold 1105 may further comprise any one or more of a number of elements useful in LC systems and/or AI systems, such as pressure sensors, temperature sensors, flow rate sensors, heating elements, osmotic pump elements, columns or other separating elements, mixers, splitters, sample loops, and the like. Such elements are typically provided using micro electro-mechanical systems, or MEMs features. Such elements may be provided as elements in one or more of the fluid pathways of the manifold 1105, similar to that shown in U.S. Pat. No. 6,910,503, which was noted above, or as described in U.S. Pat. No. 9,304,115 B2, issues on Apr. 5, 2016 to Bunner et al., and titled "Pressure Sensing and Flow Control in Diffusion-Bonded Planar Devices for Liquid Chromatography," which is hereby incorporated by reference herein as if fully set forth herein.

Figure 20:
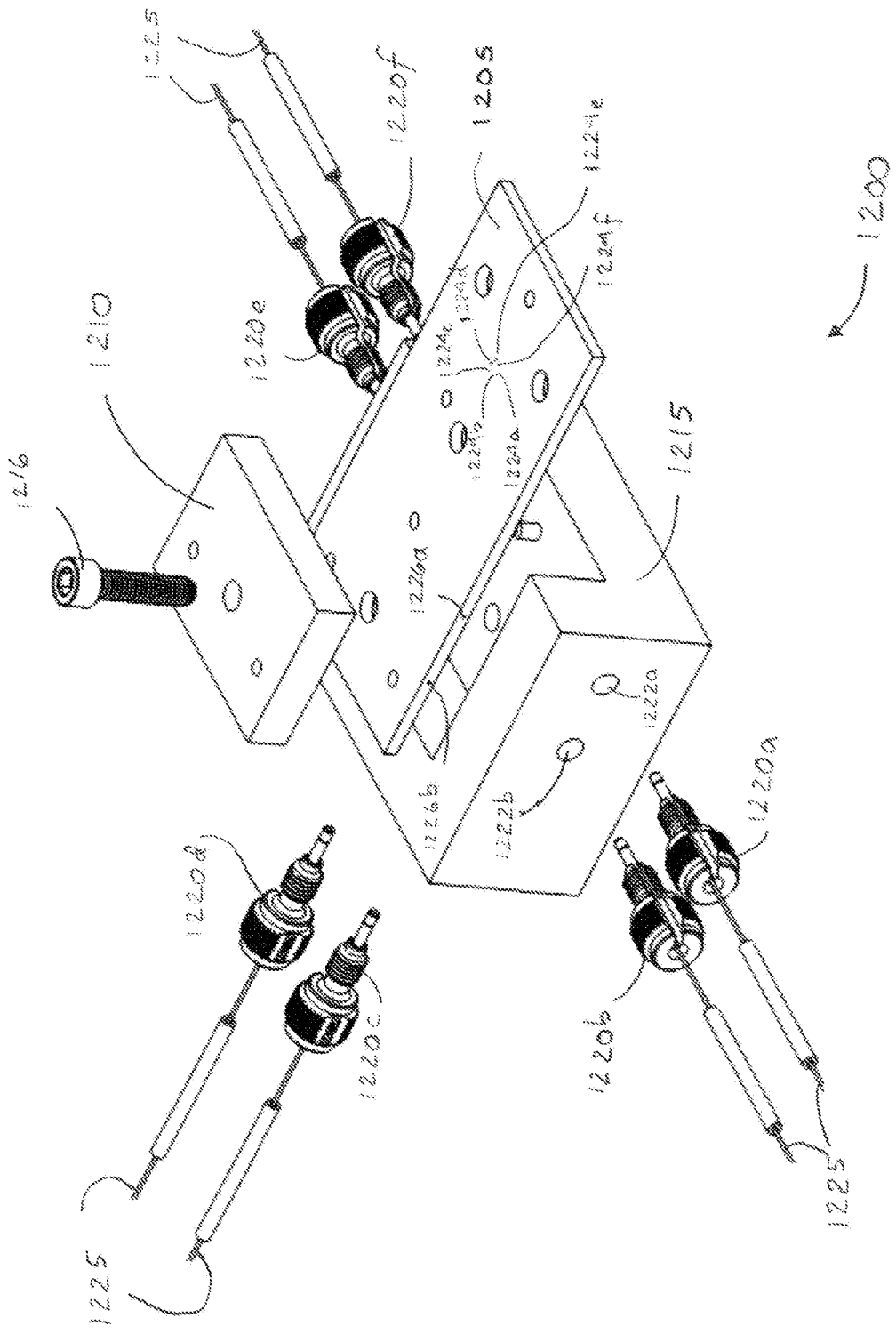
FIG. 20 is an exploded view of another embodiment of a manifold assembly connection in accordance with the present disclosure.
Figure 21:
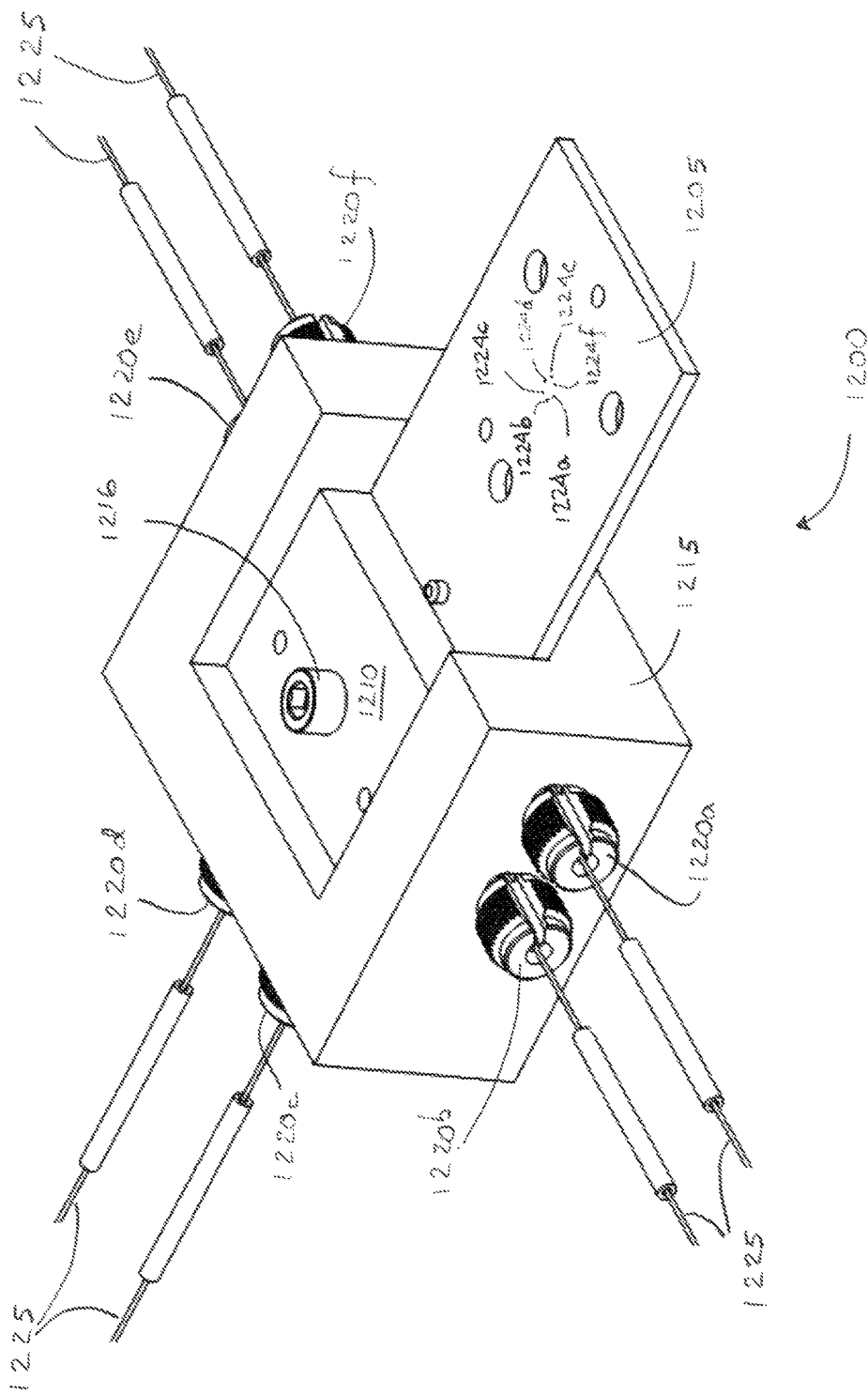
FIG. 21 is a perspective view of the manifold assembly of FIG. 20 shown in an assembled form.

Now referring to FIGS. 20-21, views of an embodiment of a manifold connection assembly 1200 are provided. Those skilled in the art will understand that much of the above discussion regarding manifold assembly 1100 likewise applies to manifold assembly 1200. In FIG. 20, an exploded view of the manifold assembly 1200 is shown. In FIG. 20, a series of tubes 1125 are located in nuts 1220*a*, 1220*b*, 1220*c*, 1220*d*, 1220*e*, and 1220*f*. The manifold assembly 1200 has a manifold 1205, a portion of which is located between a plate 1210 and a block 1215. A screw 1216 is provided for removably securing the plate 1210, the manifold 1205, and the block 1215 together. As also shown in FIG. 20, the block 1215 has openings 1222*a* and 1222*b*, each of which are adapted to receive and removably engage with the tubing 1125 and nuts 1220*a* and 1220*b*, respectively. In addition, the manifold 1205 has openings 1226*a* and 1226*b*, which are located and adapted to provide fluid pathways corresponding to the openings 1222*a* and 1222*b*, respectively. Manifold 1205 also has openings 1224*a*, 1224*b*, 1224*c*, 1224*d*, 1224*d*, 1224*e*, and 1224*f*, each of which is adapted to serve as a fluid inlet or outlet in fluid communication with a fluid pathway provided by corresponding fluid passageways through the manifold 1205 (not shown).

In FIG. 21, the manifold assembly 1200 is shown in an assembled form. Each of the six tubes 1225 are securely connected to the assembly 1200 by one of the corresponding nuts 1220*a*-1220*f*, which are used to secure the tubing to ports in the block 1215. The screw 1216 is used to removably secure the plate 1210 to the block 1215, with a portion of the manifold 1205 located between the plate 1210 and the block 1215.

Figure 22:
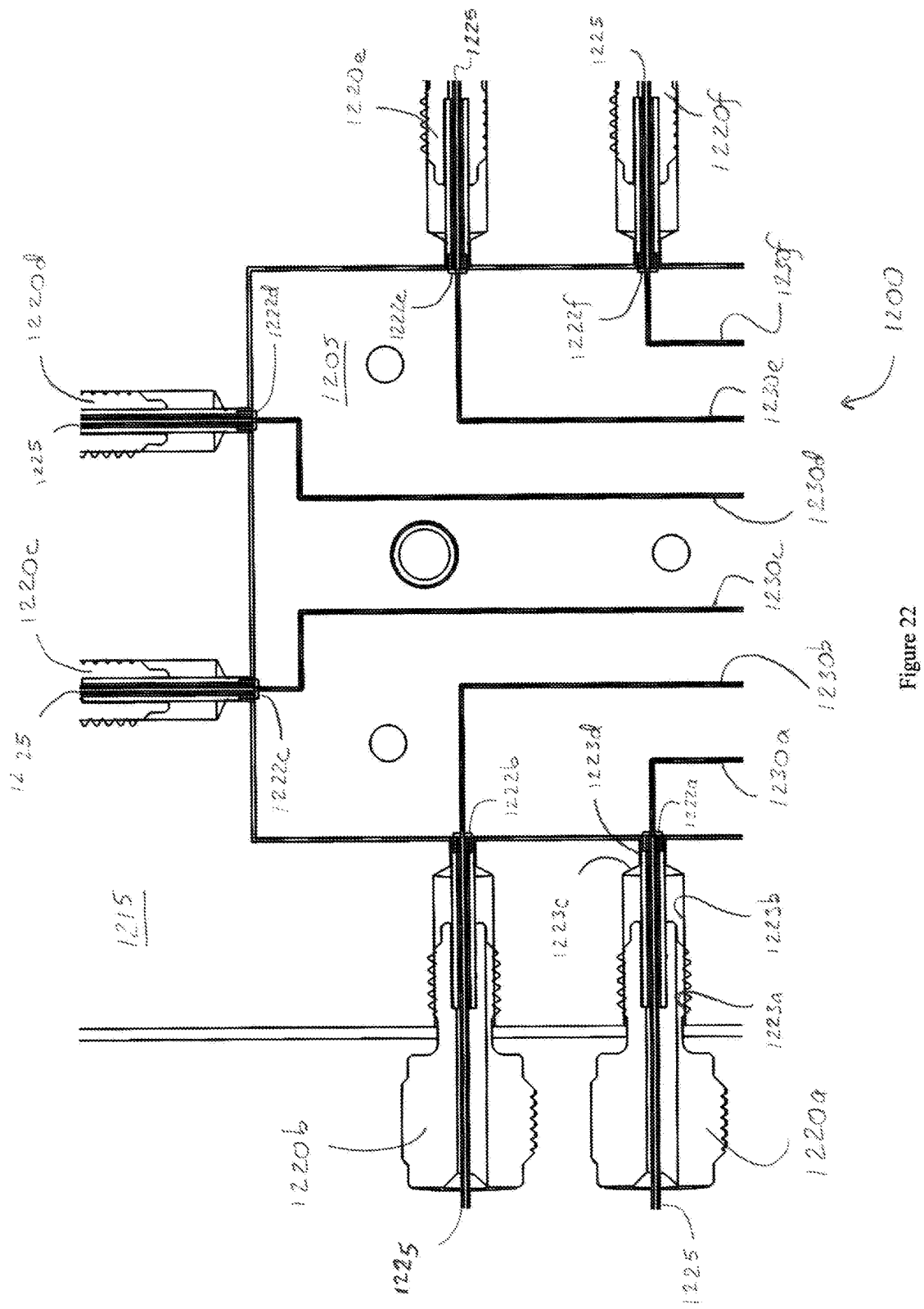
FIG. 22 is a partial cross-sectional view of the manifold assembly of FIG. 21.

Referring now to FIG. 22, a partial cross-sectional view of the manifold assembly 1200 is provided. At least a portion of the manifold 1205 is located within the block 1215. Tubing 1225 is securely and sealingly connected to each of the openings or ports 1222*a*, 1222*b*, 1222*c*, 1222*d*, 1222*e*, and 1222*f* of the manifold 1205 by a corresponding one of the nuts 1220*a*-1220*f*. As shown in FIG. 22, each of fluid pathways 1230*a*, 1230*b*, 1230*c*, 1230*d*, 1230*e*, and 1230*f* extend from a corresponding inlet port or opening 1222*a*-1222*f*. Each of the ports of block 1215 have a first portion 1223*a*, a second portion 1223*b*, a tapered portion 1223*c*, and a bottom portion 1223*d*. As shown in FIG. 22, the first portion 1223*a* has an internal threaded portion which is adapted to engage with the externally threaded portion of the nut 1220*a*. The cooperation of the internal threads of the port 1223*a* and the threads of the nut 1220*a* allow an operator to easily secure the tubing 1225 located within the passageway of the nut 1220*a* by turning the nut 1220*a* and the block 1215 relative to one another so that one end of the tubing is pushed against the manifold 1205 and sealingly held in place against the opening 1222*a*. The port further includes a second portion 1223*b*, which in this particular embodiment is cylindrical. The tapered portion 1223*c* of the port is generally conical or frusto-conical in shape and transitions from the second portion 1223*b* to the bottom portion 1223*d* of the port. The conical or tapered portion 1223*c* helps an operator more easily and quickly align the tubing 1125 and the nut 1220*a* when making a connection. The bottom portion 1223*d* in this particular embodiment has a narrower diameter than that of the second portion 1223*b* and is adapted to snugly receive the tubing 1125. Those skilled in the art will appreciate that, although the details of the port have been provided for the connection of the tubing 1125 by nut 1220*a* to the manifold 1205 opening 1222*a*, the same configuration is shown for each of the connections shown in the embodiment illustrated in FIG. 22. However, the ports of the manifold 1205 need not have the same configuration, but instead the manifold 1205 may provide one or more ports with alternative configurations if desired.

Figure 23:
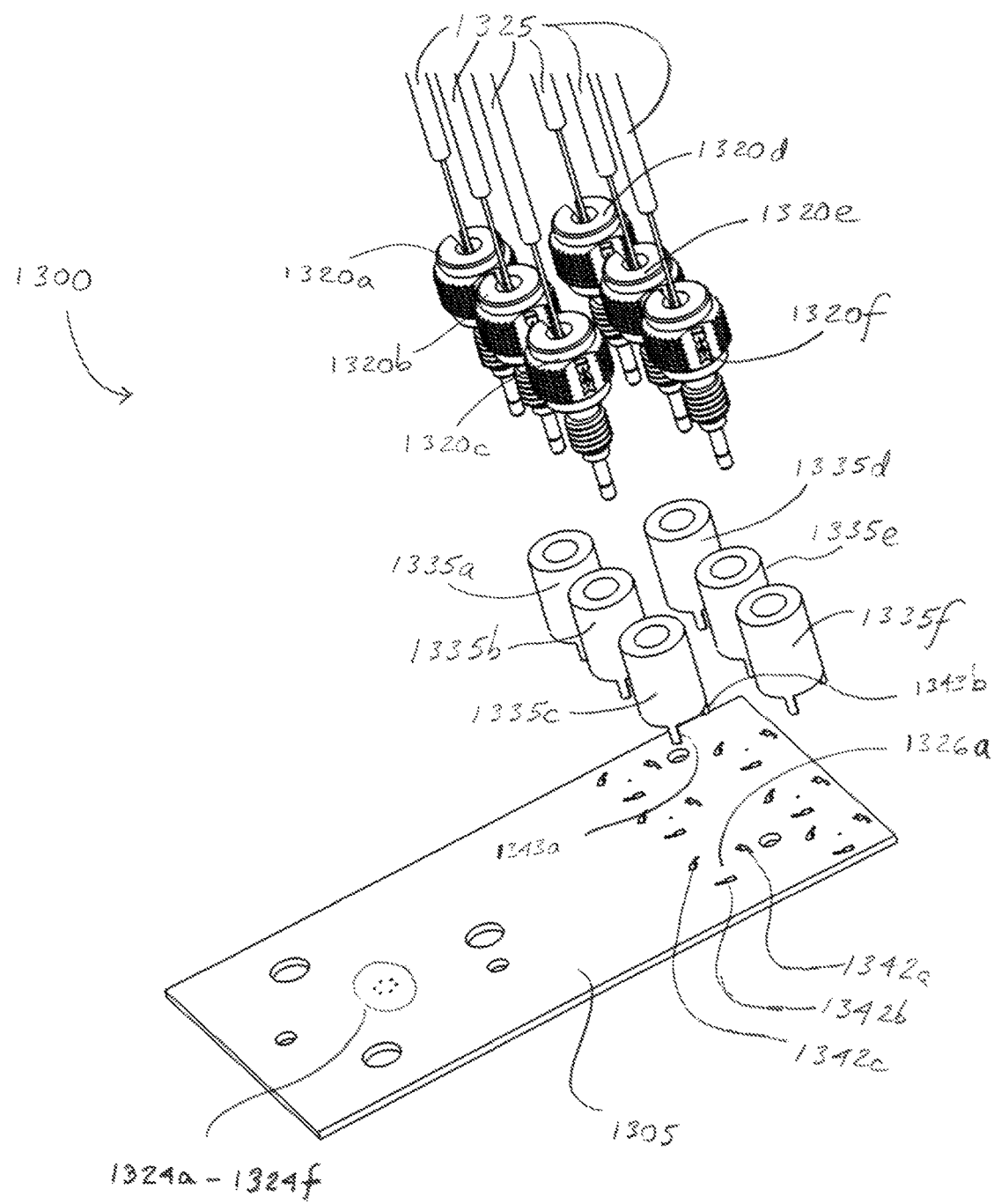
FIG. 23 is an exploded view of another embodiment of a manifold assembly connection in accordance with the present disclosure.
Figure 24:
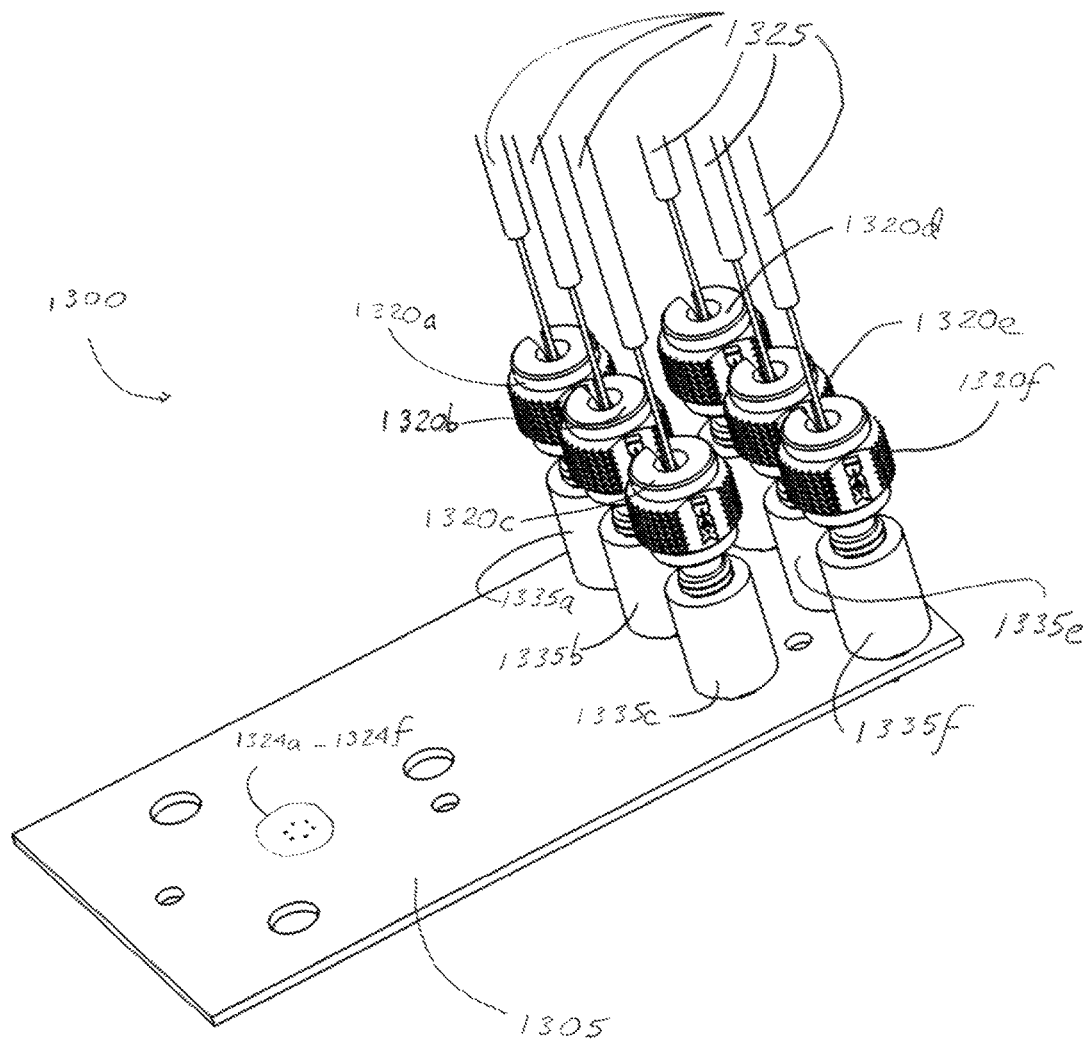
FIG. 24 is a perspective view of the manifold assembly of FIG. 23 shown in an assembled form.
Figure 25:
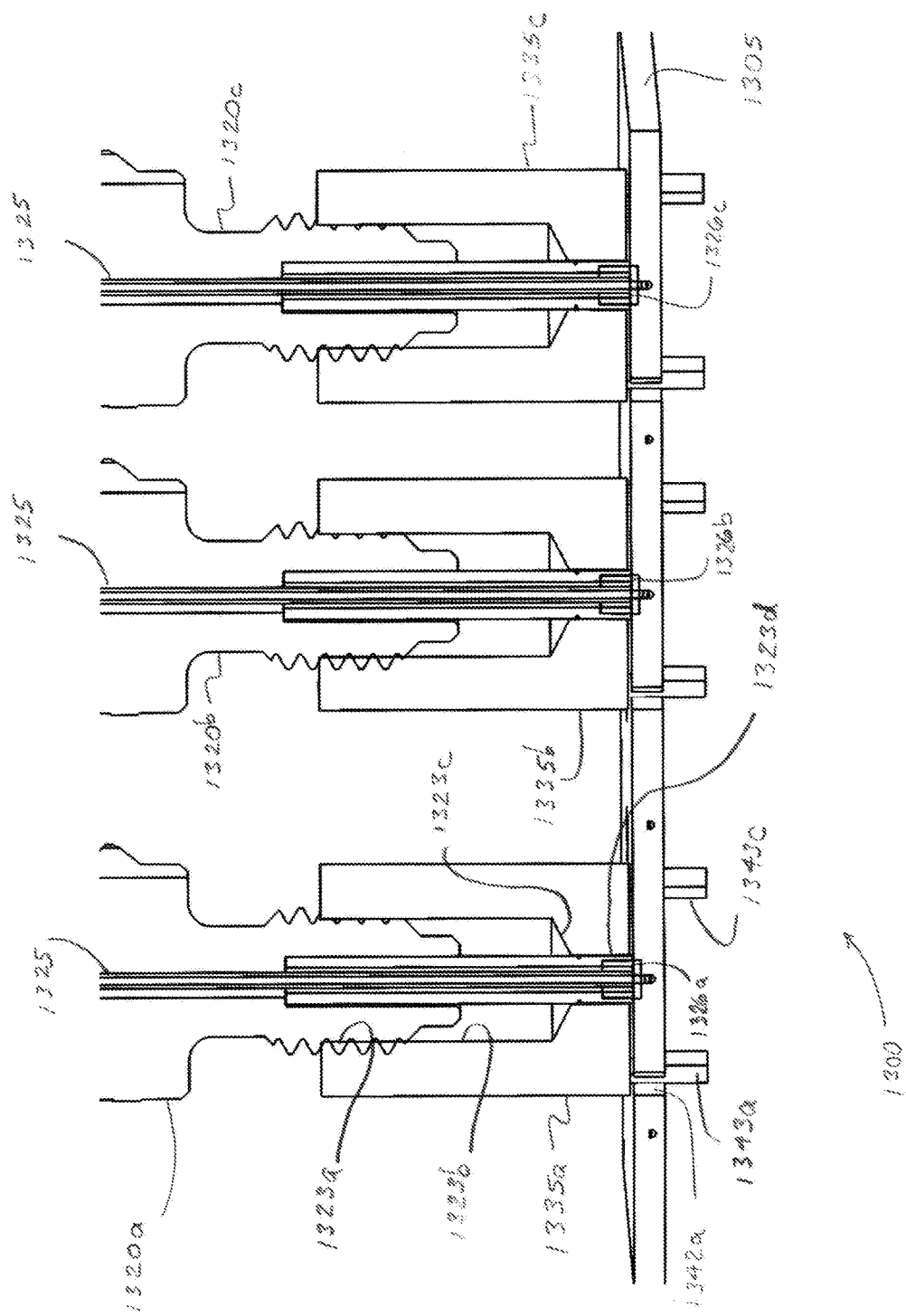
FIG. 25 is a partial cross-sectional view of the manifold assembly of FIG. 24.

Now referring to FIG. 23-25, an embodiment of another manifold assembly 1300 is illustrated. It will be understood and appreciated that much of the above discussion regarding manifold assemblies 1100 and 1200 will also apply to manifold assembly 1300. In FIG. 23, an exploded view of the manifold assembly 1300 is shown. Inf. FIG. 13, the manifold assembly 1300 includes a manifold 1305, snap-in ports 1335*a*, 1335*b*, 1335*c*, 1335*d*, 1335*e*, and 1335*f*, tubing 1325, and nuts 1320*a*, 1320*b*, 1320*c*, 1320*d*, 1320*e*, and 1320*f*. As illustrated in FIG. 23, each of the nuts 1320*a*-1320*f* is adapted to be removably secured in a corresponding one of the ports 1335*a*-1335*f*. Each of the snap-in ports 1335*a*-1335*f* is adapted to be removably attached to the manifold 1305 by a snap-in feature. As shown in FIG. 23, the manifold 1305 includes six openings, each of which has proximal thereto three additional openings. For convenience, only one of the openings in the manifold 1305 and the corresponding three additional openings is labeled in FIG. 23.

As also shown in FIG. 23, the manifold 1305 has an opening 1326 (which is adapted to be in fluid communication with an end of tubing 1325 when the tubing 1325 is securely attached thereto and also in fluid communication with at least one of the openings 1324a-1324f in the manifold through a passageway therethrough). The opening 1326 has three additional openings 1342a, 1342b, and 1342c located proximal thereto and defining a substantially circular path around the opening 1326. It will be appreciated that each of the openings 1342a-1342c is of varying size, and in particular has a first portion which is larger than a second portion. As also shown in FIG. 23, each of the ports 1335a-1335f has three projections 1343a, 1343b, and 1343c (not shown in FIG. 23) which extend from a bottom end. Each of the projections 1343a-1343c generally is in the shape of an arc around the outer diameter of the port 1320a-1320f. Each of the projections 1343a-1343c are adapted to removal by and securely engage with a corresponding one of the additional openings 1342a-1342c to firmly hold the corresponding port 1320a-1320f in place against the manifold 1305. A user can easily and quickly insert the projections 1343a-1343c into the larger portions of the additional openings 1342a-1342c, then turn the port 1320a so that the projections 1343a-1343c are now located in the smaller portions of the openings 1342a-1342c, where the projections are securely (but removably) held and attached.

Referring now to FIGS. 24 and 25, additional views of the manifold assembly 1300 are provided. In FIG. 24, the assembly 1300 is shown as assembled, with each of the nuts 1320a-1320f securely attached to a corresponding one of ports 1335a-1335f and thereby connecting tubing 1325 to the manifold 1305. FIG. 25 provides a partial cross-sectional view of the manifold assembly 1300 in an assembled condition. As shown in FIG. 25, three tubes 1325 are securely and sealingly attached to a first face of the manifold 1305. One end of each of the tubes 1325 is secured to and within a port 1335a-1335c by one of the corresponding nuts 1320a-1320c. As shown in FIG. 25, each of the ports 1335a-1335c has an interior passageway with a first internally threaded portion 1323a, a second, generally cylindrical portion 1323b, a tapered, generally frusto-conically shaped portion 1323c, and a bottom, generally cylindrically shaped portion 1323d. The ends of each of the tubing 1325 abuts one of the openings 1326a-1326c in the face of the manifold 1305. As also shown in FIG. 25, the projections 1343a-1343c (1343b is not shown in FIG. 25) extend through a corresponding one of the openings 1342a-1342c in the manifold 1305. Because the smaller portions of the openings 1342a-1342c are of a size and shape to securely and firmly hold a corresponding projection 1343a-1343c therein, the ports 1335a-1335c are firmly held in place once the manifold assembly 1300 is assembled. However, a user or operator can quickly disconnect one of more of said ports 1335a-1335f from the manifold 1305 by turning the one of the ports 1335a-1335f relative to the manifold 1305 and then pulling the port 1335a-1335f away from the face of the manifold 1305. Alternatively, an operator or user can leave any or all of the ports 1335a-1335f connected to the manifold 1305 once assembled and disconnect, for example, the nut 1320a and tubing 1325 from port 1335a by turning the nut 1320a and/or port 1335a relative to one another and then pulling the nut 1320a away from the port 1335a once the threaded engagement has been disengaged.

Figure 26:
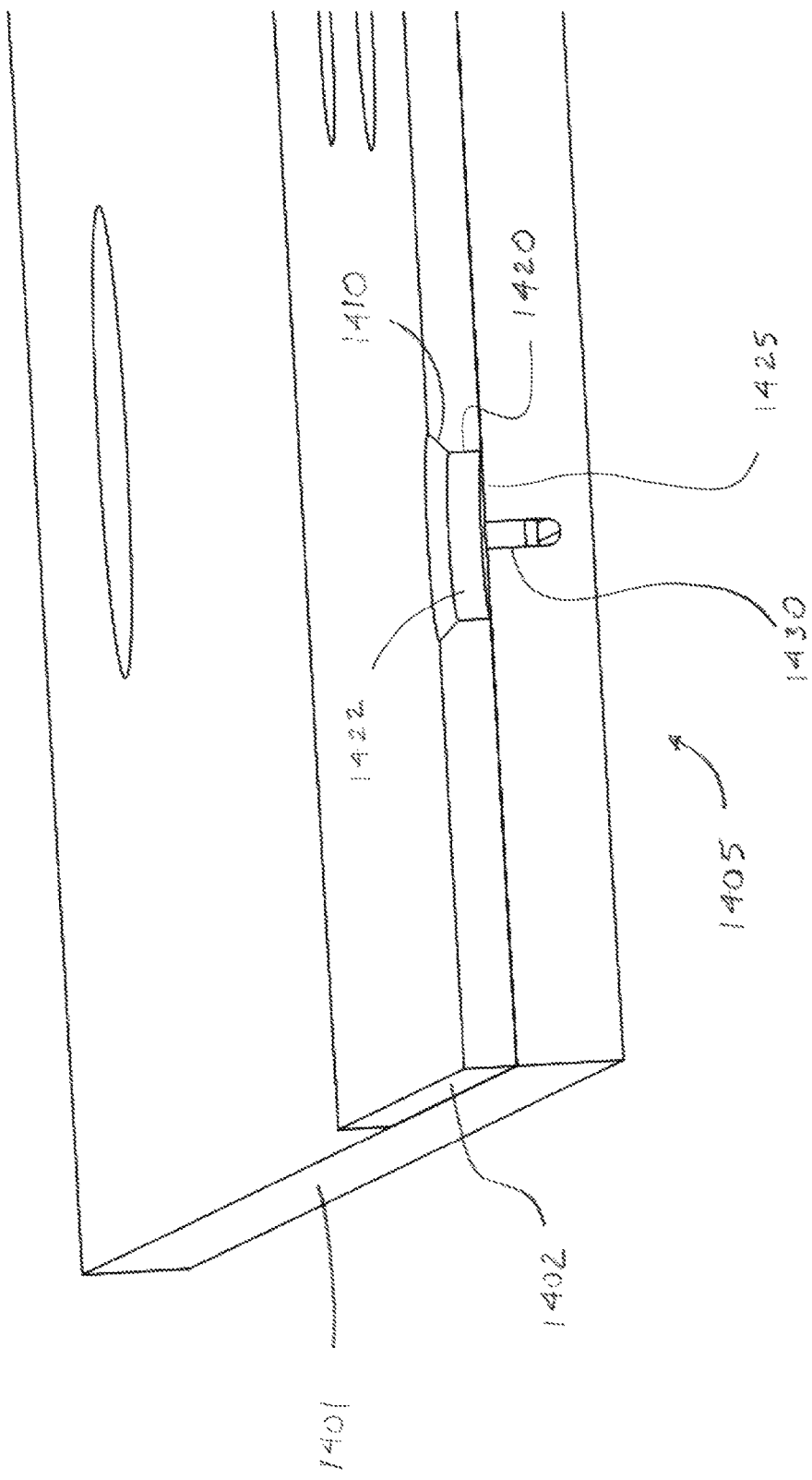
FIG. 26 is an enlarged partial cross-sectional view of a manifold connection assembly in accordance with the present disclosure.

Referring now to FIG. 26, an enlarged partial cross-sectional view of a manifold 1405 is illustrated. As shown in FIG. 26, the manifold 1405 has a first layer 1402 and a second layer 1401. An opening 1422 is shown. The opening 1422 has a first portion 1410, which is tapered or frusto-conical in shape, and has a narrowing diameter from the diameter of the opening 1422 at the face of the layer 1402. The second portion 1420 of the opening 1422 has a narrower diameter, and is generally cylindrically shaped. The tapered portion 1410 provides a guide hole and makes it easier for the operator to position tubing (not shown in FIG. 26) in the opening 1422 to better align the end of the tubing with the opening 1422 and inlet passageway 1430 and helps allow the operator to quickly and easily insert an end of the tubing into the second portion 1420 of the opening 1422. Also shown in FIG. 26 is the fluid pathway 1430 in the manifold 1405 that extends from the opening 1422. Those skilled in the art will appreciate that layer 1402 may be used to provide an optional alignment mask to provide one or more the tapered openings 1422 to help an operator to more quickly and easily align an end of tubing and the fluid passageway through the tubing with an inlet of fluid passageway such as the passageway 1430 as shown in FIG. 26 for example. Although not shown in FIG. 26, such an alignment mask may be very useful in connection with aligning a stator face with a rotor, such as would be the case in connection with the use of the manifold of the present disclosure in a valve, for example, to thereby quickly and easily obtain a precise alignment of the inlet/outlet openings in the stator and rotor in a valve (not shown in FIG. 26).

In FIG. 26, the guide hole 1410 is provided by layer 1402 of the manifold 1405, while the fluid pathway 1430 of the manifold 1405 is in layer 1401. Those skilled in the art will appreciate that the layer 1402 and layer 1401 can be laminated after being separately manufactured, with the opening 1422 made by chemically etching layer 1402, for example. Such a process allows for the precise control of the size, shape and location of the opening 1422 and the portions 1410 and 1420. The layers 1401 and 1402 can be laminated by diffusion bonding or other techniques.

Those skilled in the art will appreciate that the tubing and connections in various LC and AI systems may come in a variety of sizes, and may be as small as 25 microns or so in diameter, or may be 250 microns or more in diameter. In applications in which the tubing inner diameter approaches 25 microns or so, and when the openings in the manifold (such as those shown and described in this disclosure) approach 25 microns or so in diameter, alignment of the fluid pathway in the tubing and the corresponding opening in the manifold becomes critical. The use of a guide hole such as that described above thus provides a particular advantage and benefit in applications which involve smaller tubing diameters and/or manifold opening diameters.

Figure 27:
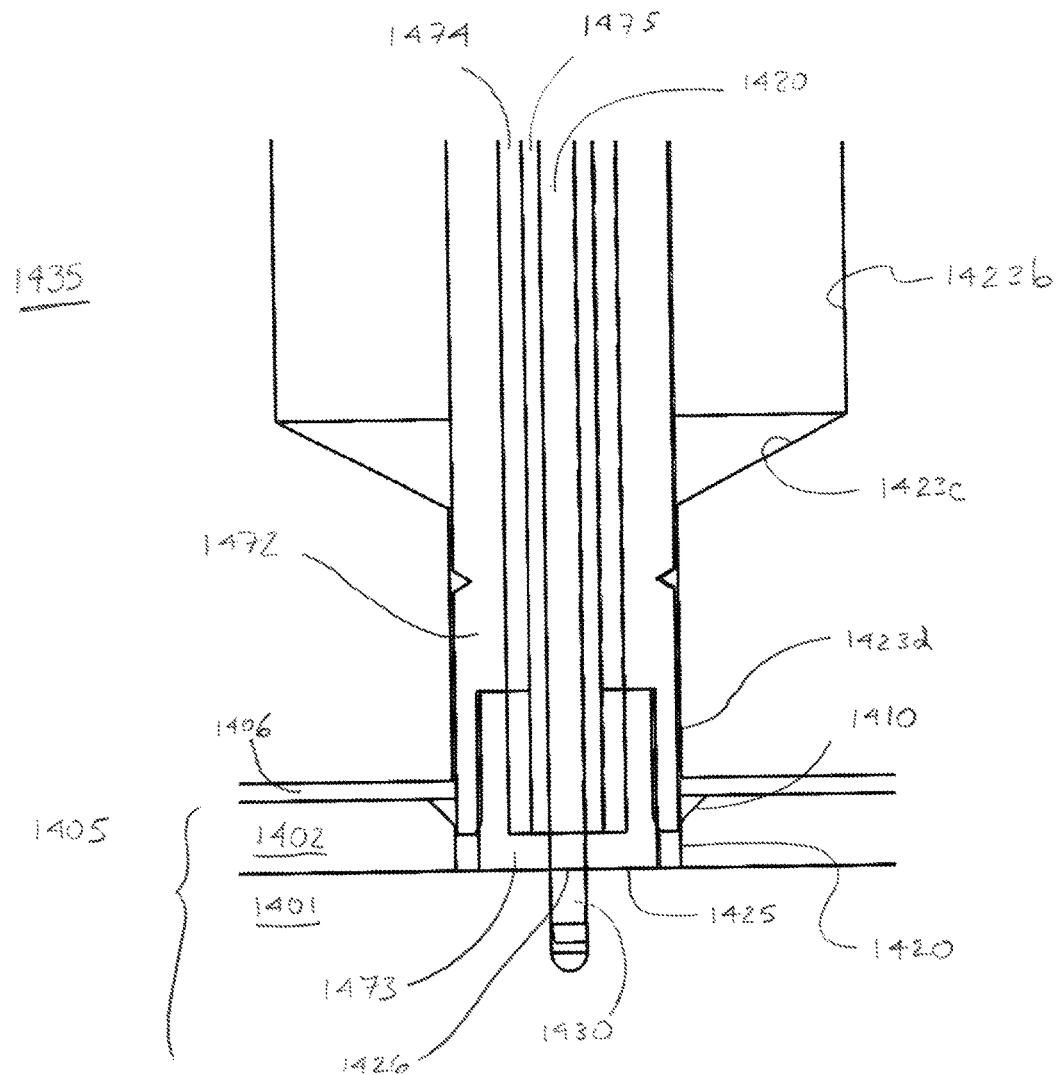
FIG. 27 is an enlarged partial cross-sectional view of a manifold assembly with tubing connected thereto in accordance with the present disclosure.

Now referring to FIG. 27, an enlarged partial cross-sectional view of a manifold 1405 is shown with tubing 1474 and 1475 connected thereto. The tubing has an inner layer 1475 and an outer layer 1474 in this embodiment. In addition, tubing layers 1474 and 1475 are located within a passageway of a sleeve 1472 which in turn is located in a port in a body 1435. The body 1435 may be a block or a snap-in port like those described above, and the block or snap-in port may be permanently or removably attached to the manifold 1405. The manifold 1405 has two layers: 1401 and 1402. It can be seen that a gap 1406 exists between the port body 1435 and the layer 1402. This could be the case, for example, in connection with the use of a snap-in port for port body 1435. Those skilled in the art will appreciate that the gap 1406 does not affect the sealing function of the connection assembly. As also shown in FIG. 27, one end of the tubing abuts a tip 1473, and tip 1473, in turn, has a face that abuts the bottom 1425 of the manifold opening with portions 1410 and 1420. The passageway 1480 within tubing 1474 and 1475 is in fluid communication with the passageway 1430 in the manifold 1405. In this connected condition, the tubing 1474 and 1475 is held securely and sealingly in place for a leak-free and zero dead volume fluid connection to the manifold 1405 via the tubing 1474 and 1475. As can also be seen in FIG. 27, the port includes portions 1423b, 1423c, and 1423d, which can be as described above. Similarly, the opening in the manifold includes tapered portion 1410 and bottom portion 1420, which can be as described above. It will be appreciated that the materials described above for other embodiments of the various portions of the manifold assembly (e.g., tubing, layer, block, port body, tip, etc.) may be the same for the manifold assembly shown in FIG. 27.

Figure 28:
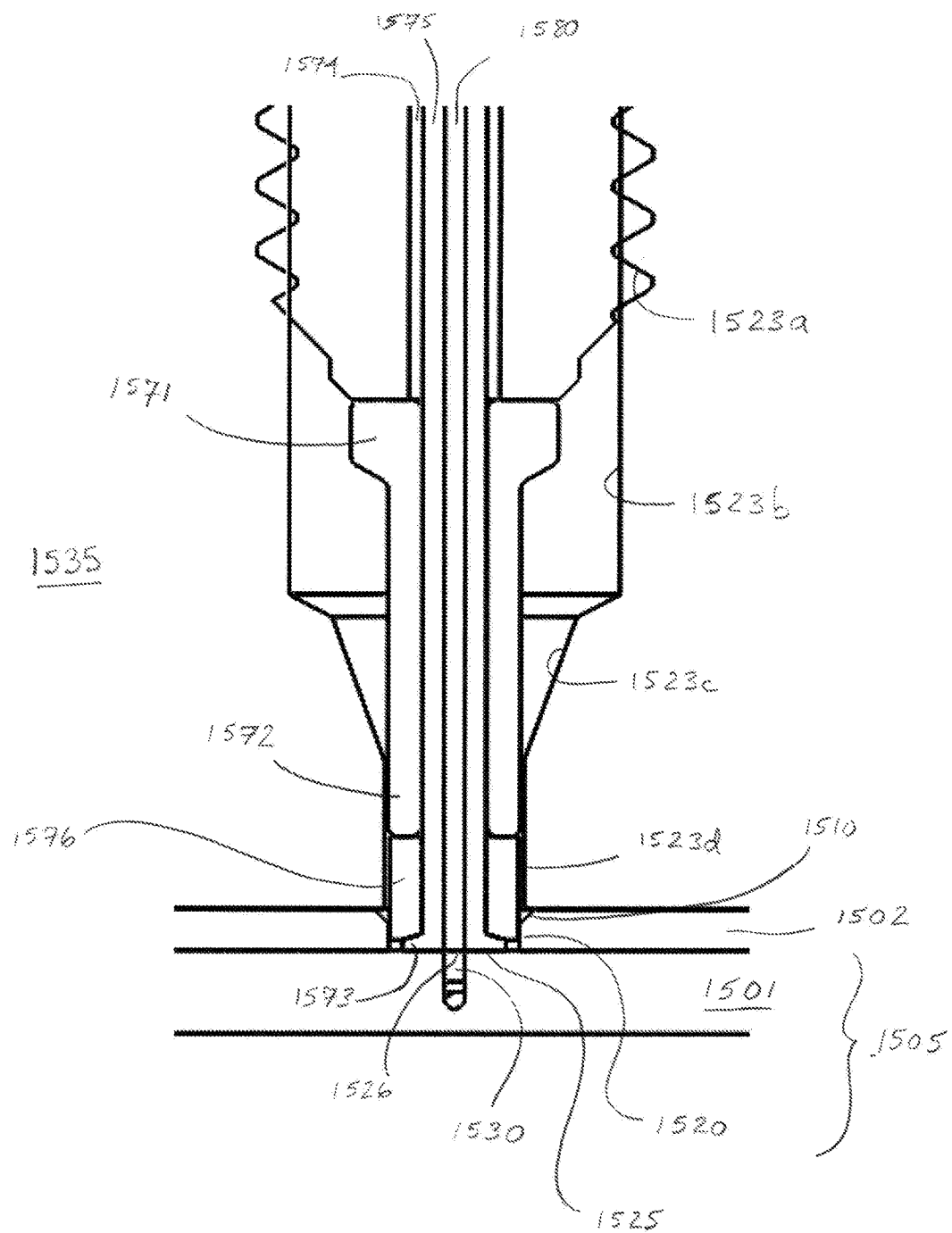
FIG. 28 is an enlarged partial cross-sectional view of another embodiment of a manifold with tubing connected thereto in accordance with the present disclosure.

In FIG. 28, an enlarged partial cross-sectional view of an alternative embodiment of a connection of tubing to a manifold is provided. In FIG. 28, an enlarged partial cross-sectional view of another alternative embodiment of a connection of tubing 1574 and 1575 to a manifold 1505 is provided. As shown in FIG. 28, the tubing has an inner layer 1575 and an outer layer 1574 in this embodiment. In addition, tubing layers 1574 and 1575 are located within a passageway of a sleeve 1572 which in turn is located in a port in a body 1535. The body 1535 may be a block or a snap-in port like those described above, and the block or snap-in port may be permanently or removably attached to the manifold 1505. The sleeve 1572 has a first end and a second end, with the first end 1571 having a portion with a larger outer diameter than the outer diameter of the second end. The first end of the sleeve 1572 abuts an end of the nut, while the second end of the sleeve 1572 abuts a first end of a ring 1576. The second end of the ring 1576 abuts and presses against the flared tip 1573 of the tube 1575. The manifold 1505 has two layers: 1501 and 1502. As also shown in FIG. 28, one end of the tubing 1575 has integrally formed therein a tip 1573, and tip 1573, in turn, has a face that abuts the bottom 1525 of the manifold opening with portions 1510 and 1520. The passageway 1580 within tubing 1574 and 1575 is in fluid communication with the passageway 1530 in the manifold 1505. In this connected condition, the tubing 1574 and 1575 is held securely and sealingly in place for a leak-free and zero dead volume fluid connection to the manifold 1505 via the tubing 1574 and 1575. As can also be seen in FIG. 28, the port includes portions 1523a, 1523b, 1523c, and 1523d, which can be as described above. Similarly, the opening in the manifold includes tapered portion 1510 and bottom portion 1520, which can be as described above. It will be appreciated that the materials described above for other embodiments of the various portions of the manifold assembly (e.g., tubing, layer, block, port body, tip, etc.) may be the same for the manifold assembly shown in FIG. 28.

Those skilled in the art will appreciate that a manifold assembly in accordance with the present disclosure may be adapted to cooperate with various types of tubing and fitting assemblies. In particular, the configuration of the manifold port connection may be adapted so that it provides in one embodiment a first portion with a first diameter and a second portion at the bottom of the port with a smaller diameter, and provides a bore end surface at the bottom of the first portion. For example, certain capillary tubing and assemblies like those shown and described in U.S. Pat. No. 9,334,989 B2, issued to Jencks et al. on May 10, 2016 and titled "Low Carryover High Pressure Fluidic Fitting" ("Jencks et al."), which is hereby incorporated by reference herein as if fully set forth herein, can be used with a manifold assembly in accordance with the present disclosure.

Figure 29:
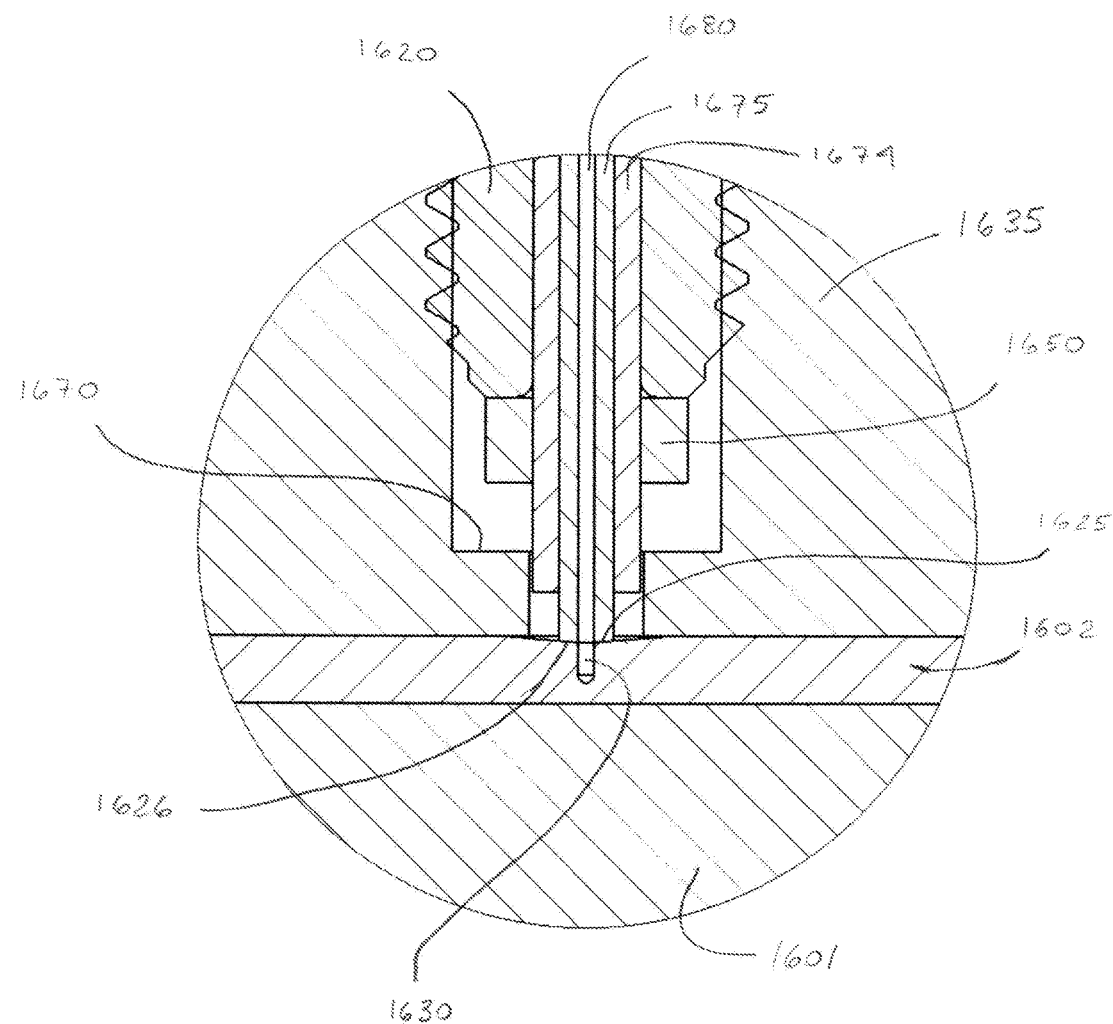
FIG. 29 is an enlarged partial cross-sectional view of another embodiment of a manifold connection with tubing connected thereto in accordance with the present disclosure.

Referring to FIG. 29, an enlarged cross-sectional diagram of a connection assembly is shown. Those skilled in the art will appreciate that a manifold in accordance with the present disclosure may include one or more of such connection assemblies, although just one is shown in FIG. 29. As shown in FIG. 29, a tube has an inner capillary tubing layer 1675, as well as an outer layer 1674, and a fluid passageway therethrough. The tube is located within a port of a body 1635 in accordance with the present disclosure, and is secured therein by a threaded nut 1620. The body 1635 may be a block or a snap-in port like those described above, either or both of which may be permanently or removably attached to the manifold layer 1602. The tip of one end of the inner capillary tube 1675 is abutting the bottom face 1625 of the port. Layer 1602 has a curved or arcuate face 1626 adapted to sealingly engage with the end of the capillary tube 1675 with the end of the tube 1675 abuts the face 1626. As can also be seen in FIG. 29, the fluid passageway 1680 of the capillary tube 1675 is aligned with the fluid passageway 1630 in layer 1602. Generally, we prefer that the size and cross sections of the passageways 1680 and 1630 match; i.e., the passageways 1680 and 1630 are preferably of the same size and shape.

Still referring to FIG. 29, a collet 1650 can be provided. The collet 1650 can be permanently or removably attached to a portion of the outer layer 1674 of the tubing. Those skilled in the art will appreciate that the collet 1650 in this particular embodiment may be like that shown in the Jencks et al. patent noted above. It will be appreciated that the materials described above for other embodiments of the various portions of the manifold assembly (e.g., tubing, layer, block, port body, tip, etc.) may be the same for the manifold assembly shown in FIG. 29.

Figure 30:
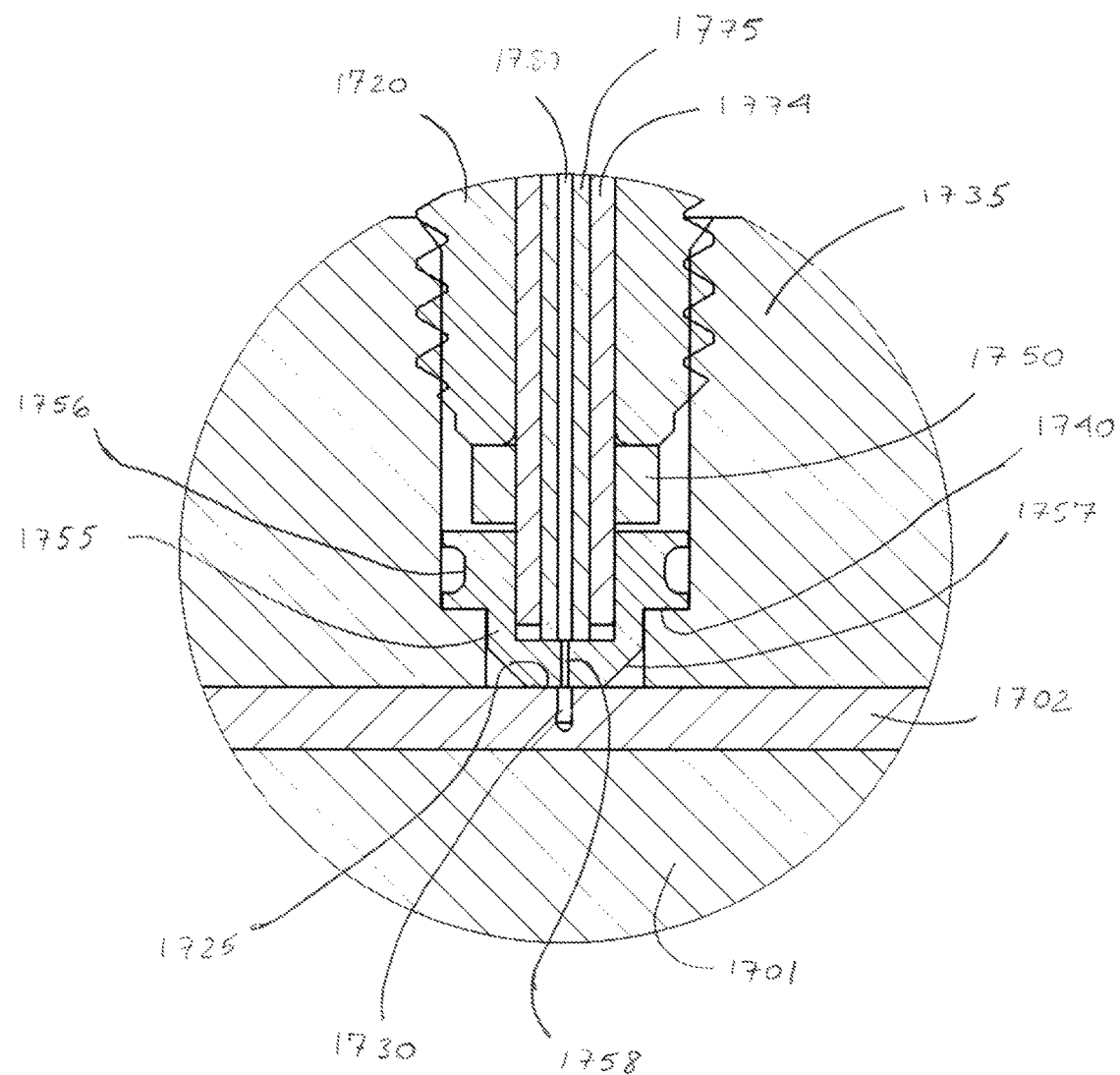
FIG. 30 is an enlarged partial cross-sectional view of another embodiment of a manifold connection with tubing connected thereto in accordance with the present disclosure.

Referring now to FIG. 30, an enlarged cross-sectional diagram of a connection assembly is shown. Those skilled in the art will appreciate that a manifold in accordance with the present disclosure may include one or more of such connection assemblies, although just one is shown in FIG. 30. As shown in FIG. 30, a tube has an inner capillary tubing layer 1775, as well as an outer layer 1774, and a fluid passageway 1780 therethrough. The tube is located within a port of a body 1735 in accordance with the present disclosure, and is secured therein by a threaded nut 1720. The body 1735 may be a block or a snap-in port like those described above, either or both of which may be permanently or removably attached to the manifold layer 1702. The body 1735 may be a block or a snap-in port like those described above, either or both of which may be permanently or removably attached to the manifold layer 1702. The tip of one end of the inner capillary tube 1775 is abutting the bottom bore surface of the seal 1755. Layer 1702 has a flat face 1725 adapted to sealingly engage with one end of the seal 1755 when the end of the seal 1755 abuts the face 1725. As can also be seen in FIG. 30, the fluid passageway 1780 of the capillary tube 1775 is aligned with both a fluid passageway 1758 in the seal 1755 and with the fluid passageway 1730 in layer 1702. In this particular embodiment, it can be seen that the passageway 1758 has a slightly smaller diameter than that of passageways 1780 and 1730. Although not shown in FIG. 30, it will be understood that the size and cross sections of the passageways 1780, 1758, and 1730 may all be of the same size and shape, or may be of differing sizes or shapes.

Still referring to FIG. 30, a collet 1750 can be provided. The collet 1750 can be permanently or removably attached to a portion of the outer layer 1774 of the tubing. The collet 1750 is adapted to be moved towards the layer 1702 when the threaded nut 1720 is screwed into the port. The threads of the nut 1720 and cooperating threads of the port, as well as the shape and size of the collet 1750, are selected so that the collet 1750 is adapted to have a first side abut the end of the nut 1720. The seal 1755 is adapted to sealingly engage with the surface 1725 of the layer 1702 when they are abutting. As shown in FIG. 30, the seal 1755 has one end adapted to engage with the face 1725 of the layer 1702, and this end includes tapered portions 1757, which may be frusto-conical in shape or may have another shape. The tapered portion 1757 of the seal 1755 provides an end of the seal 1755 which has a smaller outer diameter. It can be seen from FIG. 30 that the seal 1755 has a first portion, proximal the collet 1750, which has a first outer diameter, a reduced diameter portion 1756, and then a portion with the first outer diameter, with the first portion of the seal 1755 adapted to abut a bore end surface 1740 when the assembly is connected and sealingly engaged with the manifold. In addition, the seal 1755 has a second portion which includes the previously mentioned tapered portion 1757, with the second portion proximal the layer 1702 when the assembly is in a connected configuration. Those skilled in the art will appreciate that the collet 1750 and the seal 1755 in this particular embodiment may be like those shown in the Jencks et al. patent noted above. It will be appreciated that the materials described above for other embodiments of the various portions of the manifold assembly (e.g., tubing, layer, block, port body, tip, etc.) may be the same for the manifold assembly shown in FIG. 30.

Figure 31:
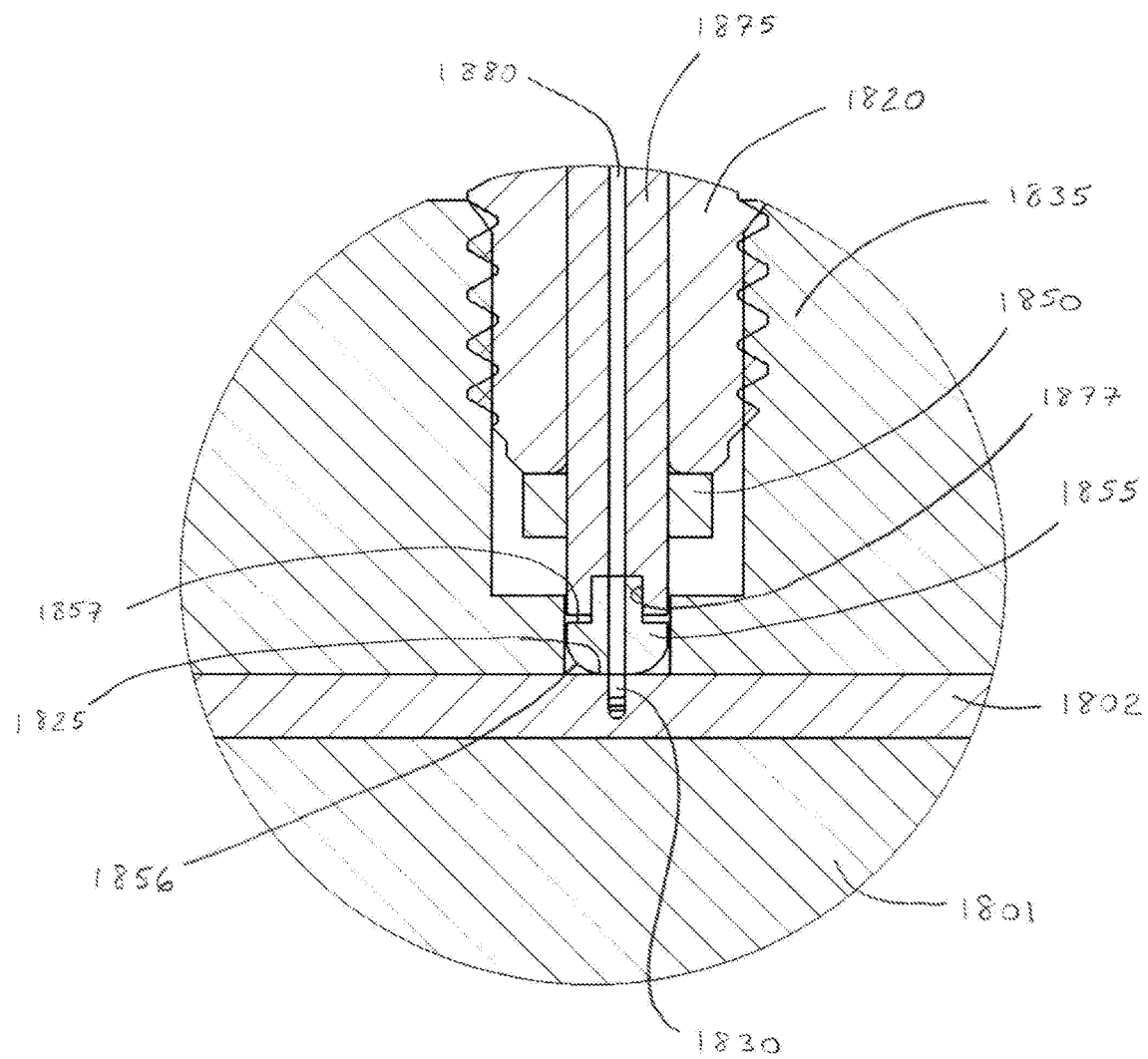
FIG. 31 is an enlarged partial cross-sectional view of another embodiment of a manifold connection with tubing connected thereto in accordance with the present disclosure.

Referring now to FIG. 31, an enlarged cross-sectional view of an alternative embodiment of a connection assembly for a manifold in accordance with the present disclosure is provided. As with other illustrations provided herein, it will be appreciated that, although only a single connection is illustrated in FIG. 31, a manifold of the present disclosure may have any one or more of such fittings connected thereto as may be desired. In FIG. 31, an end of a tube 1875 is shown connected in a port in a body 1835, which may be a block or a snap-in port like those described above. The tube 1875 has a fluid passageway 1880 therethrough, and a portion of the tube 1875 is located within a passageway through a threaded nut 1820. The nut 1820 has a first end abutting a first side of a collet 1850. In addition, one end of the tube 1875 has a recess or seat portion 1877, which is adapted to receive therein a first side of a tip 1855. The second side of the tip 1855 has a curved or arcuate surface portion 1856. As illustrated in FIG. 31, the surface portion 1856 can described a hemispherical shape, although it will be appreciated that the surface portion 1856 can describe or define other curved or arcuate shapes. The end of the surface portion 1856 is adapted to abut and form a seal when abutting against the surface 1825 of the layer 1802. As also shown in FIG. 31, the tip 1855 has shoulder portions 1857 adapted to abut against the outer portions of the end of the tube 1875, so that when the tube 1875 is urged towards the layer 1802, the outer ends of the tube 1875 urge the shoulders 1857 of the tip 1855 and thus tip 1855 towards the layer 1802 to obtain a sealing engagement of the tip 1855 against the layer 1802. It will be appreciated that in the connected configuration shown in FIG. 31, the fluid passageway 1880 of the tube 1875 is of the same size and is aligned with the fluid passageway 1830 in the layer 1802, although it will be further appreciated that the fluid passageways 1880 and 1830 may be of differing sizes and shapes and may not be aligned. Those skilled in the art will appreciate that the collet 1750 and the seal 1755 in this particular embodiment may be like those shown in the Jencks et al. patent noted above. It will be appreciated that the materials described above for other embodiments of the various portions of the manifold assembly (e.g., tubing, layer, block, port body, tip, etc.) may be the same for the manifold assembly shown in FIG. 31.

Figure 32:
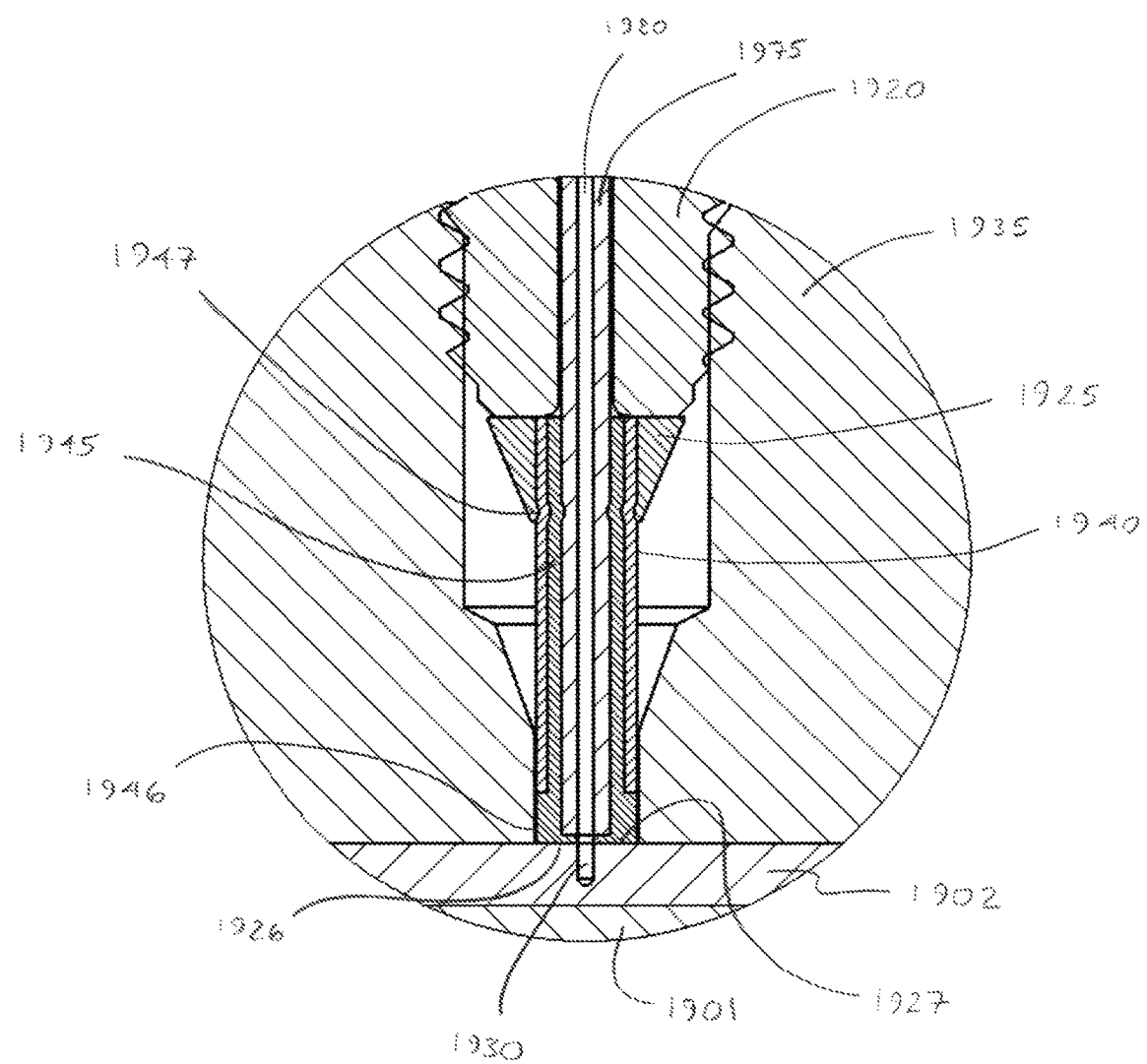
FIG. 32 is an enlarged partial cross-sectional view of another embodiment of a manifold connection with tubing connected thereto in accordance with the present disclosure.

Referring now to FIG. 32, an enlarged cross-sectional view of an alternative embodiment of a connection assembly for a manifold assembly in accordance with the present disclosure is provided. As with the other illustrations provided herein, it will be appreciated that, although only a single connection is illustrated in FIG. 32, a manifold of the present disclosure may have any one or more of such fittings connected thereto as may be desired. In FIG. 32, an end of a tube 1975 is shown connected in a port in a body 1935, which may be a block or a snap-in port for a manifold like those described above. The tube 1975 has a fluid passageway 1980 therethrough, and a portion of the tube 1975 is located within a passageway through a threaded nut 1920. The nut 1920 has a first end abutting a first side of an attachment piece 1925, with the second side of the attachment piece 1925 having a radially inward located end portion 1947, which pushes against portions of a sleeve 1940 and, in turn, pushes against a portion of a sealing piece 1945, which in turn pushes against a portion of the capillary tube 1975. In addition, one end of the tube 1975 is located within a seat portion at the bottom end of the sealing piece 1945. The seat or recess at the bottom end of the sealing piece 1945 is adapted to receive therein a first end of the tube 1975. The end face 1926 of the sealing piece 1945 is adapted to abut a portion 1927 of a surface of the manifold layer 1902 and form a seal between the end face 1926 and the manifold surface portion 1927 when the assembly is connected.

As also shown in FIG. 32, the lower end of the sealing piece 1945 has an end portion 1946 adapted to abut against the surface of the lower walls of the port and form a radial seal in a connected configuration. The end portion 1946 has an outer diameter that is close to or the same as the inner diameter of the lower end of the port. Above the end portion 1946, the sealing piece has a smaller outside diameter and a sleeve 1940 surrounds the sealing piece 1945. The sleeve 1940 in this particular embodiment has an attachment 1925 attached thereto at a top end of the sleeve 1940. As shown in FIG. 32, one end of each of the attachment 1925, the sleeve 1940, and the sealing piece 1945 abuts the lower end of the nut 1920. When the nut 1920 is rotated to make a threaded connection with the port, the nut 1920 moves downwardly into the port and thus pushes the attachment 1925, the sleeve 1940, and the sealing piece 1945 downward to urge the lower end face 1926 of the sealing piece against the bottom face 1927 and form a seal. The attachment 1925 includes a lower end portion 1947 which is tapered and pushes against and crimps the sleeve 1940 where the end portion 1947 contacts the outside of the sleeve 1940. The sleeve 1940, as shown in FIG. 32, may be deformed by such crimping contact and therefore pushes against the outside of an adjacent portion of the sealing piece 1945, thereby deforming the sealing piece 1945 and urging it to push against and crimp a portion of the tube 1975. The end portion 1947 thus keeps the combination of the sleeve 1940, the sealing piece 1945, and the tube 1975 attached as an assembly so that none rotates independently of the others, but instead they rotate and move axially together as if a single piece. It will be appreciated that in the connected configuration shown in FIG. 32, the fluid passageway 1980 of the tube 1975 is of the same size and is aligned with the fluid passageway 1930 in the layer 1902, although it will be further appreciated that the fluid passageways 1980 and 1930 may be of differing sizes and shapes and may not be aligned. Those skilled in the art will appreciate that the connection assembly described and shown in this particular embodiment in FIG. 32 may be like one or more of those shown in U.S. Pat. No. 9,091,693, issued on Jul. 28, 2015 to Hochgraeber et al., and titled "Plug Unit and Connection System for Connecting Capillary Tubes, Especially for High-Performance Liquid Chromatography" ("Hochgraeber"), which is hereby fully incorporated by reference as if fully set forth herein. It will be appreciated that the materials described above for other embodiments of the various portions and features of the manifold connection assemblies disclosed above (e.g., tubing, layer, block, port body, tip, etc.) may be the same for the manifold connection assembly shown in FIG. 32 and its corresponding components and features. For example, for use of the assembly in biocompatible environments and applications, the tube 1975, the sealing piece 1945, and the layer 1902 would comprise biocompatible materials. The sealing piece 1945 could comprise PEEK or other elastomeric or polymer materials, the tube 1975 could comprise a glass or silicate material, and the sleeve 1940 and/or the nut 1920 could comprise PEEK or other polymer materials, or could comprise steel or other materials if desired.

Figure 33:
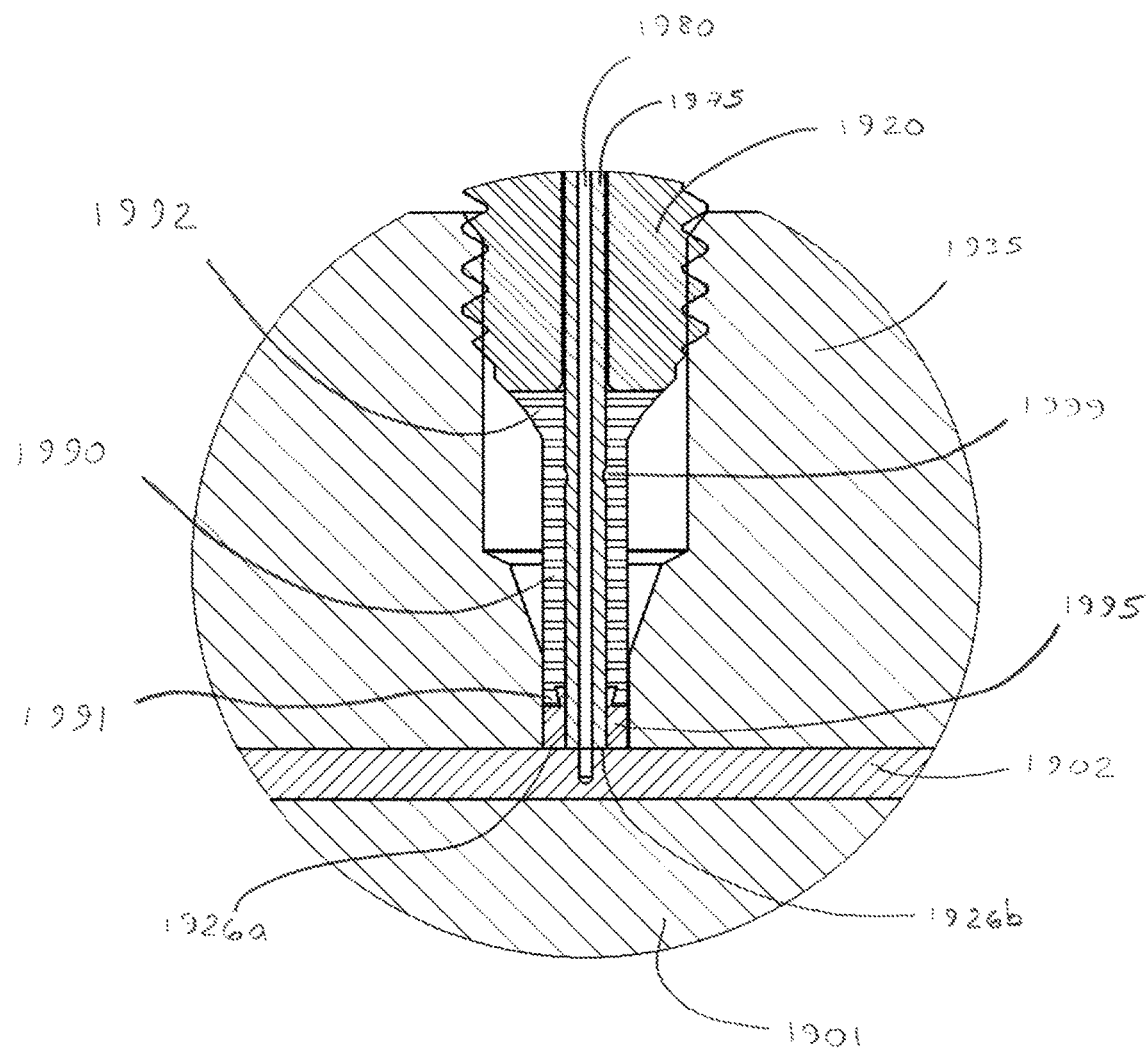
FIG. 33 is an enlarged partial cross-sectional view of another embodiment of a manifold connection with tubing connected thereto in accordance with the present disclosure.

Referring now to FIG. 33, an enlarged cross-sectional view of an alternative embodiment of a connection assembly for a manifold assembly in accordance with the present disclosure is provided. As with other illustrations provided herein, it will be appreciated that, although only a single connection is illustrated in FIG. 33, a manifold assembly of the present disclosure may have any one or more of such fitting assemblies connected thereto as may be desired. The embodiment shown in FIG. 33 is similar to that shown in FIG. 32, with like features and items having like numbers for convenience. In FIG. 33, an end portion of a tube 1975 is shown connected in a port in a body 1935, which may be a block or a snap-in port for a manifold like those described above. The tube 1975 has a fluid passageway 1980 therethrough, and a portion of the tube 1975 is located within a passageway through a threaded nut 1920. The nut 1920 has a first end abutting a first end 1992 of a sleeve piece 1990, with the second side of the sleeve piece 1990 having a radially inward located portion 1999, which pushes against and may crimp an adjacent portion of the capillary tube 1975. In addition, the lower end of the tube 1975 has an end face 1926b abutting the bottom face of the port. The lower end of the tube 1975 is surrounded by a sealing element 1995, which has a bottom face 1926a abutting the bottom surface of the port. As shown in FIG. 33, the bottom end of tube 1975 and the bottom end of the sealing element 1995 provide a seal at the bottom of the port. It can be seen that the sealing element 1995 has a top end with projecting portions which are angled radially outwardly from the longitudinal axis of the assembly, while the sleeve piece 1990 has a lower end with notched portions 1991 adapted to receive and hold the projecting portions of the sealing element 1990.

As also shown in FIG. 33, the sealing piece 1995 is adapted to abut against the surface of the lower walls of the port and form a radial seal in a connected configuration. The end portion of the sealing piece 1995 may have an outer diameter that is the same as or close to, (and may exceed or be slightly less than) the inner diameter of the lower end of the port. The sleeve 1990 in this particular embodiment has a flared portion 1992 at its top end. As shown in FIG. 33, the top end of the sleeve 1990 abuts the lower end of the nut 1920. When the nut 1920 is rotated to make a threaded connection with the port, the nut 1920 moves downwardly into the port and thus pushes the sleeve 1990, and in turn the sealing piece 1995, downward to urge the lower end face 1926a of the sealing piece 1995 and the lower end face 1926b of the tube 1975 against the bottom face of the port and thereby form a seal. The sleeve 1990 includes a portion 1999 which extends radially inward and pushes against and crimps the sleeve 1990 against a portion of the tube 1975. The inward extension portion 1999 thus keeps the combination of the sleeve 1990 and the tube 1975 attached as an assembly so that neither rotates independently of the other, but instead they rotate and move axially together as if a single piece. It will be appreciated that in the connected configuration shown in FIG. 33, the fluid passageway 1980 of the tube 1975 is of the same size and is aligned with the fluid passageway 1930 in the layer 1902, although it will be further appreciated that the fluid passageways 1980 and 1930 may be of differing sizes and shapes and may not be aligned. Those skilled in the art will appreciate that the connection assembly described and shown in this particular embodiment in FIG. 33 may be like one or more of those shown in the Hochgraeber patent noted above. It will be appreciated that the materials described above for other embodiments of the various portions and features of the manifold connection assemblies disclosed above (e.g., tubing, layer, block, port body, tip, etc.) may be the same for the manifold connection assembly shown in FIG. 33. For example, for use of the assembly in biocompatible environments and applications, the tube 1975, the sealing piece 1995, and the layer 1902 would comprise biocompatible materials. The sealing piece 1995 could comprise PEEK or other elastomeric or polymer materials, the tube 1975 could comprise a glass or silicate material, and the sleeve 1990 and/or the nut 1920 could comprise PEEK or other polymer materials, or could comprise steel or other materials if desired.

A manifold assembly like the manifold assembly 1100, 1200, or 1300 described above was built with the manifold 1105 made of 316L stainless steel and CP titanium, the block 1110 made of aluminum, and the plate 1115 made of aluminum. A capillary inner tube with an inner layer of PEEK having an inner diameter of 0.010 inches and an outer tubing layer of stainless steel and having a carbon fiber filled PEEK tip was attached to the manifold, and fluid at room temperature at pressure was run through the tube and the manifold assembly for testing purposes. We found that the manifold assembly and the connection tested was able to handle fluid pressures of up to about 30,000 psi without leaking or having the tube separate from the connection.

Those skilled in the art will appreciate that a manifold assembly like those described above can provide a number of advantages over conventional manifolds and manifold assemblies. For example, it will be appreciated that the manifold assemblies of the foregoing embodiments allow for fluidic connections which involve less parts, are easier to connect or disconnect, and provide fluid pathways which are shorter and smaller in length. Because many Analytical Instrumentation systems such as high pressure liquid chromatographs and ultra-high pressure liquid chromatographs are used for analysis of extremely low-volume samples, which may include samples of volumes anywhere from 50 nanoliters to several hundred microliters, the manifold assemblies of the foregoing disclosure are advantageous because the connections within the fluid system associated with said chromatograph systems can be made quickly and easily with fewer interconnecting tubes, and the elimination of volumes associated with conventional ferrule-type fitting assemblies, thereby minimizing added dead volume to the system.

A further advantage of the planar manifold assembly is that multiple fluid-handling functional devices may be coordinated and assembled in a small volume, and as part of the manifold. Multiple fluid passageways can be integrated into the planar manifold, which is itself quite compact and amenable to construction in a variety of shapes and configurations besides those shown and described herein. For example, it is contemplated that a planar manifold may be constructed in an irregular shape, such as a curved, bent, or multiple-angled configuration, so as to conform to an irregularly-shaped, compact volume. The manifold can be made with diffusion bonding techniques. In the diffusion bonding method, the members to be bonded to each other (such as the various layers of the manifold embodiments are described above) typically are held in close contact with each other, and pressed and heated to a pressure and temperature so that the bonding members are bonded by the diffusion of atoms which takes place in the interface between the bonded surfaces. Diffusion bonding usually provides satisfactory bonding strength, air-tightness, and pressure resistance that are useful for use in applications in a pressured fluid-handling system, such as an LC or AI system. Other alternative systems wherein laser welded manifolds such as those comprising sapphire or glass bonded to a metallic substrate, such as those described in United States published patent application number 2013/0112650, titled "Room Temperature Glass-to-Glass, Glass-to-Plastic and Glass-to-Ceramic/Semiconductor Bonding," and published May 9, 2013, which is hereby incorporated by reference herein as if fully set forth herein, may be used. High pressure sapphire to titanium and sapphire to sapphire bonding of laser etched microfluidic structures has been demonstrated and is believed to be commercially available from Invenios of Santa Barbara, Calif. Sapphire surfaces are generally optically smooth and provide an excellent sealing surface and resulting manifold for connections such as those described and illustrated in this disclosure.

Another advantage of the foregoing disclosure arises from the fact that it is typical in many LC and/or AI systems for certain dimensions and configurations to be fixed, such as those involving a valve or valves, pumps, column compartment, detector, or other component of the LC and/or AI system. Those skilled in the art will understand and appreciate that each one of the manifolds described above can be replaced with another manifold as may be desired, especially when the manifolds involved are intended for use in the same component of the LC and/or AI systems, such as for a valve for example. With respect to a valve, for example, those of skill in the art will appreciate that the number and relative position of the inlets and/or outlets within an LC or AI system are typically fixed in three-dimensional space within the instrument, thereby allowing for the use of different manifolds which have inlets and/or outlets which match those for the instrument. For example, the manifold 1105 as shown in FIGS. 17-19 may be replaced with a different manifold (not shown) which further comprises one or more MEMs features, such as a heating element, a pressure sensor, a temperature sensor, a flow rate sensor, an osmotic pump, or the like, thus allowing an operator to easily and quickly switch from a first to a second manifold for a second intended application of a valve (for example) in an LC system (for example) for a second intended use, such as where the second intended use involves testing or analysis in which the MEMs features are desirable but are not needed for the first use. In such situations, the operator or user can simply switch the manifolds and need not switch the valves or the entire LC system (in this particular example). Because an LC system and AI system can be and often is used for a wide variety of tests and analyses and with a wide variety of samples and effluents, those skilled in the art will appreciate that the ability to quickly and easily replace the manifold with another which is adapted for a different intended uses provides much greater flexibility and reduces the downtime costs associated with switching a valve in the LC or AI system, as an example.

While the present invention has been shown and described in various embodiments, those skilled in the art will appreciate from the drawings and the foregoing discussion that various changes, modifications, and variations may be made without departing from the spirit and scope of the invention as set forth in the claims. For example, the shapes, sizes, features, and materials of the fitting assembly, fluid connection, and/or analytical instrument systems of the present disclosure may be changed. Similarly, many of the particular embodiments described and illustrated herein use a nut to provide an axial load, but as noted previously, an axial load can be provided to provide a sealing engagement in a number of different ways. Hence, the embodiments shown and described in the drawings and the above discussion are merely illustrative and do not limit the scope of the invention as defined in the claims herein. The embodiments and specific forms, materials, and the like are merely illustrative and do not limit the scope of the invention or the claims herein.

We claim:
1. A manifold assembly comprising:
   at least one nut having a passageway therethrough and having a first end and a second end;
   a block adapted to removably hold a manifold and having a plurality of ports therein, wherein each of the ports are adapted to removably and sealingly engage with said nut and an end of a tube;
   a manifold having a plurality of inlet ports therein, wherein at least a portion of said manifold is attached to said block, and wherein each of the ports of said block is in fluid communication with one of the inlet ports of said manifold;
   a tube having a passageway therethrough and adapted to fit in a passageway extending through said nut, wherein said tube has a first end and a second end;
   a transfer tube having a passageway therethrough, wherein at least a portion of said tube is located within the passageway of said transfer tube and is secured relative to said transfer tube; and
   a tip having a passageway therethrough and providing an interior portion, wherein said tip is adjacent to and in contact with one of the first end and the second end of said tube, wherein said tip is adapted to receive and hold a portion of one of the first end and the second end of said tube in the interior portion, wherein at least a portion of one end of the tip is adapted to form a seal in a port in fluid communication with said manifold, and wherein a portion of the tip is located between a portion of said tube and a portion of said transfer tube.

2. The manifold assembly according to claim 1 wherein said manifold comprises a stator for a valve.

3. The manifold assembly according to claim 1 wherein said manifold comprises a stator for a valve in a liquid chromatography system.

4. The manifold assembly according to claim 1 wherein said manifold comprises two or more stators for multiple valve application in a liquid chromatography system.

5. The manifold assembly according to claim 1, wherein said tube comprises an inner tube and an outer tube.

6. The manifold assembly according to claim 1, wherein said tip comprises a compressible material and wherein at least one of said transfer tube and an inside surface of said tip are adapted to provide an interference fit with said tube.

7. The manifold assembly according to claim 1, wherein said transfer tube has a shorter length than said tube and wherein one end of said transfer tube is adapted to impinge on a portion of one end of said tip, thereby forcing said tip against a port bottom when an axial load is applied.

8. The manifold assembly according to claim 1, wherein said tube comprises a single metal, said transfer tube comprises a metal, and further wherein said transfer tube comprises a pocket portion at a terminal end thereof, and wherein said tip is adapted to be held in the pocket portion, thereby providing an interference seal with a portion of said tube.

9. The manifold assembly according to claim 1 wherein said tube and said tip each comprise a biocompatible material.

10. The manifold assembly according to claim 1 wherein at least one of said tube and said tip comprises at least one of the following: polyetheretherketone (PEEK), polyaryletherketone (PAEK), polyetherketone (PEK), polyetherketone etherketone ketone (PEKEKK), polyetherketoneketone (PEKK), fluorinated ethylene propylene (FEP), ethylene tetrafluoroethylene (ETFE), polytetrafluoro ethylene (PTFE), perfluoroalkoxy (PFA, also called perfluoroalkoxyethylene), polychlorotrifluoroethylene (PCTFE), polymer-sheathed fused silica (such as PEEKSil), fused silica, or silica borite.

11. The manifold assembly according to claim 1 further comprising a plate and wherein said manifold is located between a block and a plate.

12. The manifold assembly according to claim 11 wherein said manifold is located between a block and a plate, and the tip of said tubing forms a seal with a bottom end of a port in the block.

13. The manifold assembly according to claim 1 wherein the seal is sufficient to withstand fluidic pressures of at least 5,000 psi.

14. The manifold assembly according to claim 1 wherein the seal is sufficient to withstand fluidic pressures of at least 10,000 psi.

15. The manifold assembly according to claim 1 wherein the seal is sufficient to withstand fluidic pressures of at least 15,000 psi.

16. The manifold assembly according to claim 1 wherein said block has at least four ports on a first face thereof.

17. The manifold assembly according to claim 1 wherein said block has a first face and a second face, and has at least three edges, and further has at least two ports located on at least two of its edges.

18. The manifold assembly according to claim 1 wherein at least one fluid pathway of said manifold further comprises a flow sensor, a temperature sensor, a pressure sensor, a sample loop, or a pump.

19. A manifold assembly comprising
a manifold having a first face with plurality of inlet ports therein and having a plurality of openings in the face corresponding to each of the inlet ports, wherein each of the plurality of openings is adapted to receive and securely hold at least one projection;
at least one flat-bottomed port having a first end and a second end, wherein the second end of said port has a plurality of projections each adapted to removably fit into one of the openings in the face of said manifold, and wherein said port is adapted to receive and securely and removably hold therein a nut and an end of a tube;
a nut having a passageway therethrough and having one end adapted to fit into and securely and removably engage with said port;
a tube having a passageway therethrough and adapted to fit in the passageway of said nut, wherein said tube has a first end and a second end;
a transfer tube having a passageway therethrough, wherein at least a portion of said tube is located within the passageway of said transfer tube and is secured relative to said transfer tube; and
a tip having a passageway therethrough and providing an interior portion, wherein said tip is adjacent to and in contact with one of the first end and the second end of said tube, wherein said tip is adapted to receive and hold a portion of one of the first end and the second end of said tube in the interior portion, wherein at least a portion of one end of the tip is adapted to form a seal in a port in fluid communication with said manifold, and wherein a portion of the tip is located between a portion of said tube and a portion of said transfer tube.

20. The manifold assembly according to claim 19 wherein said manifold is adapted to provide a stator for a valve in an analytical instrument system.

21. The manifold assembly according to claim 20 wherein said manifold further comprises a plurality of inlet or outlet ports on the first face of said manifold and a plurality of fluid pathways between each of the inlet ports and each of the inlet or outlet ports of said manifold.

22. The manifold assembly according to claim 1, wherein said tip comprises a compressible material and wherein at least one of said transfer tube and an inside surface of said tip are adapted to provide an interference fit with said tube.

23. The manifold assembly according to claim 19 wherein the flat-bottomed port comprises an alignment mask to align a tip of the projection.

* * * * *